US010842830B2

(12) United States Patent
Cutcliffe et al.

(10) Patent No.: US 10,842,830 B2
(45) Date of Patent: *Nov. 24, 2020

(54) METHODS AND COMPOSITIONS RELATING TO MICROBIAL TREATMENT AND DIAGNOSIS OF DISORDERS

(71) Applicant: Pendulum Therapeutics, Inc., San Francisco, CA (US)

(72) Inventors: Colleen Cutcliffe, Menlo Park, CA (US); John S. Eid, San Francisco, CA (US); James H. Bullard, San Francisco, CA (US); Marcus F. Schicklberger, Richmond, CA (US)

(73) Assignee: Pendulum Therapeutics, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/159,532

(22) Filed: Oct. 12, 2018

(65) Prior Publication Data

US 2019/0070228 A1 Mar. 7, 2019

Related U.S. Application Data

(63) Continuation of application No. 15/271,672, filed on Sep. 21, 2016, which is a continuation of application No. 15/139,097, filed on Apr. 26, 2016, now Pat. No. 9,486,487, which is a continuation of application No. PCT/US2015/058511, filed on Oct. 30, 2015.

(60) Provisional application No. 62/073,912, filed on Oct. 31, 2014.

(51) Int. Cl.
| | | |
|---|---|---|
| *A61K 35/745* | (2015.01) | |
| *A23L 33/135* | (2016.01) | |
| *A61K 35/74* | (2015.01) | |
| *C12N 1/20* | (2006.01) | |
| *A61K 9/00* | (2006.01) | |
| *A61K 9/28* | (2006.01) | |
| *A61K 9/48* | (2006.01) | |
| *A61K 45/06* | (2006.01) | |
| *A61K 31/00* | (2006.01) | |
| *A61K 31/733* | (2006.01) | |
| *A61K 35/741* | (2015.01) | |
| *A61K 35/742* | (2015.01) | |
| *C12Q 1/689* | (2018.01) | |
| *G01N 33/66* | (2006.01) | |
| *A61K 35/00* | (2006.01) | |

(52) U.S. Cl.
CPC .......... *A61K 35/745* (2013.01); *A23L 33/135* (2016.08); *A61K 9/0053* (2013.01); *A61K 9/2846* (2013.01); *A61K 9/48* (2013.01); *A61K 9/4816* (2013.01); *A61K 9/4891* (2013.01); *A61K 31/00* (2013.01); *A61K 31/733* (2013.01); *A61K 35/74* (2013.01); *A61K 35/741* (2013.01); *A61K 35/742* (2013.01); *A61K 45/06* (2013.01); *C12N 1/20* (2013.01); *C12Q 1/689* (2013.01); *G01N 33/66* (2013.01); *A23V 2002/00* (2013.01); *A61K 2035/115* (2013.01); *G01N 2333/605* (2013.01); *G01N 2800/04* (2013.01)

(58) Field of Classification Search
CPC ........ C12N 1/20; A61K 35/745; A61K 35/74; A61K 35/741; C12R 1/145
See application file for complete search history.

(56) References Cited

U.S. PATENT DOCUMENTS

| | | | |
|---|---|---|---|
| 3,625,214 | A | 12/1971 | Higuchi et al. |
| 4,789,734 | A | 12/1988 | Ruoslahti et al. |
| 4,897,268 | A | 1/1990 | Tice et al. |
| 4,906,474 | A | 3/1990 | Langer et al. |
| 4,925,673 | A | 5/1990 | Steiner et al. |
| 5,075,109 | A | 12/1991 | Tice et al. |
| 5,143,845 | A | 9/1992 | Masuda et al. |
| 5,443,826 | A | 8/1995 | Borody |
| 5,744,134 | A | 4/1998 | Paul |
| 5,811,128 | A | 9/1998 | Tice et al. |
| 5,814,344 | A | 9/1998 | Tice et al. |
| 5,820,883 | A | 10/1998 | Tice et al. |
| 5,853,763 | A | 12/1998 | Tice et al. |
| 5,928,647 | A | 7/1999 | Rock et al. |
| 5,942,252 | A | 8/1999 | Tice et al. |
| 6,028,098 | A | 2/2000 | Goodman et al. |
| 6,241,983 | B1 | 6/2001 | Paul et al. |
| 6,479,051 | B1 | 11/2002 | Bruce et al. |
| 6,926,891 | B1 | 8/2005 | Neeser et al. |
| 6,960,341 | B2 | 11/2005 | Viscomi et al. |
| 7,033,764 | B2 | 4/2006 | Korlach et al. |
| 7,052,847 | B2 | 5/2006 | Korlach et al. |

(Continued)

FOREIGN PATENT DOCUMENTS

| | | |
|---|---|---|
| AU | 2012302364 A1 | 4/2014 |
| CA | 2851602 A1 | 3/2013 |

(Continued)

OTHER PUBLICATIONS

Hakansson et al., "Gut Microbiota and Inflammation" Nutrients, 2011, 3, 637-682 (Year: 2011).*

(Continued)

*Primary Examiner* — Ruth A Davis
(74) *Attorney, Agent, or Firm* — Wilson Sonsini Goodrich & Rosati

(57) ABSTRACT

The present disclosure provides methods, systems, compositions, and kits to address the need for microbiome-related treatment of health conditions and disease. The present disclosure provides for treatment of metabolic conditions using microbial compositions.

25 Claims, 16 Drawing Sheets

Specification includes a Sequence Listing.

(56) References Cited

U.S. PATENT DOCUMENTS

| | | | |
|---|---|---|---|
| 7,056,661 B2 | 6/2006 | Korlach et al. | |
| 7,056,676 B2 | 6/2006 | Korlach et al. | |
| 7,101,565 B2 | 9/2006 | Monte | |
| 7,183,101 B2 | 2/2007 | Arigoni et al. | |
| 7,195,906 B2 | 3/2007 | Collins et al. | |
| 7,307,062 B2 | 12/2007 | Bolte | |
| 7,550,285 B2 | 6/2009 | Schiffrin et al. | |
| 7,785,581 B2 | 8/2010 | Cui | |
| 7,862,808 B2 | 1/2011 | Isolauri et al. | |
| 7,947,482 B2 | 5/2011 | Molin et al. | |
| 7,988,960 B2 | 8/2011 | Isolauri et al. | |
| 8,329,672 B2 | 12/2012 | Rull et al. | |
| 8,343,482 B2 | 1/2013 | Bergonzelli et al. | |
| 8,460,648 B2 | 6/2013 | Borody | |
| 8,501,169 B2 | 8/2013 | Sanz et al. | |
| 8,529,887 B2 | 9/2013 | Schiffrin | |
| 8,557,233 B2 | 10/2013 | MacSharry et al. | |
| 8,709,398 B2 | 4/2014 | MacSharry et al. | |
| 8,728,794 B2 | 5/2014 | Miwa et al. | |
| 8,734,783 B2 | 5/2014 | Mogna et al. | |
| 8,802,179 B2 | 8/2014 | Miller | |
| 8,906,668 B2 | 12/2014 | Henn et al. | |
| 8,951,512 B2 | 2/2015 | Blaser et al. | |
| 9,011,834 B1 | 4/2015 | McKenzie et al. | |
| 9,028,841 B2 | 5/2015 | Henn et al. | |
| 9,040,101 B2 | 5/2015 | Heiman et al. | |
| 9,168,275 B2 | 10/2015 | Finegold | |
| 9,173,910 B2 | 11/2015 | Kaplan et al. | |
| 9,180,147 B2 | 11/2015 | McKenzie et al. | |
| 9,192,179 B2 | 11/2015 | Roughead et al. | |
| 9,192,554 B2 | 11/2015 | Guitard et al. | |
| 9,259,447 B2 | 2/2016 | Burcelin et al. | |
| 9,314,489 B2 | 4/2016 | Kelly et al. | |
| 9,339,055 B2 | 5/2016 | Fujiwara et al. | |
| 9,386,793 B2 | 7/2016 | Blaser et al. | |
| 9,408,872 B2 | 8/2016 | Borody et al. | |
| 9,415,079 B2 | 8/2016 | Honda et al. | |
| 9,421,230 B2 | 8/2016 | Honda et al. | |
| 9,433,650 B2 | 9/2016 | Nieuwdorp et al. | |
| 9,433,652 B2 | 9/2016 | Honda et al. | |
| 9,439,933 B2 | 9/2016 | Masuoka et al. | |
| 9,443,652 B2 | 9/2016 | Yoon et al. | |
| 9,446,080 B2 | 9/2016 | McKenzie et al. | |
| 9,463,169 B2 | 10/2016 | Heiman et al. | |
| 9,486,487 B2 * | 11/2016 | Cutcliffe | G01N 33/66 |
| 9,493,737 B2 | 11/2016 | Georgieva et al. | |
| 9,533,014 B2 | 1/2017 | Henn et al. | |
| 9,572,841 B2 | 2/2017 | Borody et al. | |
| 9,585,921 B2 | 3/2017 | McKenzie et al. | |
| 9,603,876 B2 | 3/2017 | Blaser et al. | |
| 9,623,055 B2 | 4/2017 | Nieuwdorp et al. | |
| 9,623,056 B2 | 4/2017 | Borody et al. | |
| 9,642,881 B2 | 5/2017 | Honda et al. | |
| 9,642,882 B2 | 5/2017 | Honda et al. | |
| 9,644,210 B2 | 5/2017 | Schrezenmeir et al. | |
| 9,649,345 B2 | 5/2017 | Honda et al. | |
| 9,649,346 B2 | 5/2017 | Klapper et al. | |
| 9,668,991 B1 | 6/2017 | Cahan | |
| 9,668,992 B1 | 6/2017 | Cahan | |
| 9,688,967 B2 | 6/2017 | Falb et al. | |
| 9,710,606 B2 | 7/2017 | Apte et al. | |
| 9,771,624 B2 | 9/2017 | Van Sinderen et al. | |
| 9,833,484 B2 | 12/2017 | Mogna et al. | |
| 1,014,986 A1 | 12/2018 | Kaplan et al. | |
| 1,014,987 A1 | 12/2018 | Kaplan et al. | |
| 2002/0013270 A1 | 1/2002 | Bolte | |
| 2004/0028689 A1 | 2/2004 | Borody | |
| 2004/0170617 A1 | 9/2004 | Finegold | |
| 2005/0112112 A1 | 5/2005 | Park et al. | |
| 2006/0115465 A1 | 6/2006 | MacFarlane et al. | |
| 2007/0014756 A1 | 1/2007 | Touchot | |
| 2007/0258953 A1 | 11/2007 | Duncan et al. | |
| 2008/0038240 A1 | 2/2008 | Farmer et al. | |
| 2008/0069861 A1 | 3/2008 | Brown et al. | |
| 2008/0145341 A1 | 6/2008 | Myatt et al. | |
| 2008/0254009 A1 | 10/2008 | Finegold | |
| 2008/0286252 A1 | 11/2008 | Sinnott et al. | |
| 2009/0010891 A1 | 1/2009 | Masuda et al. | |
| 2009/0010892 A1 | 1/2009 | Masuda et al. | |
| 2009/0010981 A1 | 1/2009 | Bechert et al. | |
| 2009/0169531 A1 | 7/2009 | Lacoste et al. | |
| 2009/0252708 A1 | 10/2009 | Fitzpatrick et al. | |
| 2010/0086528 A1 | 4/2010 | Olofsson et al. | |
| 2010/0087481 A1 | 4/2010 | Lee | |
| 2010/0172874 A1 | 7/2010 | Turnbaugh et al. | |
| 2010/0215738 A1* | 8/2010 | Ritter | A61K 31/702 424/456 |
| 2010/0284979 A1 | 11/2010 | O'Mahony et al. | |
| 2010/0331641 A1 | 12/2010 | Bangera et al. | |
| 2011/0081320 A1 | 4/2011 | Westall et al. | |
| 2011/0280840 A1 | 11/2011 | Blaser et al. | |
| 2011/0287072 A1 | 11/2011 | Ritter et al. | |
| 2012/0004111 A1 | 1/2012 | Colwell et al. | |
| 2012/0058094 A1 | 3/2012 | Blaser et al. | |
| 2012/0107291 A1 | 5/2012 | Burcelin et al. | |
| 2012/0165792 A1 | 6/2012 | Ortiz et al. | |
| 2012/0183514 A1 | 7/2012 | Mercenier et al. | |
| 2012/0230956 A1 | 9/2012 | McLean et al. | |
| 2012/0269865 A1 | 10/2012 | Roughead et al. | |
| 2013/0121968 A1 | 5/2013 | Quay | |
| 2013/0143288 A1 | 6/2013 | Mullin et al. | |
| 2013/0224155 A1 | 8/2013 | Kaplan et al. | |
| 2013/0266539 A1* | 10/2013 | Borody | A61K 35/741 424/93.3 |
| 2013/0280225 A1* | 10/2013 | Faure | A61K 31/702 424/93.45 |
| 2013/0296165 A1 | 11/2013 | Harel et al. | |
| 2014/0037688 A1 | 2/2014 | Berkes et al. | |
| 2014/0073610 A1 | 3/2014 | Ekwuribe | |
| 2014/0079676 A1 | 3/2014 | Olmstead | |
| 2014/0093478 A1 | 4/2014 | Turnbaugh et al. | |
| 2014/0135398 A1 | 5/2014 | Matar et al. | |
| 2014/0147417 A1 | 5/2014 | Sadowsky et al. | |
| 2014/0147425 A1 | 5/2014 | Henn et al. | |
| 2014/0286920 A1 | 9/2014 | Mayra-Makinen et al. | |
| 2014/0294774 A1 | 10/2014 | Nieuwdorp et al. | |
| 2014/0341921 A1 | 11/2014 | Honda et al. | |
| 2014/0363397 A1 | 12/2014 | Allen-Vercoe et al. | |
| 2015/0143557 A1 | 5/2015 | Honda et al. | |
| 2015/0190435 A1 | 7/2015 | Henn et al. | |
| 2015/0218507 A1 | 8/2015 | Georgieva et al. | |
| 2015/0232801 A1 | 8/2015 | Yde et al. | |
| 2015/0246081 A1 | 9/2015 | Morris | |
| 2015/0258151 A1 | 9/2015 | Mani et al. | |
| 2015/0259728 A1 | 9/2015 | Cutliffe et al. | |
| 2015/0306152 A1* | 10/2015 | Cani | A61K 35/741 424/93.4 |
| 2015/0306156 A1 | 10/2015 | Borody et al. | |
| 2015/0320805 A9 | 11/2015 | Honda et al. | |
| 2015/0320808 A1 | 11/2015 | Burcelin et al. | |
| 2015/0374760 A1 | 12/2015 | Scher et al. | |
| 2016/0000838 A1 | 1/2016 | Harmsen et al. | |
| 2016/0030494 A1 | 2/2016 | Henn et al. | |
| 2016/0040215 A1 | 2/2016 | Henn et al. | |
| 2016/0108442 A1 | 4/2016 | Adelstein et al. | |
| 2016/0113971 A1 | 4/2016 | Kaplan et al. | |
| 2016/0143961 A1 | 5/2016 | Berry et al. | |
| 2016/0143962 A1 | 5/2016 | Berry et al. | |
| 2016/0151431 A1 | 6/2016 | Borody et al. | |
| 2016/0151432 A1 | 6/2016 | Borody | |
| 2016/0151433 A1 | 6/2016 | Borody et al. | |
| 2016/0158294 A1 | 6/2016 | Von Maltzahn et al. | |
| 2016/0184370 A1 | 6/2016 | McKenzie et al. | |
| 2016/0193258 A1 | 7/2016 | Berry et al. | |
| 2016/0199424 A1 | 7/2016 | Berry et al. | |
| 2016/0228476 A1 | 8/2016 | Cutcliffe et al. | |
| 2016/0232311 A1 | 8/2016 | Segal et al. | |
| 2016/0232319 A1 | 8/2016 | Apte et al. | |
| 2016/0243172 A1 | 8/2016 | Cook et al. | |
| 2016/0243175 A1 | 8/2016 | Bushman et al. | |
| 2016/0263144 A1 | 9/2016 | O'Hara et al. | |
| 2016/0263153 A1 | 9/2016 | O'hara | |
| 2016/0263166 A1 | 9/2016 | Elinav et al. | |
| 2016/0271188 A1 | 9/2016 | Berry et al. | |

(56) References Cited

U.S. PATENT DOCUMENTS

| | | |
|---|---|---|
| 2016/0271189 A1 | 9/2016 | Cutcliffe et al. |
| 2016/0271190 A1 | 9/2016 | O'Hara et al. |
| 2016/0271191 A1 | 9/2016 | O'Hara |
| 2016/0287645 A1 | 10/2016 | O'Hara |
| 2016/0317432 A1 | 11/2016 | Garcia-Garcia et al. |
| 2016/0317589 A1 | 11/2016 | Nieuwdorp et al. |
| 2016/0317653 A1 | 11/2016 | Cook et al. |
| 2016/0342735 A1 | 11/2016 | Apte et al. |
| 2016/0354417 A1 | 12/2016 | Smittle et al. |
| 2016/0354418 A1 | 12/2016 | Quintens et al. |
| 2016/0354509 A1 | 12/2016 | Parlato et al. |
| 2016/0355847 A1 | 12/2016 | Liu et al. |
| 2016/0367661 A1 | 12/2016 | Flavell et al. |
| 2016/0375066 A1 | 12/2016 | Borody et al. |
| 2016/0375068 A1 | 12/2016 | Borody et al. |
| 2017/0000834 A1 | 1/2017 | Klosterbuer |
| 2017/0007691 A1 | 1/2017 | Honda et al. |
| 2017/0020932 A1 | 1/2017 | Cutcliffe et al. |
| 2017/0027876 A1 | 2/2017 | Caillard |
| 2017/0027996 A1 | 2/2017 | Cutcliffe et al. |
| 2017/0042860 A1 | 2/2017 | Kashyap et al. |
| 2017/0058270 A1 | 3/2017 | Garcia-Garcia et al. |
| 2017/0067065 A1 | 3/2017 | Falb et al. |
| 2017/0080015 A1 | 3/2017 | Heiman et al. |
| 2017/0095517 A1 | 4/2017 | Mayra et al. |
| 2017/0101484 A1 | 4/2017 | Naeye et al. |
| 2017/0106026 A1 | 4/2017 | Kovarik |
| 2017/0112915 A1 | 4/2017 | Honda et al. |
| 2017/0119828 A1 | 5/2017 | Nakamura et al. |
| 2017/0143774 A1 | 5/2017 | Mulder et al. |
| 2017/0151290 A1 | 6/2017 | Blaser et al. |
| 2017/0151291 A1 | 6/2017 | Henn et al. |
| 2017/0157034 A1 | 6/2017 | Klapper |
| 2017/0165201 A1 | 6/2017 | Anselmo et al. |
| 2017/0165302 A1 | 6/2017 | Henn et al. |
| 2017/0273997 A1 | 9/2017 | Sakwinska et al. |
| 2017/0304375 A1 | 10/2017 | Kyle et al. |
| 2017/0312232 A1 | 11/2017 | Vitetta et al. |
| 2018/0094233 A1 | 4/2018 | Belzer et al. |
| 2018/0357375 A1 | 12/2018 | Cutcliffe et al. |
| 2019/0030095 A1 | 1/2019 | Cutcliffe et al. |
| 2019/0030096 A1 | 1/2019 | Cutcliffe et al. |
| 2019/0038678 A1 | 2/2019 | De Vos |
| 2019/0046590 A1 | 2/2019 | Kaplan et al. |
| 2019/0070227 A1 | 3/2019 | Cutcliffe et al. |

FOREIGN PATENT DOCUMENTS

| | | |
|---|---|---|
| CN | 101410128 A | 4/2009 |
| CN | 104244733 A | 12/2014 |
| CN | 105030841 A | 11/2015 |
| CN | 105106245 A | 12/2015 |
| EP | 0456418 A2 | 11/1991 |
| EP | 0446069 B1 | 9/1993 |
| EP | 0456418 B1 | 9/1996 |
| EP | 1600060 A1 | 11/2005 |
| EP | 1359924 B1 | 10/2007 |
| EP | 2030623 A1 | 3/2009 |
| EP | 2439264 A1 | 4/2012 |
| EP | 2442814 A2 | 4/2012 |
| EP | 2318513 B1 | 9/2012 |
| EP | 1680501 B1 | 12/2012 |
| EP | 2117567 B1 | 6/2014 |
| EP | 2753187 A1 | 7/2014 |
| EP | 2836224 A2 | 2/2015 |
| EP | 2766026 A4 | 5/2015 |
| EP | 2789340 A4 | 7/2015 |
| EP | 2556835 B1 | 8/2015 |
| EP | 2919796 A1 | 9/2015 |
| EP | 2951285 A1 | 12/2015 |
| EP | 2953472 A1 | 12/2015 |
| EP | 2953474 A2 | 12/2015 |
| EP | 2956006 A2 | 12/2015 |
| EP | 2988761 A1 | 3/2016 |
| EP | 3052111 A1 | 8/2016 |
| EP | 3058085 A2 | 8/2016 |
| EP | 3074027 A1 | 10/2016 |
| EP | 3102670 A4 | 7/2017 |
| EP | 3223834 A2 | 10/2017 |
| EP | 3135754 A4 | 12/2017 |
| FR | 2874825 A1 | 3/2006 |
| JP | H08298982 A | 11/1996 |
| JP | 2006314219 A | 11/2006 |
| JP | 2007031291 A | 2/2007 |
| JP | 5019563 B2 | 9/2012 |
| KR | 20140128936 A | 11/2014 |
| RU | 2014112223 A | 10/2015 |
| WO | WO-9001335 A1 | 2/1990 |
| WO | WO-0015760 A1 | 3/2000 |
| WO | WO-0188095 A1 | 11/2001 |
| WO | WO-0193904 A1 | 12/2001 |
| WO | WO-0197822 A1 | 12/2001 |
| WO | WO-03070203 A1 | 8/2003 |
| WO | WO-2006000992 A1 | 1/2006 |
| WO | WO-2006013441 A2 | 2/2006 |
| WO | WO-2007046697 A2 | 4/2007 |
| WO | WO-2007046699 A2 | 4/2007 |
| WO | WO-2007125566 A2 | 11/2007 |
| WO | WO-2008076696 A2 | 6/2008 |
| WO | WO-2009018447 A2 | 2/2009 |
| WO | WO-2009024429 A2 | 2/2009 |
| WO | WO-2009077352 A1 | 6/2009 |
| WO | WO-2009153662 A1 | 12/2009 |
| WO | WO-2010036876 A2 | 4/2010 |
| WO | WO-2010108865 A1 | 9/2010 |
| WO | WO-2010146568 A2 | 12/2010 |
| WO | WO-2011043654 A1 | 4/2011 |
| WO | WO-2010146568 A3 | 5/2011 |
| WO | WO-2011096809 A1 | 8/2011 |
| WO | WO-2011099514 A1 | 8/2011 |
| WO | WO-2011135194 A2 | 11/2011 |
| WO | WO-2012021678 A2 | 2/2012 |
| WO | WO-2012024638 A2 | 2/2012 |
| WO | WO-2012033814 A2 | 3/2012 |
| WO | WO-2012122478 A1 | 9/2012 |
| WO | WO-2012142605 A1 | 10/2012 |
| WO | WO-2013032328 A1 | 3/2013 |
| WO | WO-2013050792 A1 | 4/2013 |
| WO | WO-2013050833 A1 | 4/2013 |
| WO | WO-2013107913 A1 | 7/2013 |
| WO | WO-2013130773 A2 | 9/2013 |
| WO | WO-2013175038 A1 | 11/2013 |
| WO | WO-2013191845 A1 | 12/2013 |
| WO | WO-2014011233 A1 | 1/2014 |
| WO | WO-2014070014 A1 | 5/2014 |
| WO | WO-2014075745 A1 | 5/2014 |
| WO | WO-2014076246 A1 | 5/2014 |
| WO | WO-2014082050 A1 | 5/2014 |
| WO | WO-2014121298 A2 | 8/2014 |
| WO | WO-2014121301 A1 | 8/2014 |
| WO | WO-2014121302 A2 | 8/2014 |
| WO | WO-2014121304 A1 | 8/2014 |
| WO | WO-2014137211 A1 | 9/2014 |
| WO | WO-2014145958 A2 | 9/2014 |
| WO | WO-2014151565 A1 | 9/2014 |
| WO | WO-2014152338 A1 | 9/2014 |
| WO | WO-2014153194 A2 | 9/2014 |
| WO | WO-2014121302 A3 | 10/2014 |
| WO | WO-2014201037 A2 | 12/2014 |
| WO | WO-2014153194 A4 | 1/2015 |
| WO | WO-2015013214 A2 | 1/2015 |
| WO | WO-2015051323 A1 | 4/2015 |
| WO | WO-2015067936 A1 | 5/2015 |
| WO | WO-2015067938 A1 | 5/2015 |
| WO | WO-2015067947 A1 | 5/2015 |
| WO | WO-2015067948 A1 | 5/2015 |
| WO | WO-2015067949 A1 | 5/2015 |
| WO | WO-2015077794 A1 | 5/2015 |
| WO | WO-2015088227 A1 | 6/2015 |
| WO | WO-2015095241 A2 | 6/2015 |
| WO | WO-2015131076 A1 | 9/2015 |
| WO | WO-2015166489 A2 | 11/2015 |
| WO | WO-2015166492 A2 | 11/2015 |
| WO | WO-2015095241 A4 | 12/2015 |

(56) References Cited

FOREIGN PATENT DOCUMENTS

| | | |
|---|---|---|
| WO | WO-2015189472 A1 | 12/2015 |
| WO | WO-2016013921 A2 | 1/2016 |
| WO | WO-2016065419 A1 | 5/2016 |
| WO | WO-2016070151 A1 | 5/2016 |
| WO | WO-2016079731 A2 | 5/2016 |
| WO | WO-2016084029 A1 | 6/2016 |
| WO | WO-2016110585 A1 | 7/2016 |
| WO | WO-2016118730 A1 | 7/2016 |
| WO | WO-2016139217 A1 | 9/2016 |
| WO | WO-2016149149 A1 | 9/2016 |
| WO | WO-2016149687 A1 | 9/2016 |
| WO | WO-2016174677 A1 | 11/2016 |
| WO | WO-2016176380 A1 | 11/2016 |
| WO | WO-2016177797 A1 | 11/2016 |
| WO | WO-2016177801 A1 | 11/2016 |
| WO | WO-2016185469 A1 | 11/2016 |
| WO | WO-2016186243 A1 | 11/2016 |
| WO | WO-2016194427 A1 | 12/2016 |
| WO | WO-2016196440 A1 | 12/2016 |
| WO | WO-2016201053 A1 | 12/2016 |
| WO | WO-2017009187 A1 | 1/2017 |
| WO | WO-2017019273 A1 | 2/2017 |
| WO | WO-2017024237 A1 | 2/2017 |
| WO | WO-2017032897 A1 | 3/2017 |
| WO | WO-2017035188 A1 | 3/2017 |
| WO | WO-2017035412 A1 | 3/2017 |
| WO | WO-2017041039 A1 | 3/2017 |
| WO | WO-2017042347 A1 | 3/2017 |
| WO | WO-2017047968 A1 | 3/2017 |
| WO | WO-2017060468 A1 | 4/2017 |
| WO | WO-2017060698 A1 | 4/2017 |
| WO | WO-2017063066 A1 | 4/2017 |
| WO | WO-2017075098 A1 | 5/2017 |
| WO | WO-2017079450 A1 | 5/2017 |
| WO | WO-2017091783 A2 | 6/2017 |
| WO | WO-2017097987 A1 | 6/2017 |
| WO | WO-2017102816 A1 | 6/2017 |
| WO | WO-2017130859 A1 | 8/2017 |
| WO | WO-2018106844 A1 | 6/2018 |
| WO | WO-2019046646 A1 | 3/2019 |

OTHER PUBLICATIONS

Franks et al., "Variations in Bacterial Populations in Human Feces Measured by Fluorescent in Situ Hybridization with Group Specific 16S rRNA targeted Oligonucleotide Probes", Applied and Environmental Microbiology, Sep. 1998, 3336-3345 (Year: 1998).*

U.S. Appl. Nos. 15/271,672; 15/286,218; 16/159,524; 16/159,536; 16/159,537 (Year: 2018).*

Rossi-Tamisier et al., "Cautionary tale of using 16S rRNA gene sequence similarity values in identification of human-associated bacterial species" International Journal of Systematic and Evolutionary Microbiology vol. 65, Issue 6, 1929-1934 (Year: 2015).*

Edgar, "Updating the 97% Identity Threshold for 16S Ribosomal RNA OTUs" Bioinformatics, 34 (14), 2371-2375 Jul. 15, 2018, 2371-2375 (Year: 2018).*

Beye et al., "Careful use of 16S rRNA gene sequence similarity values for the identification of *Mycobacterium* species", New Microbes New Infect. Mar. 2018; 22: 24-29. Published online Dec. 29, 2017 (Year: 2018).*

Baker. The role of microorganisms in atopic dermatitis. Clin Exp Immunol. Apr. 2006;144(1):1-9.

Clayton. Metabolic differences underlying two distinct rat urinary phenotypes, a suggested role for gut microbial metabolism of phenylalanine and a possible connection to autism. FEBS Lett. Apr. 5, 2012;586(7):956-61. doi: 10.1016/j.febslet.2012.01.049. Epub Feb. 1, 2012.

Cork, et al. Epidermal Barrier Dysfunction in Atopic Dermatitis. J Invest Dermatol. Aug. 2009;129(8):1892-908. doi: 10.1038/jid.2009. 133. Epub Jun. 4, 2009.

European search report with written opinion dated Nov. 19, 2018 for EP Application No. 16765880.

Grasset, et al. A Specific Gut Microbiota Dysbiosis of Type 2 Diabetic Mice Induces GLP-1 Resistance through an Enteric NO-Dependent and Gut-Brain Axis Mechanism. Cell Metab. May 2, 2017;25(5):1075-1090.e5. doi: 10.1016/j.cmet.2017.04.013.

International search report with written opinion dated Nov. 23, 2018 for PCT/US18/48955.

Kober, et al. The effect of probiotics on immune regulation, acne, and photoaging. Int J Womens Dermatol. Apr. 6, 2015;1(2):85-89. doi: 10.1016/j.ijwd.2015.02.001. eCollection Jun. 2015.

Leung. New Insights into Atopic Dermatitis: Role of Skin Barrier and Immune Dysregulation. Allergol Int. Jun. 2013;62(2):151-61. doi: 10.2332/allergolint.13-RAI-0564.

Levkovich, et al. Probiotic Bacteria Induce a 'Glow of Health'. PLoS One. 2013;8(1):e53867. doi: 10.1371/journal.pone.0053867. Epub Jan. 16, 2013.

Office action dated Jan. 11, 2019 for U.S. Appl. No. 15/286,218.

Office action dated Dec. 13, 2018 for U.S. Appl. No. 16/159,536.

Panther, et al. The Importance of Acidification in Atopic Eczema: An Underexplored Avenue for Treatment. J Clin Med. May 18, 2015;4(5):970-8. doi: 10.3390/jcm4050970.

Psichas, et al. The short chain fatty acid propionate stimulates GLP-1 and PYY secretion via free fatty acid receptor 2 in rodents. Int J Obes (Lond). Mar. 2015;39(3):424-9. doi: 10.1038/ijo.2014. 153. Epub Aug. 11, 2014.

Rippke, et al. Stratum Corneum pH in Atopic Dermatitis: Impact on Skin Barrier Function and Colonization with *Staphylococcus aureus*. Am J Clin Dermatol. 2004;5(4):217-23.

Roudsari, et al. Health Effects of Probiotics on the Skin. Crit Rev Food Sci Nutr. 2015;55(9):1219-40. doi: 10.1080/10408398.2012. 680078.

Sharma, et al. Glucagon-like peptide-1 (GLP-1) receptor agonist prevents development of tolerance to anti-anxiety effect of ethanol and withdrawal-induced anxiety in rats. Metab Brain Dis. Jun. 2015;30(3):719-30. doi: 10.1007/s11011-014-9627-z. Epub Nov. 8, 2014.

Wang, et al. *Staphylococcus epidermidisin* the human skin microbiome mediates fermentation to inhibit the growth of Propionibacterium acnes: implications of probiotics in acne vulgaris. Appl Microbiol Biotechnol. Jan. 2014;98(1):411-24. doi: 10.1007/s00253-013-5394-8. Epub Nov. 22, 2013.

Williams, et al. Evidence that Human Skin Microbiome Dysbiosis Promotes Atopic Dermatitis. J Invest Dermatol. Dec. 2017;137(12):2460-2461. doi: 10.1016/j.jid.2017.09.010.

Williams, et al. The Role of the Skin Microbiome in Atopic Dermatitis. Curr Allergy Asthma Rep. Nov. 2015;15(11):65. doi: 10.1007/s11882-015-0567-4.

Abdallah, et al. Frequency of Firmicutes and Bacteroidetes in gut microbiota in obese and normal weight Egyptian children and adults. Arch Med Sci. Jun. 2011;7(3):501-7. doi: 10.5114/aoms. 2011.23418. Epub Jul. 11, 2011.

Abrahamsson, et al. Low Diversity of the Gut Microbiota in Infants with Atopic Eczema. J Allergy Clin. Immunol. 2012; 129:434-40.

Agarwal, et al. The current and future state of companion diagnostics. Pharmgenomics Pers Med. Mar. 31, 2015;8:99-110. doi: 10.2147/PGPM.S49493. eCollection 2015.

Alger, et al. Multisite, multimodal neuroimaging of chronic urological pelvic pain: Methodology of the Mapp Research Network. Neuroimage Clin. Jan. 6, 2016;12:65-77. doi: 10.1016/j.nicl.2015. 12.009. eCollection 2016.

Amar, et al. (2011). Intestinal mucosal adherence and translocation of commensal bacteria at the early onset of type 2 diabetes: molecular mechanisms and probiotic treatment. EMBO Mol. Med. 3, 559-572. doi: 10.1002/emmm. 201100159.

Anonymous. Allergies; New findings from Hokkaido University describe advances in allergies. Clinical Trials Week [Atlanta] (Mar. 22, 2010): 42.

Anonymous. Clostridium; New clostridium data have been reported by scientists at Ghent University. Science Letter [Atlanta] (Aug. 17, 2010): 1811.

Anonymous. Nutrition; Research on nutrition detailed by scientists at Institute of Agrochemistry and Food Technology. Obesit, Fitness & Wellness Week [Atlanta] (Jul. 17, 2010): 2819.

(56) References Cited

OTHER PUBLICATIONS

Asano, et al. Critical role of gut microbiota in the production of biologically active, free catecholamines in the gut lumen of mice. Am J Physiol Gastrointest Liver Physiol. Dec. 1, 2012;303(11):G1288-95. doi: 10.1152/ajpgi.00341.2012. Epub Oct. 11, 2012.
"ATCC Catalogue, accessed Dec. 14, 2017. https://www.atcc.org/Search_Results.aspx?dsNav=Ntk:PrimarySearch°/07cClostridium+beijerinckii°/07c3')/07c,Ny:True,Rpp:100,N:1000552&searchTerms=Clostridium+beijerinckii&redir=1.".
Axling, et al. Green tea powder and *Lactobacillus plantarum* affect gut microbiota, lipid metabolism and inflammation in high-fat fed C57BL/6J mice. Nutr Metab (Lond). Nov. 26, 2012;9(1):105. doi: 10.1186/1743-7075-9-105.
Aziz, et al. Changes in gut hormones and fecal bacterial community composition in response to diet-induced obesity in the rat. Obesity, suppl. 1 19 (Nov. 2011): S166-S167.
Bach, et al. The presence of HLA-B27 shapes gut microbiome composition in rats. Arthritis and Rheumatism, suppl. 10 64 (Oct. 2012): S1052-S1053.
Baffoni, et al. Effect of dietary supplementation of *Bifidobacterium* and *Lactobacillus* strains *Apis mellifera* L. against *Nosema ceranae*. Benef Microbes. Nov. 13, 2015:1-8. [Epub ahead of print].
Baviera, et al. Microbiota in Healthy Skin and in Atopic Eczema. Hindawi Publishing Corporation, BioMed Research International, vol. 2014.
Belzer, et al. (2012). Microbes inside-from diversity to function: the case of Akkermansia. ISME J. 6, 1449-1458. doi: 10.1038/ISMEJ.2012.6.
Berridge. 'Liking' and 'Wanting' food rewards: brain substrates and roles in eating disorders. Physiol Behav. Jul. 14, 2009;97(5):537-50. doi: 10.1016/j.physbeh.2009.02.044. Epub Mar. 29, 2009.
Berry, et al, Phylotype-level 16S rRNA analysis reveals new bacterial indicators of health state in acute murine colitis, ISME Journal 6.11 (Nov. 2012): 2091-2106.
Bick, et al.From research to clinical practice: implementation of functional magnetic imaging and white matter tractography in the clinical environment. J Neurol Sci. Jan. 15, 2012;312(1-2):158-65. doi: 10.1016/j.jns.2011.07.040. Epub Aug. 23, 2011.
Bjelland, et al. The validity of the Hospital Anxiety and Depression Scale. An updated literature review. J Psychosom Res. Feb. 2002;52(2):69-77.
BMS acquires Amylin Pharmaceuticals, expands diabetes alliance with AstraZeneca. Jul. 2, 2012. 4 pages. http://www.centerwatch.com/news-online/2012/07/02/bms-acquires-amylin-pharmaceuticals-expands-diabetes-alliance-with-astrazeneca/.
Bourassa, et al., Butyrate, neuroepigenetics and the gut microbiome: can a high fiber diet improve brain health, Neuroscience Letters, 2016, 625:56-63.
Bourhis, et al. Contribution of C. beijerinckii and C. sporogenes in association with C. tyrobutyricum to the butyric fermentation in Emmental type cheese. International Journal of Food Microbiology. 113 (2007) 154-163.
Bravo, Ingestion of Lactobacillus strain regulates emotional behavior and central GABA receptor expression in a mouse via the vagus nerve. Proc Natl Acad Sci U S A. Sep. 20, 2011;108(38):16050-5. doi: 10.1073/pnas.1102999108. Epub Aug. 29, 2011.
Brown. "Akkermansia: new discoveries from the microbiome", Functional Medicine, Masterclass, Sep. 20, 2014, XP055327009.
Bueter; et al., "Gastric Bypass Increases Energy Expenditure in Rats. Gastroenterology", Gastroenterology, Gastroenterology, 2010, 138(5), 1845-1853.
Burger, et al. A functional neuroimaging review of obesity, appetitive hormones and ingestive behavior. Physiol Behav. Sep. 2014;136:121-7. doi: 10.1016/j.physbeh.2014.04.025. Epub Apr. 21, 2014.
Candela, et al, Unbalance of intestinal microbiota in atopic children, BMC Microbiology 12 (Jun. 6, 2012).

Cani, et al. (2004). Inulin-type fructans modulate gastrointestinal peptides involved in appetite regulation (glucagon-like peptide-1 and ghrelin) in rats. Br. J. Nutr. 92, 521-526. doi: 10.1079/BJN20041225.
Cani, et al. (2006). Improvement of glucose tolerance and hepatic insulin sensitivity by oligofructose requires a functional glucagon-like peptide 1 receptor. Diabetes Metab. Res. Rev. 55, 1484-1490. doi: 10.2337/db05-1360.
Cani, et al. (2007). Metabolic endotoxemia initiates obesity and insulin resistance. Diabetes Metab. Res. Rev. 56, 1761-1772. doi: 10.2337/db06-1491.
Cani, et al. (2009). Changes in gut microbiota control inflammation in obese mice through a mechanism involving GLP-2-driven improvement of gut permeability. Gut 58, 1091-1103. doi: 10.1136/gut.2008.165886.
Cani. Gut microbiota, low grade inflammation and metabolism. Appetite, suppl. 1 59 Jul. 2012: e11.
Cappelleri, et al. Psychometric analysis of the Three-Factor Eating Questionnaire-R21: results from a large diverse sample of obese and non-obese participants. Int J Obes (Lond). Jun. 2009;33(6):611-20. doi: 10.1038/ijo.2009.74. Epub Apr. 28, 2009.
Caricilli, et al. (2011). Gut microbiota is a key modulator of insulin resistance in TLR 2 knockout mice. PLOS Biol. 9:e1001212. doi: 10.1371/journal.pbio.1001212.
Casellas, et al, Defective Akkermansia Muciniphila in Feces of Ulcerative Colitis Patients, Northern Light Life Sciences Conference Abstracts (Oct. 24, 2011).
Chao, et al. Food cravings, food intake, and weight status in a community-based sample. Eat Behav. Aug. 2014;15(3):478-82. doi: 10.1016/j.eatbeh.2014.06.003. Epub Jun. 18, 2014.
Chen, et al. Bifidobacterium adolescentis supplementation ameliorates visceral fat accumulation and insulin sensitivity in an experimental model of the metabolic syndrome. Br Nutr. May 2012;107(10):1429-34. doi: 10.1017/S0007114511004491. Epub Sep. 14, 2011.
"Clarke, G. Society for Neuroscience (SFN) 2015 Annual Meeting. Abstract 162.04. Presented Oct. 18, 2015.".
Collado, et al. (2007). Intestinal integrity and Akkermansia muciniphila, a mucin-degrading member of the intestinal microbiota present in infants, adults, and the elderly. Appl. Environ. Microbiol. 73, 7767-7770. doi: 10.1128/AEM.01477-07.
Co-pending U.S. Appl. No. 16/159,524, filed Oct. 12, 2018.
Co-pending U.S. Appl. No. 16/159,536, filed Oct. 12, 2018.
Co-pending U.S. Appl. No. 16/159,537, filed Oct. 12, 2018.
Costello, et al. Postprandial remodeling of the gut microbiota in Burmese pythons. ISME J. Nov. 2010;4(11):1375-85. doi: 10.1038/ismej.2010.71. Epub Jun. 3, 2010.
Cryan, et al. Mind-altering microorganisms: the impact of the gut microbiota on brain and behaviour. Nat Rev Neurosci. Oct. 2012;13(10):701-12. doi: 10.1038/nrn3346. Epub Sep. 12, 2012.
Culligan, et al, Functional metagenomics reveals novel salt tolerance loci from the human gut microbiome. ISME Journal 6.10 (Oct. 2012): 1916-1925.
Dailey, et al. Glucagon-like peptide 1 and appetite. Trends Endocrinol Metab. Feb. 2013;24(2):85-91. doi: 10.1016/j.tem.2012.11.008. Epub Jan. 16, 2013.
"De Leoz, et al., Human Milk Glycomics and Gut Microbial Genomics in Infant Feces Show a Correlation between Human Milk Oligosaccharides and Gut Microbiota: A Proof-of-Concept Study, J. Proteome Res., 2015, 14:491-502".
De Vadder, et al. Microbiota-generated metabolites promote metabolic benefits via gut-brain neural circuits. Cell. Jan. 16, 2014;156(1-2):84-96. doi: 10.1016/j.cell.2013.12.016. Epub Jan. 9, 2014.
Delahanty, et al. Psychological and behavioral correlates of baseline BMI in the diabetes prevention program (DPP). Diabetes Care. Nov. 2002;25(11):1992-8.
Derrien, et al. (2008). The Mucin degrader Akkermansia muciniphila is an abundant resident of the human intestinal tract. Appl. Environ. Microbiol. 74, 1646-1648. doi: 10.1128/AEM.01226-07.
Derrien, et al. (2011). Modulation of mucosal immune response, tolerance, and proliferation in mice colonized by the mucin-degrader Akkermansia muciniphila. Front. Microbiol. 2:166. doi: 10.3389/fmicb.2011.00166.

(56) References Cited

OTHER PUBLICATIONS

Derrien, et al., *Akkermansia muciniphila*, gen. nov., sp. nov., a novel intestinal mucin-degrading bacterium, FEMS Congress of European Microbiologists Abstract Book 1 (2003): 237.

Derrien, et al. Mucin-bacterial interactions in the human oral cavity and digestive tract. Gut Microbes. Jul.-Aug. 2010; 1(4): 254-268.

Derrien. Mucin utilisation and host interactions of the novel intestinal microbe Akkermansia muciniphila. 2007.

Dewulf, et al. (2011). Inulin-type fructans with prebiotic properties counteract GPR43 overexpression and PPARgamma-related adipogenesis in the white adipose tissue of high-fat diet-fed mice. J. Nutr. Biochem. 22, 712-722. doi: 10.1016/j.jnutbio.2010.05.009.

Diamant, et al. Do nutrient—gut—microbiota interactions play a role in human obesity, insulin resistance and type 2 diabetes? Obesity reviews. 2011; 12:272-281.

Diaz Heijtz, et al. Normal gut microbiota modulates brain development and behavior. Proc Natl Acad Sci U S A. Feb. 15, 2011;108(7):3047-52. doi: 10.1073/pnas.1010529108. Epub Jan. 31, 2011.

Donohoe, et al. A gnotobiotic mouse model demonstrates that dietary fiber protects against colorectal tumorigenesis in a microbiota- and butyrate-dependent manner. Cancer Discov. Dec. 2014;4(12):1387-97. doi: 10.1158/2159-8290.CD-14/0501. Epub Sep. 29, 2014.

Donohoe, et al. The microbiome and butyrate regulate energy metabolism and autophagy in the mammalian colon. Cell Metab. May 4, 2011;13(5):517-26. doi: 10.1016/j.cmet.2011.02.018.

Dray, et al. Co-inertia analysis and the linking of ecological data tables. Ecology. 2003; 84(11):3078-3089.

Dubourg, et al. (2013). High-level colonisation of the human gut by Verrucomicrobia following broad-spectrum antibiotic treatment. Int. J. Antimicrob. Agents 41, 149-155. doi: 10.1016/j.ijantimicag.2012.10.012.

Endo, et al. Butyrate-producing probiotics reduce nonalcoholic fatty liver disease progression in rats: new insight into the probiotics for the gut-liver axis. PLoS One. May 16, 2013;8(5):e63388. doi: 10.1371/journal.pone.0063388. Print 2013.

Epel, et al. The reward-based eating drive scale: a self-report index of reward-based eating. PLoS One. Jun. 30, 2014;9(6):e101350. doi: 10.1371/journal.pone.0101350. eCollection 2014.

Erickson, et al. Integrated metagenomics/metaproteomics reveals human host-microbiota signatures of Crohn's disease. PLoS One. 2012;7(11):e49138. doi: 10.1371/journal.pone.0049138. Epub Nov. 28, 2012.

Everard, et al. (2011). Responses of gut microbiota and glucose and lipid metabolism to prebiotics in genetic obese and diet-induced leptin-resistant mice. Diabetes Metab. Res. Rev. 60, 2775-2786. doi: 10.2337/db11-0227.

Everard, et al. (2013). Cross-talk between Akkermansia muciniphila and intestinal epithelium controls diet-induced obesity. Proc. Natl. Acad. Sci. U.S.A. 110, 9066-9071. doi: 10.1073/pnas.1219451110.

Everard, et al. Gut microbiota and GLP-1. Rev Endocr Metab Disord. Sep. 2014;15(3):189-96. doi: 10.1007/s11154-014-9288-6.

Fabriciaus et al. Quantitative investigations into the elimination of in vitro-obtained spores of the non-pathogenic Clostridium butyricum strain CNRZ 528, and their persistence in organs of different species following intravenous spore administration. Res. Microbiol. 1993, vol. 144, pp. 741-753.

Falony et al. Cross-Feeding between Bifidobacterium longum BB536 and Acetate-Converting, Butyrate-Producing Colon Bacteria during Growth on Oligofructos. Appl. Environ. Microbiol. 72(12):7835-7841 (2006).

Flores, et al. Microbiome of Affected and Unaffected Skin of Patients with Atopic Dermatitis Before and After Emollient Treatment. Journal of Drugs in Dermatology, Nov. 2014, vol. 13, Issue 11, pp. 611-618.

Flores, et al. Skin Microbiome Diversity in Patients with Atopic Dermatitis Before and After Emollient Treatment.

Ganesh, et al. Enterococcus faecium NCIMB 10415 does not protect interleukin-10 knock-out mice from chronic gut inflammation. Beneficial Microbes 3.1 (Mar. 2012): 43-50.

Gao, et al., Butyrate Improves Insulin Sensitivity and Increases Energy Expenditure in Mice, Diabetes, Jul. 2009, 58:1509-17.

Gearhardt, et al. Preliminary validation of the Yale Food Addiction Scale. Appetite. Apr. 2009;52(2):430-6. doi: 10.1016/j.appet.2008.12.003. Epub Dec. 11, 2008.

Gibbs et al. Urocanic Acid in the Skin: A Mixed Blessing? Journal of Investigative Dermatology (2011) 131, 14-17.

Gibson, et al. (1995). Dietary modulation of the human colonic microbiota: introducing the concept of prebiotics. J. Nutr. 125, 1401-1412.

Gibson, et al. "Inulin and Oligofructose: New Scientific Developments", Nutrition Today, Mar. 1, 2008, pp. 54-59, XP055327770.

Gomez-Gallego, et al. Akkermansia muciniphila: a novel functional microbe with probiotic properties. Benef Microbes. Jun. 2016 13:1-14. doi:10.3920/BM2016.0009.

Gomez-Gallego, et al. Infant formula supplemented with polyamines alters the intestinal microbiota in neonatal BALB/cOlaHsd mice. J Nutr Biochem. Nov. 2012;23(11):1508-13. doi: 10.1016/j.jnutbio.2011.10.003. Epub Mar. 7, 2012.

Grice, E. The Skin Microbiome: Potential for Novel Diagnostic and Therapeutic Approaches to Cutaneous Disease. Semin Cutan Med Surg, 2014, 33:98-103.

Grzeskowiak, et al, The impact of perinatal probiotic intervention on gut microbiota: Double-blind placebo-controlled trials in Finland and Germany, Anaerobe 18.1 (Feb. 2012): 7-13.

Gupta, et al. Patterns of brain structural connectivity differentiate normal weight from overweight subjects. Neuroimage Clin. Jan. 13, 2015;7:506-17. doi: 10.1016/j.nicl.2015.01.005. eCollection 2015.

"Hai Suisan Shigen Oyobi Shokuhin Kako Zansa o Genryo to suru Kokinosei Hakko Shiryo Seizo Gijutsu no Kaihatsu", Heisei 22 Nendo Senryakuteki Kiban Gijutsu Kodoka Shien Jigyo Kenkyu Seika Hokokusho. Kanto Bureau of Economy, Trade and Industry. 2011, pp. 1-26.

Hamer, et al. Review article: the role of butyrate on colonic function. Aliment Pharmacol Ther. Jan. 15, 2008;27(2):104-19. Epub Oct. 25, 2007.

Hansen, et al., Early life treatment with vancomycin propagates Akkermansia muciniphila and reduces diabetes incidence in the NOD mouse, Diabetologia (2012), 55:2285-2294.

Hendrickson et al., Remington: The Science and Practice of Pharmacy, 21st Edition; Lippincott Williams & Wilkins: Philadelphia, PA, 2005; pp. 889-938.

Henry Ford Health Clinic, Endocrinology, Diabetes and Bone Mineral Disorders webcite information. 2016. 2 pages. http://www.henryford.com/body_academic.cfm?id=52450.

Hildebrand, et al, A comparative analysis of the intestinal metagenomes present in guinea pigs (*Cavia porcellus*) and humans (*Homo sapiens*, BMC Genomics 13 (Sep. 28, 2012).

Hu; et al., "Type 1 Diabetes and Gut Microbiota: Friend or Foe? Pharmacological Research 98 (2015): 9-15.".

"International search report and written opinion dated Jan. 27, 2016 for PCT Application No. US2015/058511.".

"International search report and written opinion dated May 13, 2013 for PCT Application US-201328271".

International search report and written opinion dated Jun. 17, 2016 for PCT/US2016/023311.

Isolauri, et al. Probiotics in the management of atopic eczema. Clin Exp Allergy. Nov. 2000;30(11):1604-10.

Jain. Strategies and technologies for drug delivery systems. Trends in Pharmacological Sciences 1998;19:155-157.

Johnson, et al. Is primary prevention of Clostridium difficile infection possible with specific probiotics? Int J Infect Dis. Nov. 2012;16(11):e786-92. doi: 10.1016/j.ijid.2012.06.005. Epub Aug. 3, 2012.

Kalliomaki, et al. Probiotics in primary prevention of atopic disease: a randomised placebo-controlled trial. Lancet. Apr. 7, 2001;357(9262):1076-9.

Kamneva, et al, Analysis of Genome Content Evolution in PVC Bacterial Super-Phylum: Assessment of Candidate Genes Associated with Cellular Organization and Lifestyle, Genome Biology and Evolution 4.12 (2012): 1375-1390.

(56) References Cited

OTHER PUBLICATIONS

"Karlsson, et al. Gut metagenome in European women with normal, impaired and diabetic glucose control. Nature. Jun. 6, 2013;498(7452):99-103. doi: 10.1038/nature12198. Epub May 29, 2013.".

Karlsson, et al, The Microbiota of the Gut in Preschool Children With Normal and Excessive Body Weight, Obesity 20.11 (Nov. 2012): 2257-2261.

Khan, et al., Pathophysiology and Treatment of Type 2 Diabetes: Perspectives on the Past, Present and Future, Lancet, Mar. 22, 2014, 383(9922):1068-1083.

Kilpatrick, et al. Influence of sucrose ingestion on brainstem and hypothalamic intrinsic oscillations in lean and obese women. Gastroenterology. May 2014;146(5):1212-21. doi: 10.1053/j.gastro.2014.01.023. Epub Jan. 28, 2014.

Kim, et al. Effects of Probiotics for the Treatment of Atopic Dermatitis: A Meta-Analysis of Randomized Controlled Trials. Ann. Allergy Asthma Immunol 113 (2014): 217-226.

Kinumaki, et al. Longitudinal analysis of gut flora in Kawasaki disease patients using next- generation DNA sequencing. Pediatrics International, suppl. 1 54 (Feb. 2012): 81.

Knip, et al. The role of the intestinal microbiota in type 1 diabetes mellitus. Nat Rev Endocrinol. Mar. 2016;12(3):154-67. doi: 10.1038/nrendo.2015.218. Epub Jan. 4, 2016.

Komaroff. How the Microbiome Might Promote Metabolic Syndrome and Obesity. Anthony L. Komaroff, MD reviewing Perry RJ et al. Nature Jun. 9, 2016. Trajkovski M and Wollheim CB. Nature Jun. 9, 2016. Published Jul. 14, 2016.

Kong et al. Temporal shifts in the skin microbiome associated with disease flares and treatment in children with atopic dermatitis. Genome Res 22(5):850-859 (2012).

Kuhn, et al. Applied predictive modeling. Springer, 2013. 595 pages.

Lamont. Infection in the prediction and antibiotics in the prevention of spontaneous preterm labour and preterm birth. BJOG: an International Journal of Obstetrics and Gynaecology. 2003; 110(Suppl 20):71-75.

Le Barz, et al. Probiotics as Complementary Treatment for Metabolic Disorders. Diabetes Metab J. Aug. 2015; 39(4): 291-303. doi:10.4093/dmj.2015.39.4.291.

Lebourhis et al. Development and Validation of PCR Primers to Assess the Diversity of *Clostridium* spp. in Cheese by Temporal Temperature Gradient Gel Electrophoresis. Applied and Environmental Microbiology, Jan. 2005, p. 29-38 vol. 71.

Levinson et al., Acute Gastrointestinal Graft-vs-Host Disease Is Associated With Increased Enteric Bacterial Bloodstream Infection Density in Pediatric Allogeneic Hematopoietic Cell Transplant Recipients, Clinical Infectious Diseases, May 5 2015,61(3):350-357.

Li, et al. Akkermansia Muciniphila Protects Against Atherosclerosis by Preventing Metabolic Endotoxemia-Induced Inflammation in Apoe-/- Mice. Circulation. Jun. 14, 2016;133(24):2434-46. doi: 10.1161/CIRCULATIONAHA.115.019645. Epub Apr. 25, 2016.

Liu, et al. Butyrate protects rat liver against total hepatic ischemia reperfusion injury with bowel congestion. PLoS One. Aug. 29, 2014;9(8):e106184. doi: 10.1371/journal.pone.0106184. eCollection 2014.

Lopez-Siles et al., Cultured Representatives of Two Major Phylogroups of Human Colonic *Faecalibacterium prausnitzii* Can Utilize Pectin, Uronic Acids, and Host-Derived Substrates for Growth, Applied and Environmental Microbiology, 420-428.

Lyra, et al. Comparison of bacterial quantities in left and right colon biopsies and faeces. World J Gastroenterol. Aug. 28, 2012; 18(32): 4404-4411.

Lyra, et al. Quantities of Commensal and Pathogenic Bacteria in Mucosal Biopsies of the Left and Right Colon and Feces. Gastroenterology 142.5, Suppl. 1 (May 2012): S542.

MacFarland, et al. Pharmaceutical probiotics for the treatment of anaerobic and other infections. Anaerobe. Apr.-Jun. 1997;3(2-3):73-8.

Maldonado-Gomez, et al. Stable Engraftment of Bifidobacterium longum AH1206 in the Human Gut Depends on Individualized Features of the Resident Microbiome. Cell Host Microbe. Sep. 28, 2016. pii: S1931-3128(16)30378-X. doi: 10.1016/j.chom.2016.09.001.

Man et al. The Internal Transcribed Spacer Region, A New Tool for Use in Species Differentiation and Delineation of Systematic Relationships within the Campylobacter Genus. Applied and Environmental Microbiology, May 2010, vol. 76, No. 10, p. 3071-3081. (Year: 2010).

Maslowski, et al. Regulation of inflammatory responses by gut microbiota and chemoattractant receptor GPR43. Nature. Oct. 29, 2009;461(7268):1282-6. doi: 10.1038/nature08530.

Maurer, et al. (2010). Consumption of diets high in prebiotic fiber or protein during growth influences the response to a high fat and sucrose diet in adulthood in rats. Nutr.Metab. (Lond) 7:77. doi: 10.1186/1743-7075-7-77.

Mayer, et al. Gut microbes and the brain: paradigm shift in neuroscience. J Neurosci. Nov. 12, 2014;34(46):15490-6. doi: 10.1523/JNEUROSCI.3299-14.2014.

Mayer, et al. Gut/brain axis and the microbiota. J Clin Invest. Mar. 2, 2015;125(3):926-38. doi: 10.1172/JCI76304. Epub Feb. 17, 2015.

McLean et al. Characterisation and selection of a *Lactobacillus* species to re-colonise the vagina of women with recurrent bacterial vaginosis. J. Med. Microbiol., 2000, vol. 49, pp. 543-552.

Molloy et al. The Potential Link between Gut Microbiota and IgE-Mediated Food Allergy in Early Life. Int. J. Environ. Res. Public Health 2013, 10, 7235-7256.

Muller, et al., The dynamics of genome replication using deep sequencing, Nucleic Acids Research, 2014, 42(1), e3, 11 pages. Epub Oct. 1, 2013.

Murphy, et al. Gut hormones and the regulation of energy homeostasis. Nature. Dec. 14, 2006;444(7121):854-9.

Nohr, et al. GPR41/FFAR3 and GPR43/FFAR2 as cosensors for short-chain fatty acids in enteroendocrine cells vs FFAR3 in enteric neurons and FFAR2 in enteric leukocytes. Endocrinology. Oct. 2013;154(10):3552-64. doi: 10.1210/en.2013-1142. Epub Jul. 24, 2013.

"Notice of allowance dated Jun. 29, 2015 for U.S. Appl. No. 13/780,284".

Notice of allowance dated Sep. 2, 2016 for U.S. Appl. No. 15/139,097.

Notice of allowance dated Sep. 12, 2018 for U.S. Appl. No. 14/862,663.

Notice of allowance dated Sep. 12, 2018 for U.S. Appl. No. 15/698,965.

Nylund, et al. Severity of atopic disease inversely correlates with intestinal microbiota diversity and butyrate-producing bacteria. Allergy. Feb. 2015;70(2):241-4. doi: 10.1111/all.12549.

Office action dated Feb. 7, 2017 for U.S. App. No. 15/286,218.

Office action dated Mar. 26, 2018 for U.S. App. No. 15/698,965.

"Office action dated Jun. 16, 2017 for U.S. App. No. 15/286,218".

"Office action dated Jun. 26, 2017 for U.S. App. No. 14/862,663".

Office action dated Aug. 28, 2018 for U.S. App. No. 15/271,672.

"Office action dated Dec. 14, 2016 for U.S. App. No. 14/862,663".

Office action dated Dec. 20, 2017 for U.S. App. No. 15/074,923.

O'Keefe, et al. Fat, fibre and cancer risk in African Americans and rural Africans. Nat Commun. Apr. 28, 2015;6:6342. doi: 10.1038/ncomms7342.

Ong, et al. Endogenous antimicrobial peptides and skin infections in atopic dermatitis. N Engl J Med. Oct. 10, 2002;347(15):1151-60.

Ouwehand, et al. (2005). Prebiotics and other microbial substrates for gut functionality. Curr. Opin. Biotechnol. 16, 212-217. doi: 10.1016/j.copbio.2005. 01.007.

Ouwerkerk, et al. *Akkermansia glycaniphila* sp. nov., an anaerobic mucin-degrading bacterium isolated from reticulated python faeces. Int J Syst Evol Microbiol. Nov. 2016;66(11):4614-4620. doi: 10.1099/ijsem.0.001399. Epub Aug. 5, 2016.

Pachikian, et al. (2012). Prebiotic approach alleviates hepatic steatosis: implication of fatty acid oxidative and cholesterol synthesis pathways. Mol. Nutr. Food Res. 57, 347-359. doi: 10.1002/mnfr.201200364.

(56) References Cited

OTHER PUBLICATIONS

Perez, et al. Surface Properties of Bifidobacterial Strains of Human Origin. Applied and Environmental Microbiology. vol. 64. No. 1. pp. 21-26. Jan. 1998.
Perry, et al. Acetate mediates a microbiome-brain-β-cell axis to promote metabolic syndrome. Nature. Jun. 8, 2016;534(7606):213-7. doi: 10.1038/nature18309.
Petrof et al. Stool substitute transplant therapy for the eradication of Clostridium difficile infection: "RePOOPulating" the gut. Microbiome 1(1):3 (2013).
"Plovier1, et al., A purified membrane protein from Akkermansia muciniphila or the pasteurized bacterium improves metabolism in obese and diabetic mice, nature medicine, Jan. 2017, 23(1):107-16".
Png, et al. (2010). Mucolytic bacteria with increased prevalence in IBD mucosa augment in vitro utilization of mucin by other bacteria. Am. J. Gastroenterol. 105, 2420-2428. doi: 10.1038/ajg.2010.281.
Poul, et al. Functional characterization of human receptors for short chain fatty acids and their role in polymorphonuclear cell activation. J Biol Chem. Jul. 11, 2003;278(28):25481-9. Epub Apr. 23, 2003.
"Puddu et al. Evidence for the Gut Microbiota Short-Chain Fatty Acids as Key Pathophysiological Molecules Improving Diabetes. Mediators Inflamm. vol. 2014;2014:162021. Epub Aug. 17, 2014.".
Rao, et al. A randomized, double-blind, placebo-controlled pilot study of a probiotic in emotional symptoms of chronic fatigue syndrome. Gut Pathog. Mar. 19, 2009;1(1):6. doi: 10.1186/1757-4749-1-6.
Rautava, et al., New therapeutic strategy for combating the increasing burden of allergic disease: Probiotics-A Nutrition, Allergy, Mucosal Immunology and Intestinal Microbiota (NAMI) Research Group report, J Allergy Clin Immunol, 16(1) 31-37.
Ravussin, et al. Responses of gut microbiota to diet composition and weight loss in lean and obese mice. Obesity (Silver Spring). Apr. 2012;20(4):738-47. doi: 10.1038/oby.2011.111. Epub May 19, 2011.
Ravussin. Molecular and Physiological Adaptations to Weight Perturbation in Mice. Columbia University, 2012. ProQuest Dissertations Publishing, (2012). 3475216.
Registad, et al. Gut microbes promote colonic serotonin production through an effect of short-chain fatty acids on enterochromaffin cells. FASEB J. Apr. 2015;29(4):1395-403. doi: 10.1096/fj.14-259598. Epub Dec. 30, 2014.
Roberfroid, et al. (2010). Prebiotic effects: metabolic and health benefits. Br. J. Nutr. 104, S1-S63. doi: 10.1017/S0007114510003363.
"Rogers, et al., From gut dysbiosis to altered brain function and mental illness: mechanisms and pathways, Molecular Psychiatry (2016), 21, 738-48".
Rosenfeldt et al. Effect of probiotic Lactobacillus strains in children with atopic dermatitis. J Allergy Clin Immunol 111(2):389-395 (2003).
Sahoo, et al. Boolean implication networks derived from large scale, whole genome microarray datasets. Genome Biol. Oct. 30, 2008;9(10):R157. doi: 10.1186/gb-2008-9-10-r157.
Sambrook, et al. Molecular Cloning: A Laboratory Manual. 4th Edition, 2012.
Sanmiguel, et al. Interactions between Host Factors and the Skin Microbiome. Cell. Mol. Life Sci., Dec. 2014.
Santacruz, et al., Gut microbiota composition is associated with body weight, weight gain and biochemical parameters in pregnant woman, 1Microbial Ecophysiology and Nutrition Group, pp. 1-29.
Sanz, et al. Gut microbiota and weight gain in overweight and normal weight pregnant women. Journal of Pediatric Gastroenterology and Nutrition, suppl. 3 48 (May 2009): E74.
Scheuermayer, et al. *Rubritalea marina* gen. nov., sp nov., a marine representative of the phylum 'Verrucomicrobia', isolated from a sponge (*Porifera*). Int J Syst Evol Microbiol. Sep. 2006;56(Pt 9):2119-24.
Schink, B. Energetics of syntrophic cooperation in methanogenic degradation. Microbiol Mol Biol Rev. Jun. 1997;61(2):262-80.
Segain, et al. Butyrate inhibits inflammatory responses through NFkappaB inhibition: implications for Crohn's disease. Gut. Sep. 2000;47(3):397-403.

Sáez-Lara, et al., Effects of Probiotics and Synbiotics on Obesity, Insulin Resistance Syndrome, Type 2 diabetes and Non-alcoholic Fatty Liver Disease: a Review of Human Clinical Trials, Int. J. Mol. Sci. 2016, 17, 928; doi:10.3390/ijms17060928.
Simakachorn et al., Tolerance, Safety, and Effect on the Faecal Microbiota of an Enteral Formula Supplemented With Pre- and Probiotics in Critically Ill Children, J. of Ped. Gastroenterology and Nutrition, Aug. 2011, 53(2):174-181.
Sinha, et al. Mutant WT1 is associated with DNA hypermethylation of PRC2 targets in AML and responds to EZH2 inhibition. Blood. Jan. 8, 2015;125(2):316-26. doi: 10.1182/blood-2014-03-566018. Epub Nov. 14, 2014.
Sonoyama, et al, Comparison of gut microbiota and allergic reactions in BALB/c mice fed different cultivars of rice, British Journal of Nutrition 103.2 (Jan. 28, 2010): 218-226.
Sonoyama, et al, Response of Gut Microbiota to Fasting and Hibernation in Syrian Hamsters, Applied and Environmental Microbiology 75.20 (Oct. 15, 2009): 6451-6456.
Swidsinki, et al. Acute appendicitis is characterised by local invasion with Fusobacterium nucleatum/necrophorum. Gut. Jan. 2011;60(1):34-40. doi: 10.1136/gut.2009.191320. Epub Nov. 18, 2009.
Takahashi, et al. Reduced Abundance of Butyrate-Producing Bacteria Species in the Fecal Microbial Community in Crohn's Disease. Digestion. 2016;93(1):59-65. doi: 10.1159/000441768. Epub Jan. 14, 2016.
Takaishi, et al. Imbalance in intestinal microflora constitution could be involved in the pathogenesis of inflammatory bowel disease. Int J Med Microbiol. Jul. 2008;298(5-6):463-72. Epub Sep. 25, 2007.
"Tang, et al., Endothelial TLR4 and the microbiome drive cerebral cavernous malformations cerebral cavernous malformations, Nature, May 18, 2017, 545:305-10".
Te Biesebeke, et al. Microbial Functionality in the Human Gastrointestinal Tract. Microbes and Environments 19.4:276. Japan Science and Technology Agency. (2004).
Texas Diabetes and Endocrinology Center, website information. 2016. 4 pages. http://www.texasdiabetes.com/.
The Benefits of Butyrate: More than just your average short chain fatty acid. Mar. 9, 2015. 6 pages. http://fionamilne.tumblr.com/post/113178890752/the-benefits-of-butyrate-more-than-just-your.
Thioulouse. Simultaneous analysis of a sequence of paired ecological tables: A comparison of several methods. The Annals of Applied Statistics. 2011; 2300-2325.
Thompson-Chagoyan, et al., Faecal Microbiota and Short-Chain Fatty Acid Levels in Faeces from Infants with Cow's Milk Protein Allergy, Int Arch Allergy Immunol 2011,156:325-32. Epub Jun. 29, 2011.
Tollefson, et al. Atopic Dermatitis: Skin-Directed Management. Pediatrics vol. 134, No. 6, Dec. 2014, pp. e1735-e1744.
Trajkovski, et al. Physiology: Microbial signals to the brain control weight. Nature. Jun. 8, 2016;534(7606):185-7. doi: 10.1038/534185a.
Tvede, et al. Bacteriotherapy for chronic relapsing Clostridium difficile diarrhoea in six patients. Lancet. May 27, 1989;1(8648):1156-60.
UCLA Neurobiology of Stress and Resilience Multisite Imaging, website information. 2016. 2 pages. http://uclacns.org/cores/data-core/multisite-neuroimaging/.
Val-Laillet, et al. Neuroimaging and neuromodulation approaches to study eating behavior and prevent and treat eating disorders and obesity. Neuroimage Clin. Mar. 24, 2015;8:1-31. doi: 10.1016/j.nicl.2015.03.016. eCollection 2015.
Van den Abbeele, et al, Arabinoxylans and inulin differentially modulate the mucosal and luminal gut microbiota and mucindegradation in humanized rats, Environmental Microbiology 13.10 (Oct. 2011): 2667-2680.
Van Den Abbeele, et al. Microbial Community Development in a Dynamic Gut Model Is Reproducible, Colon Region Specific, and Selective for Bacteroidetes and Clostridium Cluster IX. Appl Environ Microbiol. Aug. 2010;76(15):5237-46. doi: 10.1128/AEM.00759-10. Epub Jun. 18, 2010.

(56) References Cited

OTHER PUBLICATIONS

Van Passe, et al., The Genome of *Akkermansia muciniphila*, a Dedicated Intestinal Mucin Degrader, and Its Use in Exploring Intestinal Metagenomes, PLoS One, Mar. 2011, 6(3):e16876, 8 pages.

van Passel, et al, MetaMining of Metagenomes: Uncovering Akkermansia Diversity and Distribution, Abstracts of the General Meeting of the American Society for Microbiology 110 (2010): N-2237.

Vigsnaes, et al. Gram-negative bacteria account for main differences between faecal microbiota from patients with ulcerative colitis and healthy controls. Benef Microbes. Dec. 1, 2012;3(4):287-97. doi: 10.3920/BM2012.0018.

Vipperla, et al. Diet, microbiota, and dysbiosis: a 'recipe' for colorectal cancer. Food Funct. Apr. 20, 2016;7(4):1731-40. doi: 10.1039/c5fo01276g.

Volkow, et al. Obesity and addiction: neurobiological overlaps. Obes Rev. Jan. 2013;14(1):2-18. doi: 10.1111/j.1467-789X.2012. 01031.x. Epub Sep. 27, 2012.

Vrieze, et al. Transfer of intestinal microbiota from lean donors increases insulin sensitivity in individuals with metabolic syndrome. Gastroenterology. Oct. 2012;143(4):913-6.e7. doi: 10.1053/j.gastro.2012.06.031. Epub Jun. 20, 2012.

Wang, et al., Low Relative Abundances of the Mucolytic Bacterium *Akkermansia muciniphila* and *Bifidobacterium* Spp. In Feces of Children with Austism, Applied and Environmental Microbiology, Sep. 2011, vol. 77(18):6718-6721.

Wedlake, et al. Fiber in the treatment and maintenance of inflammatory bowel disease: a systematic review of randomized controlled trials. Inflamm Bowel Dis. Mar. 2014;20(3):576-86. doi: 10.1097/01.MIB.0000437984.92565.31.

Williams, et al. Discovery and characterization of gut microbiota decarboxylases that can produce the neurotransmitter tryptamine. Cell Host Microbe. Oct. 8, 2014;16(4):495-503. doi: 10.1016/j.chom.2014.09.001. Epub Sep. 25, 2014.

Yabe, et al. Two incretin hormones GLP-1 and GIP: comparison of their actions in insulin secretion and β cell preservation. Prog Biophys Mol Biol. Nov. 2011;107(2):248-56. doi: 10.1016/j.pbiomolbio.2011.07.010. Epub Jul. 28, 2011.

Yadav, et al. Beneficial metabolic effects of a probiotic via butyrate-induced GLP-1 hormone secretion. J Biol Chem. Aug. 30, 2013;288(35):25088-97. doi: 10.1074/jbc.M113.452516. Epub Jul. 8, 2013.

Ye. Intestinal bacteria associated with colitis and inflammatory bowel disease. University of California, Riverside, 2009. ProQuest Dissertations Publishing, (2009). 3389696.

Zeevi, et al. Personalized Nutrition by Prediction of Glycemic Responses. Cell. Nov. 19, 2015;163(5):1079-94. doi: 10.1016/j.cell. 2015.11.001.

Zeng, et al. Mechanisms linking dietary fiber, gut microbiota and colon cancer prevention. World J Gastroint Oncol. Feb. 15, 2014;6(2):41-51. doi: 10.4251/wjgo.v6.i2.41.

Zhang, et al. (2013). Human gut microbiota changes reveal the progression of glucose intolerance. Plos One 8:e71108. doi: 10.1371/journal.pone.0071108.

Zhu, et al. Constructing a Boolean implication network to study the interactions between environmental factors and OTUs. Quantitative Biology. 2014; 2(4):127-141.

Lambers; et al., "Natural Skin Surface pH is on Average Below 5, Which is Beneficial for Its Resident Flora", International Journal of Cosmetic Science, 2006, 359-370.

Office action dated Jun. 11, 2018 for U.S. Appl. No. 15/074,923.

Udayappan, et al., Oral treatment with Eubacterium hallii improves insulin sensitivity in db/db mice. NPJ Biofilms and microbiomes, vol. 2, Jul. 6, 2016; p. 16009.

Van Der Ark. Metabolic characterization and viable delivery of Akkermansia muciniphila for its future application. PhD Thesis. Wageningen University. 2018.

Allen, et al. Probiotic May Help Alleviate Stress-Related Conditions. Society for Neuroscience (SfN) 2015 Annual Meeting. Abstract 162.04. Presented Oct. 18, 2015.

Allin, et al. Aberrant intestinal microbiota in individuals with prediabetes. Diabetologia. Jan. 29, 2018. doi: 10.1007/s00125-018-4550-1. [Epub ahead of print].

American Chemical Society. "No guts no glory: Harvesting the microbiome of athletes." ScienceDaily. ScienceDaily, Aug. 20, 2017. http://www.sciencedaily.com/releases/2017/08/170820075017.htm.

"Samuel, et al., a Humanized Gnotobiotic Mouse Model of Host-Archaeal-Bacterial Mutualism, PNAS, Jun. 27, 2006, 103(26):10011-16".

Angelakis, et al. The relationship between gut microbiota and weight gain in humans. Future Microbiol. Jan. 2012;7(1):91-109. doi: 10.2217/fmb.11.142.

Ansel, Howard C, et al. Pharmaceutical Dosage Forms and Drug Delivery Systems. Philadelphia, PA: Lippincott-Williams & Wilkins, 1999. Print.

"Arora, et al., Propionate Anti-Obesity and Satiety Enhancing Factor? Appetite, Apr. 2011, 56(2):511-5".

Atlas. Handbook of Microbiological Media. Fourth Edition. CRC Press. 2010.

Ausubel, et al., (1987) Current Protocols in Molecular Biology. Wiley.

"Backhed, et al., Mechanisms underlying the resistance to diet-induced obesity in germ-free mice, PNAS, Jan. 16, 2007, 104(3):979-84".

"Backhed, et al., The gut microbiota as an environmental factor that regulates fat storage, PNAS, Nov. 2, 2004, 101(44):15718-23".

BD Diagnostics. Media Solutions for Microbial and Molecular Genetics Research Applications. Jul. 2009.

Ben-Amor, et al. Genetic diversity of viable, injured, and dead fecal bacteria assessed by fluorescence-activated cell sorting and 16S rRNA gene analysis. Appl Environ Microbiol. Aug. 2005;71(8):4679-89. doi: 10.1128/AEM.71.8.4679-4689.2005.

Bowman, et al. Analysis of Full-Length Metagenomic 16S Genes by SMRT Sequencing. American Society for Microbiology 2013 General Meeting May 19, 2013 Poster Session, pp. 116 Poster 390. Available on the internet:.

Brown, et al. Chemical synthesis and cloning of a tyrosine tRNA gene. Methods Enzymol. 1979;68:109-51.

Brun, et al. (2013). Toll-like receptor 2 regulates intestinal inflammation by controlling integrity of the enteric nervous system. Gastroenterology 145, 1323-1333. doi: 10.1053/j.gastro.2013.08.047.

Canani, et al. Potential beneficial effects of butyrate in intestinal and extraintestinal diseases. World J. Gastroenterol., Mar. 28, 2011; 17 (12): 1519-1528.

"Cani, et al., Changes in Gut Microbia Control Metabolic Endotoxemia-Induced Inflammation in High-Fat Diet-Induced Obesity and Diabetes in Mice, Diabetes, 2008, 57(6):1470-81".

Cani et al. Next-Generation Beneficial Microbes: The Case of Akkermansia muciniphila. Front Microbiol. Sep. 22, 2017;8:1765. doi: 10.3389/fmicb.2017.01765. eCollection 2017.

Chethankumar, et al. Butyric acid modulates activities of intestinal and renal disaccharidases in experimentally induced diabetic rats. Nahrung. Oct. 2002;46(5):345-8. doi: 10.1002/1521-3803(Sep. 1, 2002)46:5 345::AID-FOOD3453.0.CO;2-7.

Chin, et al. Nonhybrid, finished microbial genome assemblies from long-read SMRT sequencing data. Nat Methods. Jun. 2013;10(6):563-9. doi: 10.1038/nmeth.2474. Epub May 5, 2013.

Co-pending U.S. Appl. No. 16/159,532, filed Oct. 12, 2018.

Co-pending U.s. Appl. No. 16/431,257, filed Jun. 4, 2019.

Database GNPD [Online] MINTEL; Feb. 2015, PharmXcross: "Triple Premium Alive Probiotics", XP002779023, Database accession No. 2898253.

"De Filippo, et al., Impact of Diet in Shaping Gut Microbiota Revealed by a Comparative Study in Children From Europe and Rural Africa, PNAS, Aug. 2010, 107(33)14691-6".

Derrien, et al. (2004). *Akkermansia muciniphila* gen. nov., sp. nov., a human intestinal mucin-degrading bacterium. Int. J. Syst. Evol. Microbiol. 54(Pt 5), 1469-1476. doi: 10.1099/ijs.0.02873-0.

(56) References Cited

OTHER PUBLICATIONS

Dolfing, et al. Acetate inhibition of methanogenic, syntrophic benzoate degradation. Appl Environ Microbiol. Jul. 1988;54(7):1871-3.
Duncan, et al. Acetate Utilization and Butyryl Coenzyme A (CoA): Acetate-CoA Transferase in Butyrate-Producing Bacteria from the Human Large Intestine. Appl Environ Microbiol. Oct. 2002;68(10):5186-90.
Duncan et al. "Lactate-utilizing bacteria, isolated from human feces, that produce butyrate as a major fermentation product" Applied and environmental microbiology. 2004, vol. 70, No. 10, pp. 5810-5817.
Eid, et al. Real-time DNA sequencing from single polymerase molecules. Science. Jan. 2, 2009;323(5910):133-8. doi: 10.1126/science.1162986. Epub Nov. 20, 2008.
European search report with written opinion dated Mar. 26, 2018 for EP Application No. 15853671.
Franks, et al. Variations of bacterial populations in human feces measured by fluorescent in situ hybridization with group-specific 16S rRNA-targeted oligonucleotide probes. Appl Environ Microbiol. Sep. 1998;64(9):3336-45.
Freshney. Culture of Animal Cells: A Manual of Basic Technique and Specialized Applications. 6th Edition. 2010.
"Furet, et al., Differential Adaptation of Human Gut Microbiota to Bariatric Surgery-Induced Weight Loss: Links with Metabolic and Low-Grade Inflammation Markers, Diabetes, 2010, 59(12):3049-57".
Gennaro, A.R. "Quality Assurance and Control," from Remington: The Science and Practice of Pharmacy, 2000, Lippincott Williams & Wilkins, 20th ed., pp. 980-983.
Gregoriadis. Chapter 14: Liposomes. Drug Carriers in Biology and Medicine (57 pgs) (Academic Press, 1979).
Harmsen, et al. Extensive Set of 16S rRNA-Based Probes for Detection of Bacteria in Human Feces. Applied and Environmental Microbiology Jun. 2002, 68 (6) 2982-2990; DOI: 10.1128/AEM.68.6.2982-2990.2002.
"Hildebrandt, et al., High-Fat Diet Determines the Composition of the Murine Gut Microbiome Independently of Obesity, Gastroenterology, 2009, 137(5):1716-24 el-2".
Hjorth, et al. Pre-treatment microbial Prevotella-to- Bacteroides ratio, determines body fat loss success during a 6-month randomized controlled diet intervention, International Journal of Obesity accepted article preview Sep. 8, 2017; doi: 10.1038/ijo.2017.220.
Hold et al. 'Oligonucleotide probes that detect quantitatively significant groups of butyrate-producing bacteria in human feces.' Applied and environmental microbiology. 2003, vol. 69, No. 7, pp. 4320-4324.
Hosseini et al. Propionate as a Health-Promoting Microbial Metabolite in the Human Gut. Nutrition Reviews 69:245-258 (2010).
International search report and written opinion dated Jan. 23, 2015 for PCT Application No. US 2014/047491.
"Ismail, et al., Frequency of Firmicutes and Bacteroidetes in Gut Microbiota in Obese and Normal Weight Egyptian Children and Adults, Arch med sci., Jun. 2011, 7(3):501-7".
Jeurink, et al. (2013). Human milk: a source of more life than we imagine. Benef. Microbes 4, 17-30. doi: 10.3920/BM2012. 0040.
Kadooka, et al. Regulation of abdominal adiposity by probiotics (Lactobacillus gasseri SBT2055) in adults with obese tendencies in a randomized controlled trial. Eur J Clin Nutr. Jun. 2010;64(6):636-43. doi: 10.1038/ejcn.2010.19. Epub Mar. 10, 2010.
"Kallus, et al., the Intestinal Microbiota and Obesity, J. Clin. Gastroenterol, Jan. 2012, 46(1):16-24".
Khan, et al. Antioxidants keep the potentially probiotic but highly oxygen-sensitive human gut bacterium *Faecalibacterium prausnitzii* alive at ambient air. PLoS One. May 5, 2014;9(5):e96097. doi: 10.1371/journal.pone.0096097. eCollection 2014.
"Kootte, et al., the Therapeutic Potential of Manipulating Gut Microbiota in Obesity and Type 2 Diabetes Mellitus, Diabetes, Obesity and Metabolism, Epub 2011, 14:112-120".
Lange, Vinzenz et al. Selected reaction monitoring for quantitative proteomics: a tutorial. Molecular Systems Biology 4(222):1-14 (Oct. 14, 2008).
Larsen, et al. Gut Microbiota in Human Adults with Type 2 Diabetes Differs from Non-Diabetic Adults. PLoS One. Feb. 5, 2010;5(2):e9085. doi: 10.1371/journal.pone.0009085.
"Lefebvre, et al., Role of Bile Acids and Bile Acid Receptors in Metabolic Regulation, Physiol Rev, 2009, 89(1):147-91".
"Ley, et al., Microbial Ecology: Human Gut Microbes Associated With Obesity, Nature, Dec. 21, 2006, 444:1022-3".
"Ley, et al., Obesity Alters Gut Microbial Ecology, PNAS, Aug. 2, 2005, 102(31):11070-5".
Ley et al., Obesity alters gut microbial ecology. Proc Natl Acad Sci U S A, 102:11070-11075, 2005.
"Li et al., Metabolic Surgery Profoundly Influences Gut Microbial-Host Metabolic Cross-Talk, Gut, 2011; 60(9):1214-23".
Liou, et al. Conserved shifts in the gut microbiota due to gastric bypass reduce host weight and adiposity. Sci Transl Med. Mar. 27, 2013;5(178):178ra41. doi: 10.1126/scitranslmed.3005687.
"Louis et al. Diversity, metabolismand microbial ecology of butyrate-producing bacteria from the human large intestine. FEMS Microbiol Lett. 2009, vol. 294(1), p. 1-8.".
McPherson, et al. eds. PCR 2: a practical approach. Oxford University Press. 1995.
Mekkes, et al. The development of probiotic treatment in obesity: a review. Beneficial MICR, Wageningen Academic Publishes, NL, vol. 5, No. 1, Mar. 1, 2014, pp. 19-28.
Meneghin, et al. Probiotics and atopic dermatitis in children. Pharmaceuticals (Basel). Jul. 6, 2012;5(7):727-44. doi: 10.3390/ph5070727.
"Messaoudi, et al. Assessment of psychotropic-like properties of a probiotic formulation (Lactobacillus helveticus R0052 and Bifidobacterium longum R0175) in rats and human subjects. Br J Nutr. Mar. 2011;105(5):755-64. doi: 10.1017/S0007114510004319. Epub Oct. 26, 2010.".
Millon, et al. Comparative meta-analysis of the effect of *Lactobacillus* species on weight gain in humans and animals. Microb Pathog. Aug. 2012;53(2):100-8. doi: 10.1016/j.micpath.2012.05.007. Epub May 24, 2012.
Munoz-Tamayo, et al. Kinetic modelling of lactate utilization and butyrate production by key human colonic bacterial species. FEMS Microbiol. Ecol., 76 (2011), 615-624 DOI:10.1111/j.1574-6941.2011.01085.x.
"Naito, et al., Beneficial Effect of Oral Administration of Lactobacillus Casei Strain Shirota on Insulin Resistance in Diet-Induced Obesity Mice, J. appl. microbial., Mar. 2011, 110(3):650-7".
Narang, et al. Improved phosphotriester method for the synthesis of gene fragments. Methods Enzymol. 1979;68:90-8.
"Naruszewicz, et al. Effect of Lactobacillus plantarum 299v on cardiovascular disease risk factors in smokers. Am J Clin Nutr. Dec. 2002;76(6):1249-55.".
"Navarro-Noya, et al., Bacterial Communities Associated With the Rhizosphere of Pioneer Plants (*Bahia xylopoda* and *Viguiera linearis*) Growing on Heavy Metals-Contaminated Soils, Antonievan Leeuwenhoek, 2010, 97:335-49".
Nilsson, et al. A Cereal-Based Evening Meal Rich in Indigestible Carbohydrates Increases Plasma Butyrate the Next Morning. J Nutr. Nov. 2010;140(11):1932-6. doi: 10.3945/jn.110.123604. Epub Sep. 1, 2010.
Office action dated Apr. 4, 2019 for U.S. Appl. No. 16/159,524.
Office action dated May 10, 2019 for U.S. Appl. No. 15/271,672.
Office action dated Nov. 27, 2017 for U.S. Appl. No. 15/286,218.
Oh, et al. Shifts in Human Skin and Nares Microbiota of Healthy Children and Adults. Genome Medicine 2012, 4:77.
"Parnell, et al. Weight loss during oligofructose supplementation is associated with decreased ghrelin and increased peptide YY in overweight and obese adults. Am J Clin Nutr. Jun. 2009;89(6):1751-9. doi: 10.3945/ajcn.2009.27465. Epub Apr. 22, 2009.".
"Patti, et al., Serum Bile Acids Are Higher in Humans with Prior Gastric Bypass: Potential Contribution to Improved Glucose and Lipid Metabolism, Obesity (silver spring), 2009, 17(9): 1671-7".
"Speakman, et al., Revised Equations for Calculating C02 Production From Doubly Labeled Water in Humans, Am J. physiol., Jun. 1993, pp. e912-7".
"Queipo-Ortuno, et al. Gut microbiota composition in male rat models under different nutritional status and physical activity and its

(56) References Cited

OTHER PUBLICATIONS association with serum leptin and ghrelin levels. PLoS One. May 28, 2013;8(5):e65465. doi: 10.1371/journal.pone.0065465. Print 2013.".
Rajilic-Stojanovic, et al. Diversity of the human gastrointestinal tract microbiota revisited. Environ Microbiol. Sep. 2007;9(9):2125-36. doi: 10.1111/j.1462-2920.2007.01369.x.
Ridacom. "Plant Based Media." RIDACOM—Comprehensive Bioscience Supplier—Plant Based Media, 2019, ridacom.com/en/product-list/353/Plant-based-media.
Roelofsen, et al. The interaction of short-chain fatty acids with adipose tissue: relevance for prevention of type 2 diabetes. Benef Microbes. Nov. 2010;1(4):433-7. doi: 10.3920/BM2010.0028.
"Roshchina, V. Evolutionary Considerations of Neurotransmitters in Microbial, Plant, and Animal Cells. In: Lyte M, Fitzgerald P (eds). Microbial Endocrinology: Interkingdom Signaling in Infectious Disease and Health. New York: Springer, Feb. 2010, pp. 17-52.".
"Roy, et al., Gut Microbiota Transplantation Demonstrates Its Causal Role in the Development of Type 2 Diabetes and Fatty Liver, Oral Presentations, Journal of Hepatology, 2012, vol. 56, S23.".
"Rubino, et al., Metabolic Surgery to Treat Type 2 Diabetes: Clinical Outcomes and Mechanisms of Action, Annu. rev. med., 2010, 61:393-411".
Saleem, et al. Screening of Various Plant Based Extracts for Their Suitability to Be Used as Growth Promoting Substances in the Preparation of Culture Media for Fungi. 114th General Meeting of the American Society for Microbiology. Conference abstracts. 2014.
Santacruz, et al. Gut microbiota composition is associated with body weight, weight gain and biochemical parameters in pregnant women. Br J Nutr. Jul. 2010;104(1):83-92. doi: 10.1017/S0007114510000176. Epub Mar. 8, 2010.
Seki, et al. Prevention of antibiotic-associated diarrhea in children by Clostridium butyricum Miyairi. Pediatr Int. Feb. 2003;45(1):86-90.
Sokol, et al. Faecalibacterium prausnitzii is an anti-inflammatory commensal bacterium identified by gut microbiota analysis of Crohn disease patients. Proc Natl Acad Sci U S A. Oct. 28, 2008;105(43):16731-6. doi: 10.1073/pnas.0804812105. Epub Oct. 20, 2008.
Hakansson, et al. Gut microbiota and inflammation. Nutrients. Jun. 2011;3(6):637-82. doi: 10.3390/nu3060637. Epub Jun. 3, 2011.
HiVeg Peptone, Technical Data Sheet, 2019 (Year: 2019).
Office action dated May 31, 2019 for U.S. Appl. No. 16/159,536.
Office action dated Jun. 5, 2019 for U.S. Appl. No. 16/159,537.
Sanz, et al. Insights into the Roles of Gut Microbes in Obesity, Hindawi Publishing Corporation, vol. 2008, Article ID 829101, 9 Pages.
Senevirathne. Effect of Resistant Starch on Microbial Content of the Intestinal Tract. LSU Doctoral Dissertations. 2717. digitalcommons.lsu.edu/gradschool_dissertations/2717.
Wolever, et al. Do colonic short-chain fatty acids contribute to the long-term adaptation of blood lipids in subjects with type 2 diabetes consuming a high-fiber diet?. Am J Clin Nutr. Jun. 2002;75(6):1023-30. DOI: 10.1093/ajcn/75.6.1023.
"Thaler, at al., Minireview: Hormonal and Metabolic Mechanisms of Diabetes Remission After Gastrointestinal Surgery, Endocrinology, 2009, 150(6):2518-25".
"Thomas, et al., Tgr5- Mediated Bile Acid Sensing Controls Glucose Homeostasis, Cell Metab, 2009, 10(3):167-77".
"Turnbaugh, et al., a Core Gut Microbiome in Obese and Lean Twins, Nature, 2009, 457(7228):480-4".
"Turnbaugh, et al., an Obesity-Associated Gut Microbiome with Increased Capacity for Energy Harvest, Nature, Dec. 2006, 444:1027-31".
"Turnbaugh, et al., The Effect of Diet on the Human Gut Microbiome: A Metagenomic Analysisin Humanized Gnotobiotic Mice, Sci. Transl. Med, 2009, 1(6):6ra14".
"Stylopoulos, et al., Roux-En-Y Gastric Bypass Enhances Energy Expenditure and Extends Lifespan in Diet-Induced Obese Rats, Obesity, Oct. 2009, 17(10):1839-47".

Vital et al. Revealing the bacterial butyrate synthesis pathways by analyzing (meta)genomic data. mBIO 5(2):e00889-14.
"Vuong, et al., How the Microbiome Affects Cognition, Mood and Behavior, Abstract, Available at http://www.prohealth.com/library/showarticle.cfm?libid=30495, Accessed on Jul. 13, 2017".
"Swann, et al., Systemic Gut Microbial Modulation of Bile Acid Metabolism in Host Tissue Compartments, PNAC, Mar. 15, 2011, 108(11):4523-30".
Ward, et al. (2013). Human milk metagenome: a functional capacity analysis. BMC Microbiol. 13:116. doi: 10.1186/1471-2180-13-116.
"Watanabe, et al., Bile acids induce energy expenditure by promoting intracellular thyroid hormone activation, Nature, Jan. 26, 2006, 439:484-9".
"Wikoffa, et al., Metabolomics analysis reveals large effects of gut microflora on mammalian blood metabolites, PNAS, Mar. 10, 2009, 106(10):3698-3703".
"Woodard, et al., Probiotics Improve Outcomes After Roux-En-Y Gastric Bypass Surgery: A Prospective Randomized Trial, J Gastrointest Surg, Jul. 2009, 13:1198-1204".
Youssef, et al. Plant-based culture media: Efficiently support culturing rhizobacteria and correctly mirror their in-situ diversity. J Adv Res. Mar. 2016;7(2):305-16. doi: 10.1016/j.jare.2015.07.005. Epub Aug. 29, 2015.
Zhang, et al. Human gut microbiota in obesity and after gastric bypass. Proc Natl Acad Sci U S A. Feb. 17, 2009;106(7):2365-70. doi: 10.1073/pnas.0812600106. Epub Jan. 21, 2009.
Zhu, et al. Gut microbiome and nonalcoholic fatty liver diseases. Pediatr Res. Jan. 2015;77(1-2):245-51. doi: 10.1038/pr.2014.157. Epub Oct. 13, 2014.
Zoetendal, et al. Temperature Gradient Gel Electrophoresis Analysis of 16S rRNA from Human Fecal Samples Reveals Stable and Host-Specific Communities of Active Bacteria. Appl Environ Microbiol. Oct. 1998; 64(10): 3854-3859.
Barcenilla, et al. Phylogenetic relationships of butyrate-producing bacteria from the human gut. Appl Environ Microbiol. Apr. 2000 66(4):1654-61.
Beye, et al. Careful use of 16S rRNA gene sequence similarity values for the identification of *Mycobacterium* species. New Microbes New Infect. Dec. 29, 2017;22:24-29. doi: 10.1016/j.nmni.2017.12.009. eCollection Mar. 2018.
Bouter, et al. Differential metabolic effects of oral butyrate treatment in lean versus metabolic syndrome subjects. Clin Transl Gastroenterol. May 25, 2018. 9(5):155. doi: 10.1038/s41424-018-0025-4.
Eckburg, PB. et al., Diversity of the human intestinal microbial flora.Science. Jun. 10, 2005;308(5728):1635-8. Epub Apr. 14, 2005.
Edgar, R.C. Updating the 97% identity threshold for 16S ribosomal RNA OTUs. Bioinformatics. Jul. 15, 2018;34(14):2371-2375. doi: 10.1093/bioinformatics/bty113.
Hold, et al. Assessment of microbial diversity in human colonic samples by 16S rDNA sequence analysis. FEMS Microbiol Ecol. Jan. 1, 2002. 39(1):33-9. doi: 10.1111/j.1574-6941.2002.tb00904.x.
Notice of Allowance dated Jan. 13, 2020 for U.S. Appl. No. 15/271,672.
Obata, et al. Indigenous opportunistic bacteria inhabit mammalian gut-associated lymphoid tissues and share a mucosal antibody-mediated symbiosis. Proc Natl Acad Sci USA. Apr. 20, 2010. 107(16):7419-24. doi: 10.1073/pnas.1001061107. Epub Apr. 1, 2010.
Office action dated Sep. 18, 2019 for U.S. Appl. No. 16/159,524.
Rajilic-Stojanovic, et al. Development and application of the human intestinal tract chip, a phylogenetic microarray: analysis of universally conserved phylotypes in the abundant microbiota of young and elderly adults. Environ Microbiol. Jul. 2009 11(7):1736-51. doi: 10.1111/j.1462-2920.2009.01900.x. Epub Mar. 11, 2009.
Rossi-Tamisier, et al. Cautionary tale of using 16S rRNA gene sequence similarity values in identification of human-associated bacterial species. Int J Syst Evol Microbiol. Jun. 2015;65(Pt 6):1929-34. doi: 10.1099/ijs.0.000161. Epub Mar. 3, 2015.
Stevenson, et al., New strategies for cultivation and detection of previously uncultured microbes. Appl Environ Microbiol. Aug. 2004;70(8):4748-55.

(56) References Cited

OTHER PUBLICATIONS

Tolhurst, et al. Short-chain fatty acids stimulate glucagon-like peptide-1 secretion via the G-protein-coupled receptor FFAR2. Diabetes. Feb. 2012;61(2):364-71. doi: 10.2337/db11-1019. Epub Dec. 21, 2011.
U.S. Appl. No. 15/271,672 Office Action dated Oct. 31, 2019.
U.S. Appl. No. 15/286,218 Office Action dated Oct. 16, 2019.
U.S. Appl. No. 16/159,536 Office Action dated Oct. 31, 2019.
U.S. Appl. No. 16/159,537 Office Action dated Dec. 13, 2018.
U.S. Appl. No. 16/159,537 Office Action dated Oct. 31, 2019.
Van Baarlen, et al. Differential NF-κb pathways induction by Lactobacillus plantarum in the duodenum of healthy humans correlating with immune tolerance. Proc Natl Acad Sci U S A. Feb. 17, 2009. 106(7):2371-6. doi: 10.1073/pnas.0809919106. Epub Feb. 3, 2009.
Vrieze, et al. The environment within: how gut microbiota may influence metabolism and body composition. Diabetologia. Apr. 2010. 53(4):606-13. doi: 10.1007/s00125-010-1662-7. Epub Jan. 26, 2010.
Co-pending U.S. Appl. No. 16/830,972, filed Mar. 26, 2020.
Co-pending U.S. Appl. No. 16/830,995, filed Mar. 26, 2020.
Notice of Allowance dated Feb. 19, 2020 for U.S. Appl. No. 15/271,672.
Notice of allowance dated Feb. 21, 2020 for U.S. Appl. No. 16/159,536.
Office action dated Mar. 5, 2020 for U.S. Appl. No. 16/159,524.
U.S. Appl. No. 15/286,218 Office Action dated Feb. 21, 2020.
Lukovac, et al. Differential Modulation by Akkermansia muciniphila and Faecalibacterium prausnitzii of Host Peripheral Lipid Metabolism and Histone Acetylation in Mouse Gut Organoids. mBio. Jul.-Aug. 2014; 5(4): e01438-14. Published online Aug. 12, 2014. doi: 10.1128/mBio.01438-14.

\* cited by examiner

Exemplary Dx/Rx for:

- Preterm Labor Dx/Rx
- Chronic Fatigue Syndrome
- Skin Health Cosmetic
- Type 2 Diabetes Mellitus (T2DM)

(A) Standard Resolution

US 10,842,830 B2

METHODS AND COMPOSITIONS RELATING TO MICROBIAL TREATMENT AND DIAGNOSIS OF DISORDERS

CROSS REFERENCE

This application is a continuation of U.S. application Ser. No. 15/271,672, filed Sep. 21, 2016, which is a continuation of U.S. application Ser. No. 15/139,097, filed Apr. 26, 2016, now U.S. Pat. No. 9,486,487, which is a continuation of PCT Application No. PCT/US15/58511, filed Oct. 30, 2015, which claims the benefit of U.S. Provisional Application Ser. No. 62/073,912, filed Oct. 31, 2014, all of which are incorporated herein by reference in their entirety.

BACKGROUND OF THE INVENTION

The body of an individual is inhabited by trillions of microbes across various locations, often referred to as microbiomes. Microbiomes can play a key role in many health conditions and diseases. Despite the interrelation between microbiomes and health, the complexity of the various microbiomes, as well as difficulties in characterizing, categorizing, and analyzing microbiome constituents has made understanding microbiomes challenging. Consequently, these challenges have presented hurdles in the development of diagnostic and therapeutic applications for microbiome-related health conditions and diseases. The present disclosure provides methods, systems, compositions, and kits to address the need for microbiome-related treatment of health conditions and disease.

SEQUENCE LISTING

The instant application contains a Sequence Listing which has been submitted in ASCII format via EFS-Web and is hereby incorporated by reference in its entirety. Said ASCII copy, created on Sep. 21, 2016, is named 46790-702.302.txt and is 36,254,267 bytes in size.

BIOLOGICAL DEPOSITS

This application contains a reference to a deposit of biological material. The following biological materials have been deposited with the American Type Culture Collection (ATCC), in Manassas, Va., and bear the following designations, accession numbers and dates of deposit: *Clostridium beijerinckii*; WB-STR-0005 (PTA-123634, deposited Dec. 14, 2016); *Clostridium butyricum*; WB-STR-0006 (PTA-123635, deposited Dec. 14, 2016).

SUMMARY OF THE INVENTION

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe that alters glucagon-like peptide-1 (GLP-1) production, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe that encodes for an enzyme selected from the group consisting of: butyrate kinase, butyrate coenzyme A, butyrate coenzyme a transferase, and any combination thereof, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe that is capable of producing butyrate, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Akkermansia muciniphilia*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Anaerostipes caccae*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Bifidobacterium adolescentis*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Bifidobacterium bifidum*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Bifidobacterium infantis*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Bifidobacterium longum*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Butyrivibrio fibrisolvens*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Clostridium acetobutylicum*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Clostridium beijerinckii*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Clostridium butyricum*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Clostridium colinum*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Clostridium indolis*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Enterococcus faecium*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Eubacterium hallii*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Eubacterium rectale*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Faecalibacterium prausnitzii*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Fibrobacter succinogenes*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Lactobacillus acidophilus*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Lactobacillus brevis*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Lactobacillus bulgaricus*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Lactobacillus casei*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Lactobacillus caucasicus*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Lactobacillus fermentum*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Lactobacillus helveticus*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Lactobacillus lactis*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Lactobacillus plantarum*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Lactobacillus reuteri*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Lactobacillus rhamnosus*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Roseburia cecicola*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Roseburia inulinivorans*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Ruminococcus flavefaciens*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Ruminococcus gnavus*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Streptococcus cremoris*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Streptococcus faecium*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Streptococcus infantis*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Streptococcus mutans*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Streptococcus thermophilus*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Clostridium aminophilum*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Clostridium orbiscindens*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Oscillospira guilliermondii*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Ruminococcus obeum*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Anaerofustis stercorihominis*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Anaerostipes hadrus*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Anaerotruncus colihominis*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Clostridium sporogenes*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Clostridium tetani*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Coprococcus*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Coprococcus eutactus*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Eubacterium cylindroides*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Eubacterium dolichum*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Eubacterium ventriosum*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Roseburia faeccis*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Roseburia hominis*, and a pharmaceutically-acceptable carrier.

In some embodiments, this invention comprises a method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of *Roseburia intestinalis*, and a pharmaceutically-acceptable carrier.

A method of treating a metabolic disorder in a subject in need thereof, the method comprising: administering a therapeutically-effective amount of a pharmaceutical composition comprising a population of isolated and purified microbe, wherein at least one of said microbes comprises a microbe with at least about 85% sequence identity to a rRNA sequence of a microbe selected from the group consisting of: *Akkermansia muciniphila, Anaerostipes caccae, Bifidobacterium adolescentis, Bifidobacterium bifidum, Bifidobacterium infantis, Bifidobacterium longum, Butyrivibrio fibrisolvens, Clostridium acetobutylicum, Clostridium aminophilum, Clostridium beijerinckii, Clostridium butyricum, Clostridium colinum, Clostridium indolis, Clostridium orbiscindens, Enterococcus faecium, Eubacterium hallii, Eubacterium rectale, Faecalibacterium prausnitzii, Fibrobacter succinogenes, Lactobacillus acidophilus, Lactobacillus brevis, Lactobacillus bulgaricus, Lactobacillus casei, Lactobacillus caucasicus, Lactobacillus fermentum, Lactobacillus helveticus, Lactobacillus lactis, Lactobacillus plantarum, Lactobacillus reuteri, Lactobacillus rhamnosus, Oscillospira guilliermondii, Roseburia cecicola, Roseburia inulinivorans, Ruminococcus flavefaciens, Ruminococcus gnavus, Ruminococcus obeum, Streptococcus cremoris, Streptococcus faecium, Streptococcus infantis, Streptococcus mutans, Streptococcus thermophilus, Anaerofustis stercorihominis, Anaerostipes hadrus, Anaerotruncus colihominis, Clostridium sporogenes, Clostridium tetani, Coprococcus, Coprococcus eutactus, Eubacterium cylindroides, Eubacterium dolichum, Eubacterium ventriosum, Roseburia faeccis, Roseburia hominis, Roseburia intestinalis*, and any combination thereof.

The method of any of the preceding embodiments, wherein said treating results in a subject with an altered microbiome.

The method of any of the preceding embodiments, wherein said treating results in a subject with an altered gut microbiome.

The method of any of the preceding embodiments, wherein the pharmaceutical composition further comprises a second population of isolated and purified microbe. In some aspects, the method may further comprise a second population of isolated and purified microbe, wherein said second population comprises a microbe with at least about 85% sequence identity to a rRNA sequence of a microbe selected from the group consisting of: *Akkermansia muciniphila, Anaerostipes caccae, Bifidobacterium adolescentis, Bifidobacterium bifidum, Bifidobacterium infantis, Bifidobacterium longum, Butyrivibrio fibrisolvens, Clostridium acetobutylicum, Clostridium aminophilum, Clostridium beijerinckii, Clostridium butyricum, Clostridium colinum, Clostridium indolis, Clostridium orbiscindens, Enterococcus faecium, Eubacterium hallii, Eubacterium rectale, Faecalibacterium prausnitzii, Fibrobacter succinogenes, Lactobacillus acidophilus, Lactobacillus brevis, Lactobacillus bulgaricus, Lactobacillus casei, Lactobacillus caucasicus, Lactobacillus fermentum, Lactobacillus helveticus, Lactobacillus lactis, Lactobacillus plantarum, Lactobacillus reuteri, Lactobacillus rhamnosus, Oscillospira guilliermondii, Roseburia cecicola, Roseburia inulinivorans, Ruminococcus flavefaciens, Ruminococcus gnavus, Ruminococcus obeum, Streptococcus cremoris, Streptococcus faecium, Streptococcus infantis, Streptococcus mutans, Streptococcus thermophilus, Anaerofustis stercorihominis, Anaerostipes hadrus, Anaerotruncus colihominis, Clostridium sporogenes, Clostridium tetani, Coprococcus, Coprococcus eutactus, Eubacterium cylindroides, Eubacterium dolichum, Eubacterium ventriosum, Roseburia faeccis, Roseburia hominis, Roseburia intestinalis*, and any combination thereof.

The method of any of the preceding embodiments, wherein said metabolic disorder is obesity.

The method of any of the preceding embodiments, wherein said metabolic disorder is insulin insensitivity.

The method of any of the preceding embodiments, wherein said metabolic disorder is Type 2 Diabetes Mellitus.

The method of any of the preceding embodiments, wherein said treating results in the subject losing weight as compared to a pre-treatment level.

The method of any of the preceding embodiments, wherein said treating results in the subject having increased insulin sensitivity as compared to a pre-treatment level.

The method of any of the preceding embodiments, wherein said treating results in the subject having reduced symptoms associated with the metabolic disorder as compared to a pre-treatment level.

The method of any of the preceding embodiments, wherein said subject is a subject enrolled in a clinical study.

The method of any of the preceding embodiments, wherein said at least about 85% sequence identity is selected from the group consisting of: at least about 96%, at least about 97%, at least about 98%, at least about 99%, at least about 99.5%, and at least about 99.5% sequence identity to a rRNA sequence.

The method of any of the preceding embodiments, wherein said pharmaceutical composition is substantially free of fecal matter obtained from a subject.

The method of any of the preceding embodiments, wherein said at least one of said microbes comprises a population of said microbes.

The method of any of the preceding embodiments, wherein said rRNA sequence is a 16S rRNA sequence.

The method of any of the preceding embodiments, wherein said rRNA sequence is a 23S rRNA sequence.

The method of any of the preceding embodiments, wherein said rRNA sequence is both a 16S rRNA sequence and a 23S rRNA sequence.

The method of any of the preceding embodiments, wherein the pharmaceutical composition is formulated for oral delivery.

The method of any of the preceding embodiments, wherein the pharmaceutical composition is formulated for anal delivery.

The method of any of the preceding embodiments, wherein the pharmaceutical composition is formulated as a pill.

The method of any of the preceding embodiments, wherein the pharmaceutical composition is formulated as a capsule.

The method of any of the preceding embodiments, wherein the pharmaceutical composition is formulated in a liquid form suitable for administration via an enema.

The method of any of the preceding embodiments, wherein the pharmaceutical composition is formulated as a suppository.

The method of any of the preceding embodiments, wherein the pharmaceutical composition is formulated in a liquid form suitable for delivery via injection.

The method of any of the preceding embodiments, wherein the pharmaceutical composition further comprises a probiotic. In some aspects, the pharmaceutical composition may further comprise a probiotic, said probiotic is selected from the group consisting of: *Akkermansia muciniphila, Anaerostipes caccae, Bifidobacterium adolescentis, Bifidobacterium bifidum, Bifidobacterium infantis, Bifidobacterium longum, Butyrivibrio fibrisolvens, Clostridium acetobutylicum, Clostridium aminophilum, Clostridium beijerinckii, Clostridium butyricum, Clostridium colinum, Clostridium indolis, Clostridium orbiscindens, Enterococcus faecium, Eubacterium hallii, Eubacterium rectale, Faecalibacterium prausnitzii, Fibrobacter succinogenes, Lactobacillus acidophilus, Lactobacillus brevis, Lactobacillus bulgaricus, Lactobacillus casei, Lactobacillus caucasicus, Lactobacillus fermentum, Lactobacillus helveticus, Lactobacillus lactis, Lactobacillus plantarum, Lactobacillus reuteri, Lactobacillus rhamnosus, Oscillospira guilliermondii, Roseburia cecicola, Roseburia inulinivorans, Ruminococcus flavefaciens, Ruminococcus gnavus, Ruminococcus obeum, Streptococcus cremoris, Streptococcus faecium, Streptococcus infantis, Streptococcus mutans, Streptococcus thermophilus, Anaerofustis stercorihominis, Anaerostipes hadrus, Anaerotruncus colihominis, Clostridium sporogenes, Clostridium tetani, Coprococcus, Coprococcus eutactus, Eubacterium cylindroides, Eubacterium dolichum, Eubacterium ventriosum, Roseburia faeccis, Roseburia hominis, Roseburia intestinalis*, and any combination thereof.

The method of any of the preceding embodiments, wherein the pharmaceutical composition further comprises a prebiotic. In some aspects, the pharmaceutical composition may further comprise a prebiotic, said prebiotic is selected from the group consisting of: complex carbohydrates, complex sugars, resistant dextrins, resistant starch, amino acids, peptides, nutritional compounds, biotin, polydextrose, fructooligosaccharide (FOS), galactooligosaccharides (GOS), inulin, starch, lignin, *psyllium*, chitin, chitosan, gums (e.g. guar gum), high amylose cornstarch (HAS), cellulose, β-glucans, hemi-celluloses, lactulose, mannooligosaccharides, mannan oligosaccharides (MOS), oligofructose-enriched inulin, oligofructose, oligodextrose, tagatose, trans-galactooligosaccharide, pectin, resistant starch, xylooligosaccharides (XOS), and any combination thereof. In some aspects, said prebiotic is inulin.

The method of any of the preceding embodiments, wherein the pharmaceutical composition is co-administered with an antibiotic.

The method of any of the preceding embodiments, wherein the pharmaceutical composition is administered after an antibiotic. In some aspects, the method may comprise administering the pharmaceutical composition after an antibiotic, wherein the pharmaceutical composition is administered at least one hour after an antibiotic. In some aspects, the method may comprise administering the pharmaceutical composition after an antibiotic, wherein the pharmaceutical composition is administered at least 2 hours after an antibiotic. In some aspects, the method may comprise administering the pharmaceutical composition after an antibiotic, wherein the pharmaceutical composition is administered at least 12 hours after an antibiotic. In some aspects, the method may comprise administering the pharmaceutical composition after an antibiotic, wherein the pharmaceutical composition is administered at least 1 day after an antibiotic. In some aspects, the method may comprise administering the pharmaceutical composition after an antibiotic, wherein the pharmaceutical composition is administered at least 1 week after an antibiotic. In some aspects, the method may comprise administering the pharmaceutical composition after an antibiotic, wherein the pharmaceutical composition is administered at least 2 weeks after an antibiotic.

The method of any of the preceding embodiments, wherein the pharmaceutical composition is administered after completion of an antibiotic regimen by the subject.

The method of any of the preceding embodiments, wherein the pharmaceutical composition is formulated as a dietary supplement.

The method of any of the preceding embodiments, wherein the pharmaceutical composition is a biologic product.

The method of any of the preceding embodiments, further comprising determining the sequence of a population of the subject's microbiome by sequencing. In some aspects, the method may further comprise determining the sequence of the subject's microbiome by sequencing, said sequencing comprises sequencing the 16S rRNA. In some aspects, the method may further comprise determining the sequence of the subject's microbiome by sequencing, said sequencing comprises sequencing the 23S rRNA. In some aspects, the method may further comprise determining the sequence of the subject's microbiome by sequencing, said sequencing comprises sequencing the 23S and 16S rRNA. In some aspects, the method may further comprise determining the sequence of the subject's microbiome by sequencing, said sequencing comprises Complete Biome Test resolution. In some aspects, said sequencing comprises long-read sequencing. In some aspects, the method may further comprise determining the sequence of the subject's microbiome by sequencing, wherein the determining the sequence of the population of the subject's microbiome is performed before treating the subject with the pharmaceutical composition. In some aspects, the method may further comprise determining the sequence of the subject's microbiome by sequencing, wherein the determining the sequence of the population of the subject's microbiome is performed after treating the subject with the pharmaceutical composition.

The method of any of the preceding embodiments, further comprising transmitting data via machine-readable code.

The method of any of the preceding embodiments, further comprising computing data via machine-readable code.

The method of any of the preceding embodiments, further comprising storing data via machine-readable code.

The method of any of the preceding embodiments, wherein the subject is a mammal.

The method of any of the preceding embodiments, wherein the subject is a laboratory mammal.

The method of any of the preceding embodiments, wherein the subject is a human.

The method of any of the preceding embodiments, wherein said method further comprises a companion diagnostic.

A method of producing the microbes of any of the preceding embodiments, the method comprising genetically-modifying the microbes to generate recombinant microbes. In some aspects, the method may comprise genetically-modifying the microbes to generate recombinant microbes, wherein an operon controls growth of the recombinant microbe.

The method of any of the preceding embodiments, wherein the pharmaceutical composition is formulated as an enteric-coated pill. In some aspects, the method may comprise formulating the pharmaceutical composition as an enteric-coated pill, wherein the enteric-coating is formed by a pH sensitive polymer. In some aspects, the method may comprise formulating the pharmaceutical composition as an enteric-coated pill, wherein the enteric-coating is formed by a pH sensitive polymer, wherein the polymer is eudragit FS30D.

The method of any of the preceding embodiments, wherein the pharmaceutical composition is formulated for delivery of the microbes to the subject's ileum region.

The method of any of the preceding embodiments, wherein the pharmaceutical composition is formulated for delivery of the microbes to the subject's colon region.

The method of any of the preceding embodiments, wherein the pharmaceutical composition is formulated for delivery of the microbes to the subject's ileum and colon region.

The method of any of the preceding embodiments, wherein the pharmaceutical composition is delivered to the subject's ileum region.

The method of any of the preceding embodiments, wherein the pharmaceutical composition is delivered to the subject's colon region.

The method of any of the preceding embodiments, wherein the pharmaceutical composition is delivered to the subject's ileum and colon region.

The method of any of the preceding embodiments, wherein the pharmaceutical composition is administered before food intake. In some aspects, the method may comprise administering the pharmaceutical composition before food intake, wherein the pharmaceutical composition is administered at least one hour before food intake. In some aspects, the method may comprise administering the pharmaceutical composition before food intake, wherein the pharmaceutical composition is administered at least 2 hours before food intake. In some aspects, the method may comprise administering the pharmaceutical composition before food intake, wherein the pharmaceutical composition is administered at least 3 hours before food intake. In some aspects, the method may comprise administering the pharmaceutical composition before food intake, wherein the pharmaceutical composition is administered at least 4 hours before food intake.

The method of any of the preceding embodiments, wherein said microbes are administered with food intake.

The method of any of the preceding embodiments, wherein said microbes comprise a synergistic stability in the pharmaceutical composition as compared to individual strains.

INCORPORATION BY REFERENCE

All publications, patents, and patent applications mentioned in this specification are herein incorporated by reference to the same extent as if each individual publication, patent, or patent application was specifically and individually indicated to be incorporated by reference.

The content of the International Nucleotide Sequence Database Collaboration (DDBJ/EMBL/GENBANK) accession number CP001071.1 for microbial strain *Akkermansia muciniphila*, culture collection ATCC BAA-835, is herein incorporated by reference in its entirety.

The content of DDBJ/EMBL/GENBANK accession number AJ518871.2 for microbial strain *Anaerofustis stercorihominis*, culture collection DSM 17244, is herein incorporated by reference in its entirety.

The content of DDBJ/EMBL/GENBANK accession number DS499744.1 for microbial strain *Anaerostipes caccae*, culture collection DSM 14662, is herein incorporated by reference in its entirety.

The content of DDBJ/EMBL/GENBANK accession number AJ270487.2 for microbial strain *Anaerostipes caccae*, butyrate-producing bacterium L1-92, is herein incorporated by reference in its entirety.

The content of DDBJ/EMBL/GENBANK accession number AY305319.1 for microbial strain *Anaerostipes hadrus*, butyrate-producing bacterium SS2/1, is herein incorporated by reference in its entirety.

The content of DDBJ/EMBL/GENBANK accession number AJ315980.1 for microbial strain *Anaerotruncus colihominis*, culture collection DSM 17241, is herein incorporated by reference in its entirety.

The content of DDBJ/EMBL/GENBANK accession number AP009256.1 for microbial strain, *Bifidobacterium adolescentis*, culture collection ATCC 15703, is herein incorporated by reference in its entirety.

The content of DDBJ/EMBL/GENBANK accession number CP001095.1 for microbial strain *Bifidobacterium longum* subsp. *infantis*, culture collection ATCC 15697, is herein incorporated by reference in its entirety.

The content of DDBJ/EMBL/GenBank accession number U41172.1 for microbial strain *Butyrivibrio fibrisolvens*, culture collection ATCC 19171, is herein incorporated by reference in its entirety.

The content of DDBJ/EMBL/GenBank accession number AJ250365.2 for microbial strain *Butyrivibrio fibrisolvens*, 16.4, is herein incorporated by reference in its entirety.

The content of DDBJ/EMBL/GenBank accession number U41168.1 for microbial strain *Butyrivibrio fibrisolvens*, OB156, is herein incorporated by reference in its entirety.

The content of DDBJ/EMBL/GenBank accession number AY305305.1 for microbial strain Butyrate-producing bacterium, A2-232, is herein incorporated by reference in its entirety.

The content of DDBJ/EMBL/GenBank accession number AY305316.1 for microbial strain Butyrate-producing bacterium, SS3/4, is herein incorporated by reference in its entirety.

The content of DDBJ/EMBL/GENBANK accession number AE001437.1 for microbial strain *Clostridium acetobutylicum*, culture collection ATCC 824, is herein incorporated by reference in its entirety.

The content of DDBJ/EMBL/GENBANK accession number X78070.1 for microbial strain *Clostridium acetobutylicum*, culture collection DSM 792, is herein incorporated by reference in its entirety.

The content of DDBJ/EMBL/GENBANK accession number CP000721.1 for microbial strain *Clostridium beijerinckii*, culture collection NCIMB 8052, is herein incorporated by reference in its entirety.

The content of DDBJ/EMBL/GENBANK accession number X68189.1 for microbial strain *Clostridium sporogenes*, is herein incorporated by reference in its entirety.

The content of DDBJ/EMBL/GENBANK accession number X74770.1 for microbial strain *Clostridium tetani*, is herein incorporated by reference in its entirety.

The content of DDBJ/EMBL/GENBANK accession number AJ270491.2 for microbial strain *Coprococcus*, butyrate-producing bacterium L2-50, is herein incorporated by reference in its entirety.

The content of DDBJ/EMBL/GENBANK accession number EF031543.1 for microbial strain *Coprococcus eutactus*, culture collection ATCC 27759, is herein incorporated by reference in its entirety.

The content of DDBJ/EMBL/GenBank accession number AY305306.1 for microbial strain *Eubacterium cylindroides*, butyrate-producing bacterium T2-87, is herein incorporated by reference in its entirety.

The content of DDBJ/EMBL/GenBank accession number AY305313.1 for microbial strain *Eubacterium cylindroides*, butyrate-producing bacterium SM7/11, is herein incorporated by reference in its entirety.

The content of DDBJ/EMBL/GenBank accession number L34682.2 for microbial strain *Eubacterium dolichum*, culture collection DSM 3991, is herein incorporated by reference in its entirety.

The content of DDBJ/EMBL/GenBank accession number AJ270490.2 for microbial strain *Eubacterium halii*, butyrate-producing bacterium L2-7, is herein incorporated by reference in its entirety.

The content of DDBJ/EMBL/GenBank accession number AY305318.1 for microbial strain *Eubacterium halii*, butyrate-producing bacterium SM6/1, is herein incorporated by reference in its entirety.

The content of DDBJ/EMBL/GenBank accession number L34621.2 for microbial strain *Eubacterium halii*, culture collection ATCC 27751, is herein incorporated by reference in its entirety.

The content of DDBJ/EMBL/GenBank accession number AJ270475.2 for microbial strain *Eubacterium rectale*, A1-86, is herein incorporated by reference in its entirety.

The content of DDBJ/EMBL/GENBANK accession number NC_012781.1 for microbial strain *Eubacterium rectale*, culture collection ATCC 33656, is herein incorporated by reference in its entirety.

The content of DDBJ/EMBL/GenBank accession number L34421.2 for microbial strain *Eubacterium ventriosum*, culture collection ATCC 27560, is herein incorporated by reference in its entirety.

The content of DDBJ/EMBL/GENBANK accession number AY305307.1 for microbial strain *Faecalibacterium prausnitzii*, butyrate producing bacterium M21/2, is herein incorporated by reference in its entirety.

The content of DDBJ/EMBL/GENBANK accession number FP929046.1 for microbial strain *Faecalibacterium prausnitzii* is herein incorporated by reference in its entirety.

The content of DDBJ/EMBL/GENBANK accession number GG697168.2 for microbial strain *Faecalibacterium prausnitzii* is herein incorporated by reference in its entirety.

The content of DDBJ/EMBL/GENBANK accession number CP002158.1 for microbial strain *Fibrobacter succinogenes* subsp. *succinogenes* is herein incorporated by reference in its entirety.

The content of DDBJ/EMBL/GENBANK accession number NZ_AUJN01000001.1 for microbial strain *Clostridium butyricum* is herein incorporated by reference in its entirety.

The content of DDBJ/EMBL/GENBANK accession number NZ_AZUI01000001.1 for microbial strain *Clostridium indolis*, culture collection DSM 755, is herein incorporated by reference in its entirety.

The content of DDBJ/EMBL/GENBANK accession number ACEP01000175.1 for microbial strain *Eubacterium hallii*, culture collection DSM 3353, is herein incorporated by reference in its entirety.

The content of DDBJ/EMBL/GenBank accession number AY305310.1 for microbial strain *Roseburia faecis*, M72/1, is herein incorporated by reference in its entirety.

The content of DDBJ/EMBL/GenBank accession number AJ270482.2 for microbial strain *Roseburia hominis*, type strain A2-183T, is herein incorporated by reference in its entirety.

The content of DDBJ/EMBL/GenBank accession number AJ312385.1 for microbial strain *Roseburia intestinalis*, L1-82, is herein incorporated by reference in its entirety.

The content of DDBJ/EMBL/GenBank accession number AJ270473.3 for microbial strain *Roseburia inulinivorans*, type strain A2-194T, is herein incorporated by reference in its entirety.

The content of DDBJ/EMBL/GENBANK accession number NZ_ACFY01000179.1 for microbial strain *Roseburia inulinivorans*, culture collection DSM 16841, is herein incorporated by reference in its entirety.

The content of DDBJ/EMBL/GENBANK accession number KI912489.1 for microbial strain *Ruminococcus flavefaciens*, culture collection ATCC 19208, is herein incorporated by reference in its entirety.

The content of DDBJ/EMBL/GENBANK accession number AAYG02000043.1 for microbial strain *Ruminococcus gnavus*, culture collection ATCC 29149, is herein incorporated by reference in its entirety.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Figure 1:
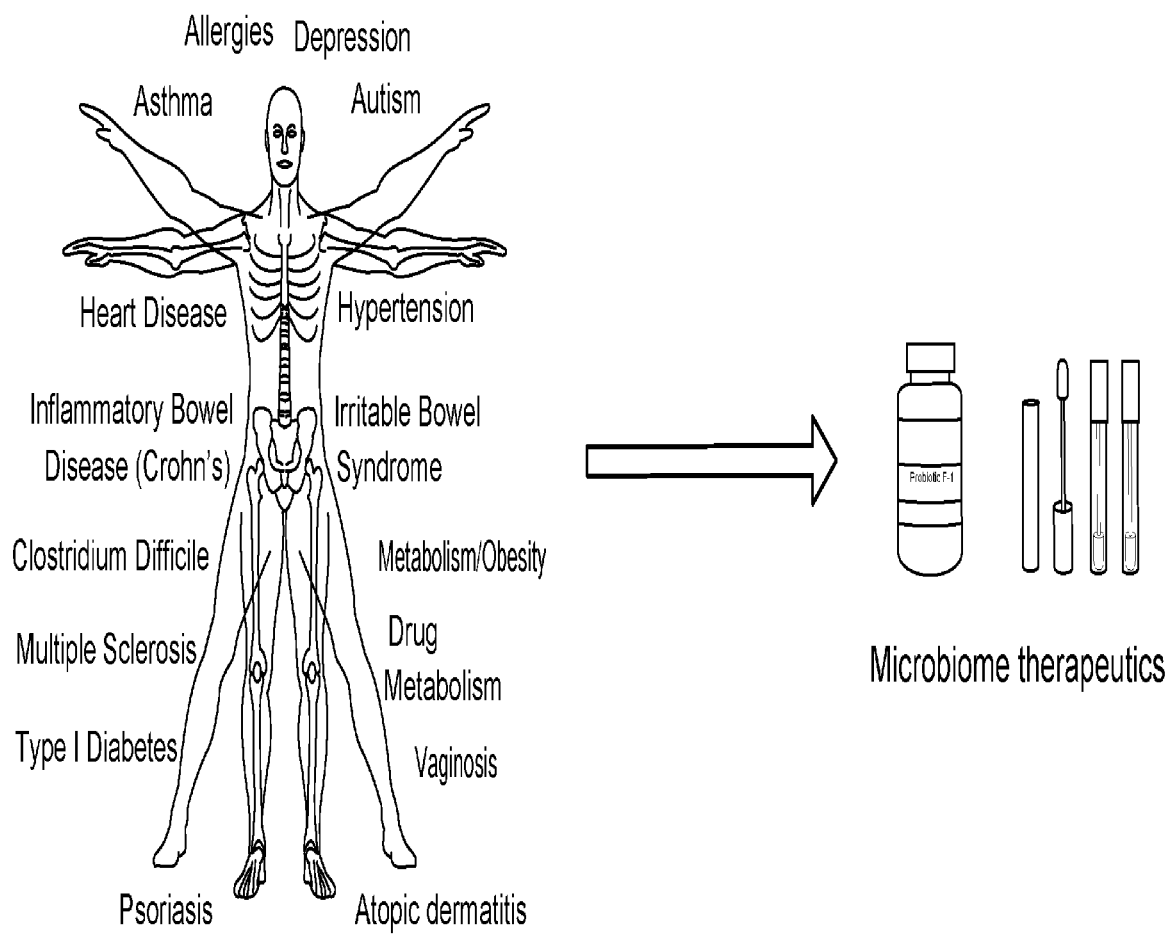
FIG. 1 depicts exemplary microbiome-related health conditions and diseases for which microbiome therapeutics and diagnostics can be used. These health conditions can include: preterm labor, chronic fatigue syndrome, skin health (e.g. acne), Type 2 Diabetes Mellitus (T2DM), allergies, depression, autism, asthma, hypertension, irritable bowel syndrome, metabolism, obesity, drug metabolism, vaginosis, atopic dermatitis, psoriasis, Type I Diabetes (T1DM), Multiple Sclerosis, *Clostridium Difficile*, Inflammatory Bowel Disease (IBD), Crohn's Disease, genitourinary disorders, and heart disease.

The term "probiotic" as used herein can mean one or more microorganisms which, when administered appropriately, can confer a health benefit on the host or subject. Some non-limiting examples of probiotics include: *Akkermansia muciniphila, Anaerostipes caccae, Bifidobacterium adolescentis, Bifidobacterium bifidum, Bifidobacterium infantis, Bifidobacterium longum, Butyrivibrio fibrisolvens, Clostridium acetobutylicum, Clostridium aminophilum, Clostridium beijerinckii, Clostridium butyricum, Clostridium colinum, Clostridium indolis, Clostridium orbiscindens, Enterococcus faecium, Eubacterium hallii, Eubacterium rectale, Faecalibacterium prausnitzii, Fibrobacter succinogenes, Lactobacillus acidophilus, Lactobacillus brevis, Lactobacillus bulgaricus, Lactobacillus casei, Lactobacillus caucasicus, Lactobacillus fermentum, Lactobacillus helveticus, Lactobacillus lactis, Lactobacillus plantarum, Lactobacillus reuteri, Lactobacillus rhamnosus, Oscillospira guilliermondii, Roseburia cecicola, Roseburia inulinivorans, Ruminococcus flavefaciens, Ruminococcus gnavus, Ruminococcus obeum, Streptococcus cremoris, Streptococcus faecium, Streptococcus infantis, Streptococcus mutans, Streptococcus thermophilus, Anaerofustis stercorihominis, Anaerostipes hadrus, Anaerotruncus colihominis, Clostridium sporogenes, Clostridium tetani, Coprococcus, Coprococcus eutactus, Eubacterium cylindroides, Eubacterium dolichum, Eubacterium ventriosum, Roseburia faeccis, Roseburia hominis, Roseburia intestinalis*, and any combination thereof.

The terms "determining", "measuring", "evaluating", "assessing," "assaying," and "analyzing" can be used interchangeably herein and can to refer to any form of measurement, and include determining if an element is present or not. (e.g., detection). These terms can include both quantitative and/or qualitative determinations. Assessing may be relative or absolute. These terms can include use of the algorithms and databases described herein. "Detecting the presence of" can include determining the amount of something present, as well as determining whether it is present or absent. The term "genome assembly algorithm" as used herein, refers to any method capable of aligning sequencing reads with each other (de novo) or to a reference (re-sequencing) under conditions that a complete sequence of the genome may be determined.

The term "genome" as used herein, can refer to the entirety of an organism's hereditary information that is encoded in its primary DNA sequence. The genome includes both the genes and the non-coding sequences. For example, the genome may represent a microbial genome. The genetic content of the microbiome can comprise: genomic DNA, RNA, and ribosomal RNA, the epigenome, plasmids, and all other types of genetic information found in the microbes that comprise the microbiome.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand. The nucleic acid sequence can be made up of adenine, guanine, cytosine, thymine, and uracil (A, T, C, G, and U) as well as modified versions (e.g. N6-methyladenosine, 5-methylcytosine, etc.).

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence.

The term "sequencing" as used herein refers to sequencing methods for determining the order of the nucleotide bases—A, T, C, G, and U—in a nucleic acid molecule (e.g., a DNA or RNA nucleic acid molecule.

The term "biochip" or "array" can refer to a solid substrate having a generally planar surface to which an adsorbent is attached. A surface of the biochip can comprise a plurality of addressable locations, each of which location may have the adsorbent bound there. Biochips can be adapted to engage a probe interface, and therefore, function as probes. Protein biochips are adapted for the capture of polypeptides and can be comprise surfaces having chromatographic or biospecific adsorbents attached thereto at addressable locations. Microarray chips are generally used for DNA and RNA gene expression detection.

The term "barcode" as used herein, refers to any unique, non-naturally occurring, nucleic acid sequence that may be used to identify the originating genome of a nucleic acid fragment.

The terms "subject," "individual," "host," and "patient" can be used interchangeably herein and refer to any animal subject, including: humans, laboratory animals, livestock, and household pets. The subject can host a variety of microorganisms. The subject can have different microbiomes in various habitats on and in their body. The subject may be diagnosed or suspected of being at high risk for a disease. The subject may have a microbiome state that is contributing to a disease (a dysbiosis). In some cases, the subject is not necessarily diagnosed or suspected of being at high risk for the disease. In some instances a subject may be suffering from an infection or at risk of developing or transmitting to others an infection.

The terms "treatment" or "treating" are used interchangeably herein. These terms can refer to an approach for obtaining beneficial or desired results including but not limited to a therapeutic benefit and/or a prophylactic benefit. A therapeutic benefit can mean eradication or amelioration of the underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

The terms "16S", "16S ribosomal subunit", and "16S ribosomal RNA (rRNA)" can be used interchangeably herein and can refer to a component of a small subunit (e.g., 30S) of a prokaryotic (e.g., bacteria, archaea) ribosome. The 16S rRNA is highly conserved evolutionarily among species of microorganisms. Consequently, sequencing of the 16S ribosomal subunit can be used to identify and/or compare microorganisms present in a sample (e.g., a microbiome).

The terms "23S", "23 S ribosomal subunit", and "23 S ribosomal RNA (rRNA)" can be used interchangeably herein and can refer to a component of a large subunit (e.g., 50S) of a prokaryotic (e.g., bacteria, archaea) ribosome. Sequencing of the 23 S ribosomal subunit can be used to identify and/or compare microorganisms present in a sample (e.g., a microbiome).

The term "spore" as used herein can refer to a viable cell produced by a microorganism to resist unfavorable conditions such as high temperatures, humidity, and chemical agents. A spore can have thick walls that allow the microorganism to survive harsh conditions for extended periods of time. Under suitable environmental conditions, a spore can germinate to produce a living form of the microorganism that is capable of reproduction and all of the physiological activities of the microorganism.

Overview

Compositions comprising microbes such as probiotics can confer a variety of beneficial effects on a subject. Examples of these beneficial effects can include immunomodulatory features, regulation of cell proliferation, the ability to promote normal physiologic development of the mucosal epithelium, and enhancement of human nutrition. Microbial-based compositions can be administered as a therapeutic to a subject suffering from a microbiome-related health condition or disorder.

In some embodiments, the disclosure provides a diagnostic assay for predicting a disease status of a subject or likelihood of a subject's response to a therapeutic. The diagnostic assay can use the presence of one or more microbes in a sample or a microbiome profile of a subject to calculate a quantitative score. The quantitative score can be used to predict disease status or likelihood of response to a therapeutic in a subject. In some applications, the diagnostic assay can use the presence of one or more microbes and one or more characteristics, such as, e.g., age, weight, gender, medical history, risk factors, family history, or a combination thereof to calculate a quantitative score that can be used to predict disease status or likelihood of response to a therapeutic in a subject. In some applications, the diagnostic assay can further use environmental factors such as geographic location, type of work, and use of hygiene products to calculate a quantitative score.

An exemplary method of the disclosure can comprise at least one of the following steps: obtaining a biological sample from a subject, measuring a panel of microbes in the biological sample of the subject, determining a disease status upon the measuring, generating a report that provides information of disease status upon the results of the determining, and administering microbial-based compositions of the disclosure to the subject for preventing and/or treating a health condition such as a microbiome-based disorder, or the presence or absence of a microbe.

Methods for Determining Members of a Microbial Habitat

The present disclosure provides methods and compositions comprising microbial populations for the treatment of microbiome-related health conditions and/or disorders in a subject. Methods of the disclosure can include collection, stabilization and extraction of microbes for microbiome analysis. Methods of the disclosure can include determining the composition of a microbial habitat of a host to generate a microbiome profile. The composition of a microbial habitat can be used to diagnose a health condition of a host, for example, to determine likelihood of a disorder and/or treatment course of the disorder.

In some embodiments, methods of the disclosure can be used to determine microbial habitat of the gut or gastrointestinal tract of a subject. The gut comprises a complex microbiome including multiple species of microbes that can contribute to vitamin production and absorption, metabolism of proteins and bile acids, fermentation of dietary carbohydrates, and prevention of pathogen overgrowth. The composition of microbes within the gut can be linked to functional metabolic pathways in a subject. Non-limiting examples of metabolic pathways linked to gut microbiota include, energy balance regulation, secretion of leptin, lipid synthesis, hepatic insulin sensitivity, modulation of intestinal environment, and appetite signaling. Modification of the gut microbiome can increase the risk for health conditions such as ulcerative colitis, colorectal cancer, autoimmune disorders, obesity, diabetes, and inflammatory bowel disease.

In some embodiments, detection methods (e.g. sequencing) can be used to identify gut microbiome biomarkers associated with, for example, obesity and obesity-induced diabetes. For example, non-obese and obese subjects can be categorized based on differences in species of microbes present in their microbiome. Obese subjects can have reduced microbial diversity and higher levels of fermentation causing microbes, for example, bacteroidetes phylum and methanogenic archaea, compared with non-obese subjects. Subjects with obesity-induced diabetes can have a microbiota that promotes mass gain, metabolic endotoxemia, adipose tissue inflammation, and insulin resistance. Differences in microbes between obese and lean subjects can be used to generate microbial biomarker profiles associated with obesity that can be used to predict risk factors and/or treatment course.

In some embodiments, detection methods of the disclosure (e.g., sequencing) can be used to analyze changes in gut microbiome composition over time, for example, during antibiotic treatment, gut microbiome therapies, and various diets. The microbiome can be significantly altered upon exposure to antibiotics and diets that deplete the native microbial population. Methods of the disclosure can be used to generate profiles of the subject before and after administration of a therapeutic to characterize differences in the microbiota.

In some embodiments, methods to visualize the microbiome based on sequencing signatures are provided. In some embodiments, methods are provided to visualize the microbiome over time based on sequencing information.

Methods of the disclosure can be used to detect, characterize and quantify microbial habitat of the amniotic fluid of a pregnant woman. The amniotic cavity of a pregnant woman undergoing preterm labor can harbor genetic material from a greater diversity of microbes, including previously-uncharacterized microbes, compared with pregnant woman delivering at full-term. The microbial habit can be used to define the diversity and abundance of microbes invading the amniotic cavity in order to evaluate clinical significance and causal framework for preterm labor. The microbiome profiles of amniotic fluid of women with full-term delivery and preterm delivery can be compared to determine microbes that can be used as biomarkers for predicting and/or treating preterm labor.

Microorganisms can translocate from a mother to an infant through maternal mononuclear cells in breast milk, which may prime the developing infant immune system to appropriately respond to commensal and pathogenic bacteria. Methods of the disclosure can be used to determine microbial habitat of the gut of an infant to generate patterns of microbial colonization and effects of the microbes on development of immunity during infancy and early childhood.

Methods of the disclosure can be used to analyze microbial habitat of the skin. Parts of the skin, including cutaneous invaginations and appendages, sweat glands (eccrine and apocrine), sebaceous glands and hair follicles, can each be associated with unique microbiota. Comparison of skin microbiome profiles of a healthy subject and a subject with for example, acne, can provide insights into microbial involvement in skin health and disease.

Biological Samples

A biological sample can be collected from a subject to determine the microbiome profile of the subject. The biological sample can be any sample type from any microbial habitat on the body of a subject. Non-limiting examples of microbial habitats include skin habitat, umbilical habitat, vaginal habitat, amniotic fluid habitat, conjunctival habitat, intestinal habitat, stomach habitat, gut habitat, oral habitat, nasal habitat, gastrointestinal tract habitat, respiratory habitat, and urogenital tract habitat.

Depending on the application, the selection of a biological sample can be tailored to the specific application. The biological sample can be for example, whole blood, serum, plasma, mucosa, saliva, cheek swab, urine, stool, cells, tissue, bodily fluid, lymph fluid, CNS fluid, and lesion exudates. A combination of biological samples can be used with the methods of the disclosure.

Sample Preparation

Sample preparation can comprise any one of the following steps or a combination of steps. A sterile swab is first dipped into a tube containing sterile phosphate buffered saline (PBS) to wet. The swab is swiped across the area of interest multiple times (e.g., 10-20 times) with enough vigor that the tissue is slightly pink/red colored afterwards. The swab is gently dipped into a buffer (e.g., a lysis buffer) in a sterile tube. The swab is left in the tube for shipping to a laboratory to be further analyzed as provided herein. The samples obtained can be shipped overnight at room temperature.

Shipping microbial cells in buffers can introduce detection bias in the samples. Some microbes can continue propagating on the nutrients that come along with sample collection. Some microbes can undergo apoptosis in the absence of a specific environment. As a result, microbial samples shipped in this fashion can have an initial profiling/population bias associated with cellular integrity.

Methods can be used to enrich intact cells by first centrifuging the collected sample. The resulting pellet, formed from the intact cells within the sample, can then be used as a precursor for all of the downstream steps. In some embodiments, the methods of the disclosure further comprise a purification step to concentrate any DNA present in the supernatant (e.g. from already lysed cells). This DNA can be combined with DNA extracted from the standard pellet preparation. The combined DNA can form a more complete precursor to the downstream steps.

Cell lysis and/or extraction of nucleic acids from the cells can be performed by any suitable methods including physical methods, chemical methods, or a combination of both. Nucleic acids can be isolated from a biological sample using shearing methods, which preserve the integrity and continuity of genomic DNA.

A nucleic acid sample used with the present disclosure can include all types of DNA and RNA. The length of nucleic acids can be about 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, or 10,000,000, nucleotides or base pairs in length.

An amplicon approach can be used to prepare DNA for microbiome profiling. This approach can comprise a number of steps, for example, PCR, sample quantification (e.g. Qubit, nanodrop, bioanalyzer, etc.), Blue Pippin size selection, 0.5× Ampure purification, sample quantification, DNA end repair, 0.5× Ampure purification, blunt end adaptor ligation, exo-nuclease treatment, two 0.5× Ampure purifications, and final Blue Pippen size selection.

In some embodiments, the method does not use an amplification step. Examples of such methods include preparation of samples for sequencing by Whole Genome Shotgun (WGS) sequencing. These approaches can provide a benefit by removing amplification bias that can skew microbial distributions. In addition, such approaches can allow for de novo discovery of pertinent elements, for example, bacterial plasmids, fungi and viruses.

The practice of the methods of the present disclosure can employ conventional techniques of immunology, biochemistry, chemistry, molecular biology, microbiology, cell biology, genomics and recombinant DNA, which are within the skill of the art. For example, preparation of a biological sample can comprise, e.g., extraction or isolation of intracellular material from a cell or tissue such as the extraction of nucleic acids, protein, or other macromolecules. Sample preparation which can be used with the methods of disclosure include but are not limited to, centrifugation, affinity chromatography, magnetic separation, immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, radioisotope assay, protein synthesis assay, histological assay, culture assay, and combinations thereof.

Microbiome Profiling

The present disclosure provides methods for measuring at least one microbe in a biological sample from at least one microbial habitat of a subject and determining a microbiome profile. A microbiome profile can be assessed using any suitable detection means that can measure or quantify one or more microbes (bacteria, fungi, viruses and archaea) that comprise a microbiome.

Figure 3:
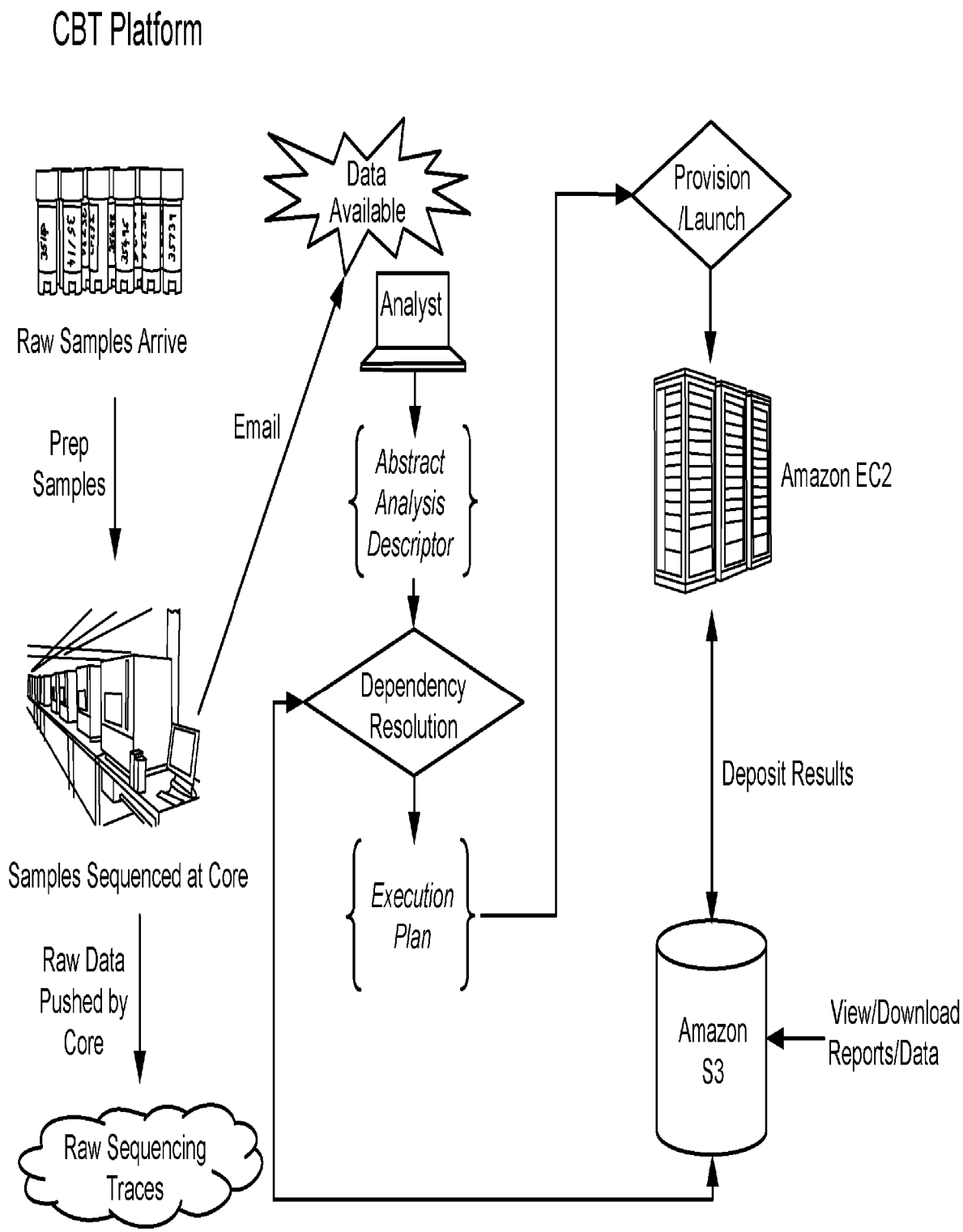
FIG. 3 is an illustration depicting an exemplary platform for a Complete Biome Test (CBT) (e.g. as a diagnostic test or as a development tool to develop therapeutics). The specific microbiotic actionable targets starting with microbiotic strains obtained from, e.g. fecal matter transplants (FMT), the microorganism(s), the genus, and the presence/absence of microorganism strain(s) related to health conditions or diseases can be determined using the Complete Biome Test.
Figure 4:
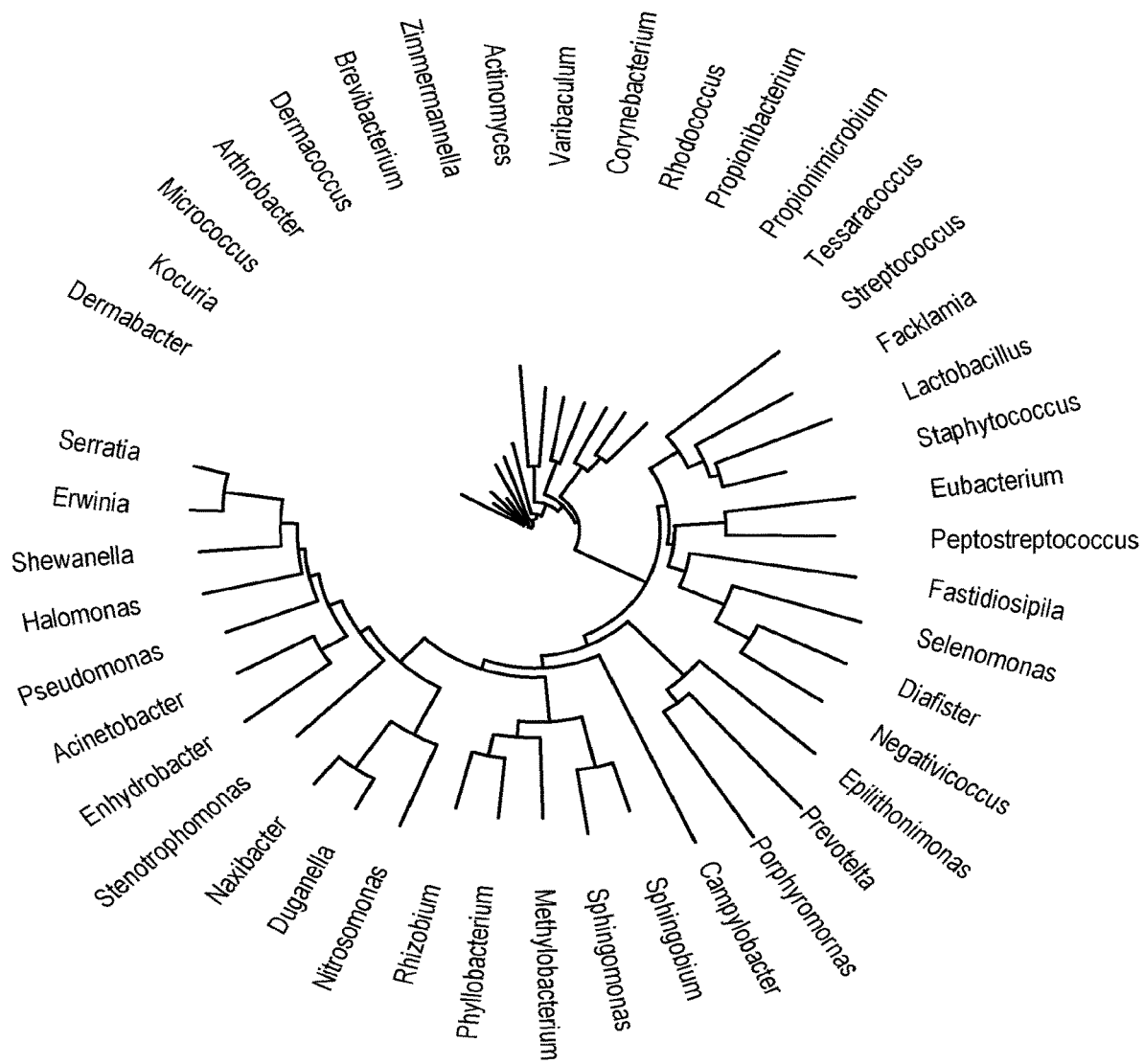
FIG. 4 (A) depicts the microbiome strain resolution using standard tests and (B) the increased microbiome strain resolution using the Complete Biome Test.
Figure 4:
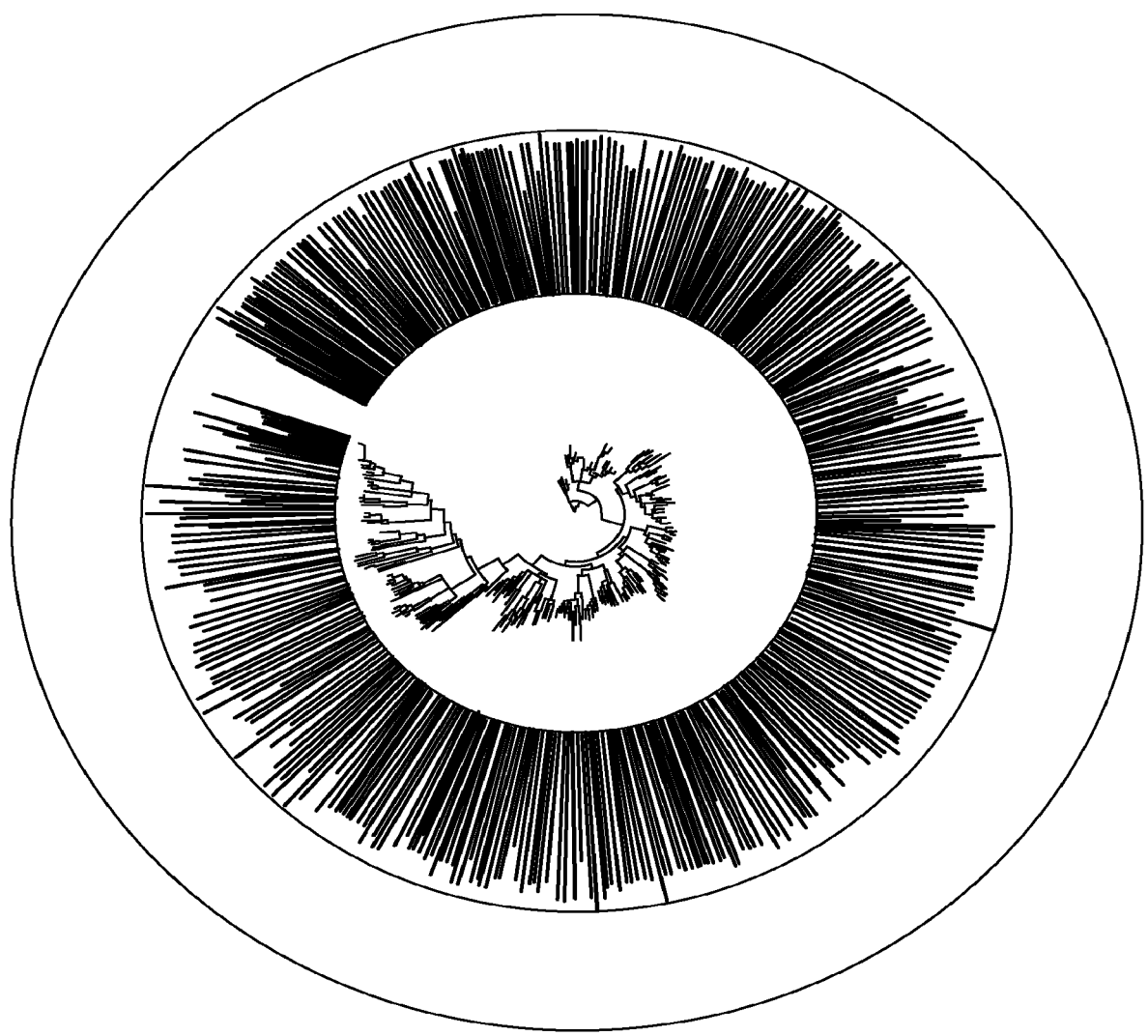
Figure 5:
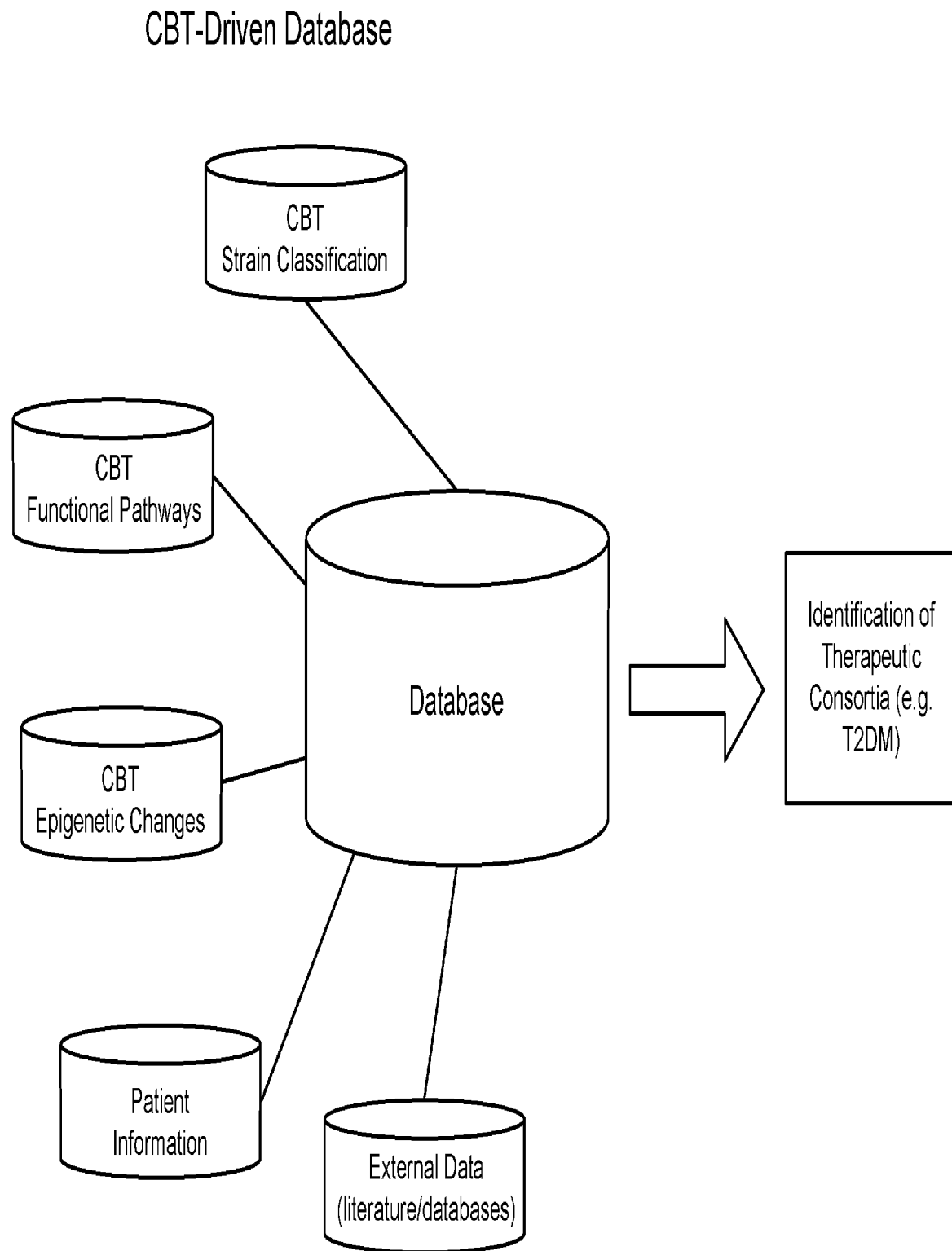
FIG. 5 depicts an illustrative process for generating a database using data obtained from the group consisting of: external data (e.g. scientific literature and/or databases), patient information, measured epigenetic changes, measured functional pathways, measured strain classification, and any combinations thereof. The database can be used, e.g. to drive identification of a therapeutic consortia (e.g. for treatment of health conditions or diseases).
Figure 8:
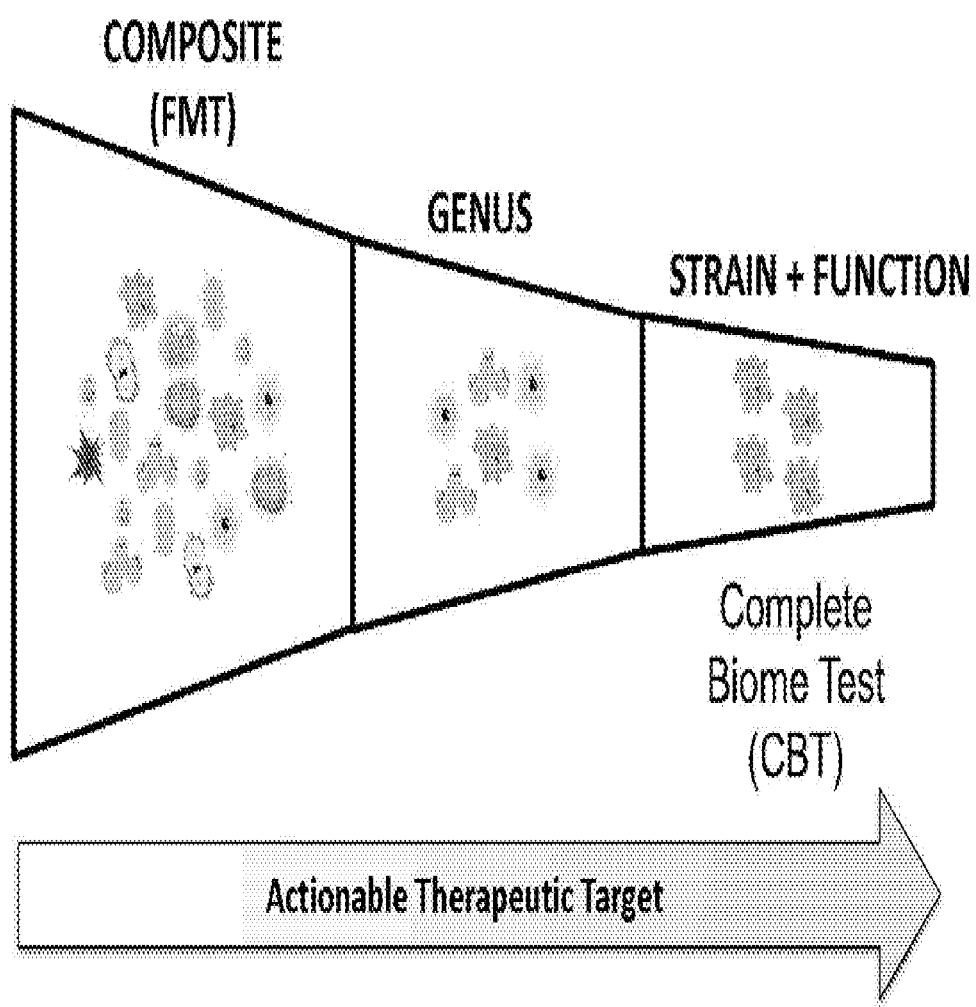
FIG. 8 depicts how both the diagnostic and therapeutic approach outlined herein can comprise a targeted microbe strain selection as compared to a composite fecal microbiome transplant.

A Complete Biome Test (CBT) can generate microbiome profiles with, for example, strain-level resolution. A CBT can be performed using microbiome profiling methods described herein. FIG. 3 provides an illustration depicting an exemplary platform for a CBT (e.g. as a diagnostic test or as a development tool to develop therapeutics). The specific microbiotic actionable targets starting with microbiotic strains obtained from, e.g. fecal matter transplants (FMT), the microorganism(s), the genus, and the presence/absence of microorganism strain(s) related to health conditions or diseases can be determined using the CBT. FIG. 4(A) depicts the microbiome strain resolution using standard tests. FIG. 4(B) depicts the increased microbiome strain resolution using the CBT. FIG. 5 depicts an illustrative process for generating a database (e.g., a CBT driven-database using data obtained from the group consisting of: external data (e.g. scientific literature and/or databases), patient information, measured epigenetic changes, measured functional pathways, measured strain classification, and any combinations thereof. The database can be used, e.g. to drive identification of a therapeutic consortia (e.g. for treatment of health conditions or diseases). FIG. 8 depicts how both the diagnostic and therapeutic approach outlined herein can comprise a targeted microbe strain selection or therapeutic consortia as compared to a composite fecal microbiome transplant.

Nucleic acid sample prepared from a biological sample can be subjected to a detection method to generate a profile of the microbiome associated with the sample. Profiling of a microbiome can comprise one or more detection methods.

Methods of the disclosure can be used to measure, for example, a 16S ribosomal subunit, a 23S ribosomal subunit, intergenic regions, and other genetic elements. Suitable detection methods can be chosen to provide sufficient discriminative power in a particular microbe in order to identify informative microbiome profiles.

In some applications, the entire genomic region of the 16S or 23S ribosomal subunit of the microbe is analyzed to determine a subject's microbiome profile. In some applications, the variable regions of the 16S and/or 23S ribosomal subunit of the microbe are analyzed to determine a subject's microbiome profile.

In some applications, the entire genome of the microbe is analyzed to determine a subject's microbiome profile. In other applications, the variable regions of the microbe's genome are analyzed to determine a subject's microbiome profile. For example, genetic variation in the genome can include restriction fragment length polymorphisms, single nucleotide polymorphisms, insertions, deletions, indels (insertions-deletions), microsatellite repeats, minisatellite repeats, short tandem repeats, transposable elements, randomly amplified polymorphic DNA, amplification fragment length polymorphism or a combination thereof.

In some embodiments, sequencing methods such as long-read length single molecule sequencing is used for detection. Long read sequencing can provide microbial classification down to the strain resolution of each microbe. Examples of sequencing technologies that can be used with the present disclosure for achieving long read lengths include the SMRT sequencing systems from Pacific Biosciences, long read length Sanger sequencing, long read ensemble sequencing approaches, e.g., Illumina/Moleculo sequencing and potentially, other single molecule sequencing approaches, such as Nanopore sequencing technologies.

Long read sequencing can include sequencing that provides a contiguous sequence read of for example, longer than 500 bases, longer than 800 bases, longer than 1000 bases, longer than 1500 bases, longer than 2000 bases, longer than 3000 bases, or longer than 4500 bases.

In some embodiments, detection methods of the disclosure comprise amplification-mode sequencing to profile the microbiome. In some embodiments, detection methods of the disclosure comprise a non-amplification mode, for example Whole Genome Shotgun (WGS) sequencing, to profile the microbiome.

Primers used in the disclosure can be prepared by any suitable method, for example, cloning of appropriate sequences and direct chemical synthesis. Primers can also be obtained from commercial sources. In addition, computer programs can be used to design primers. Primers can contain unique barcode identifiers.

Microbiome profiling can further comprise use of for example, a nucleic acid microarray, a biochip, a protein microarray, an analytical protein microarray, reverse phase protein microarray (RPA), a digital PCR device, and/or a droplet digital PCR device.

In some embodiments, the microbial profile is determined using additional information such as age, weight, gender, medical history, risk factors, family history, or any other clinically relevant information.

In some applications, a subject's microbiome profile comprises a single microbiome. For example, a subject's microbiome profile can comprise of at least one biological sample from only the subject's intestinal microbiome. In another example, a subject's microbiome profile can comprise of at least one biological sample from only the subject's stomach microbiome. In another example, a subject's microbiome profile can comprise of at least one biological sample from only the subject's gut microbiome. In another example, a subject's microbiome profile can comprise of at least one biological sample from only the subject's oral microbiome.

In some applications, a subject's microbiome profile comprises at least one biological sample from more than one microbiome. For example, a subject's microbiome profile can comprise of at least one biological sample from the subject's skin microbiome and at least one biological sample from the umbilical microbiome. In another example, a subject's microbiome profile can comprise of at least one biological sample from the subject's intestinal microbiome, at least one biological sample from the stomach microbiome, at least one biological sample from the gut microbiome, and at least one biological sample from the oral microbiome. In another example, a subject's microbiome profile can comprise of at least one biological sample from the subject's intestinal microbiome, and at least one biological sample from stomach microbiome. In another example, a subject's microbiome profile can comprise of at least one biological sample from the subject's gut microbiome, and at least one biological sample from oral microbiome. In some applications, a subject's microbiome profile can comprise of at least 2, 3, 4, 5, 6, 7, 8, 9, 10, 11, 12, 13, 14, 15, 16, 17, 18, 19, 20 microbiomes.

A subject's microbiome profile can comprise of one microbe. In some applications, a subject's microbiome profile comprises of, for example, 2 microbes, 3 or fewer microbes, 4 or fewer microbes, 5 or fewer microbes, 6 or fewer microbes, 7 or fewer microbes, 8 or fewer microbes, 9 or fewer microbes, 10 or fewer microbes, 11 or fewer microbes, no more than 12 microbes, 13 or fewer microbes, 14 or fewer microbes, 15 or fewer microbes, 16 or fewer microbes, 18 or fewer microbes, 19 or fewer microbes, 20 or fewer microbes, 25 or fewer microbes, 30 or fewer microbes, 35 or fewer microbes, 40 or fewer microbes, 45 or fewer microbes, 50 or fewer microbes, 55 or fewer microbes, 60 or fewer microbes, 65 or fewer microbes, 70 or fewer microbes, 75 or fewer microbes, 80 or fewer microbes, 85 or fewer microbes, 90 or fewer microbes, 100 or fewer microbes, 200 or fewer microbes, 300 or fewer microbes, 400 or fewer microbe, 500 or fewer microbes, 600 or fewer microbes, 700 or fewer microbes, or 800 or fewer microbes.

Algorithm-Based Methods

The present disclosure provides algorithm-based methods for building a microbiome profile of a subject. Non-limiting examples of algorithms that can be used with the disclosure include elastic networks, random forests, support vector machines, and logistic regression.

The algorithms can transform the underlying measurements into a quantitative score or probability relating to, for example, disease risk, disease likelihood, presence or absence of disease, presence or absence of a microbe, treatment response, and/or classification of disease status. The algorithms can aid in the selection of important microbes.

Analysis

A microbiome profile of a subject can be analyzed to determine information related to the health status of the subject. The information can include, for example, degree of likelihood of a disorder, presence or absence of a disease state, a poor clinical outcome, good clinical outcome, high risk of disease, low risk of disease, complete response, partial response, stable disease, non-response, and recommended treatments for disease management.

The analysis can be a part of a diagnostic assay to predict disease status of a subject or likelihood of a subject's response to a therapeutic. The diagnostic assay can use the quantitative score calculated by the algorithms-based methods described herein to perform the analysis.

In some applications, an increase in one or more microbes' threshold values or quantitative score in a subject's microbiome profile indicates an increased likelihood of one or more of: a poor clinical outcome, good clinical outcome, high risk of disease, low risk of disease, complete response, partial response, stable disease, non-response, and recommended treatments for disease management. In some embodiments, a decrease in the quantitative score indicates an increased likelihood of one or more of: a poor clinical outcome, good clinical outcome, high risk of disease, low risk of disease, complete response, partial response, stable disease, non-response, and recommended treatments for disease management.

In some applications, a decrease in one or more microbes' threshold values or quantitative score in a subject's microbiome profile indicates a decreased likelihood of one or more of: a poor clinical outcome, good clinical outcome, high risk of disease, low risk of disease, complete response, partial response, stable disease, non-response, and recommended treatments for disease management. In some embodiments, a decrease in the quantitative score indicates an increased likelihood of one or more of: a poor clinical outcome, good clinical outcome, high risk of disease, low risk of disease, complete response, partial response, stable disease, non-response, and recommended treatments for disease management.

In some applications, an increase in one or more microbes' threshold values or quantitative score in a subject's microbiome profile indicates an increased likelihood of one or more of: a poor clinical outcome, good clinical outcome, high risk of disease, low risk of disease, complete response, partial response, stable disease, non-response, and recommended treatments for disease management. In some applications, a decrease in one or more microbes' threshold values indicates an increased likelihood of one or more of: a poor clinical outcome, good clinical outcome, high risk of disease, low risk of disease, complete response, partial response, stable disease, non-response, and recommended treatments for disease management.

In some applications, an increase in one or more microbes' threshold values or quantitative score in a subject's microbiome profile indicates a decreased likelihood of one or more of: a poor clinical outcome, good clinical outcome, high risk of disease, low risk of disease, complete response, partial response, stable disease, non-response, and recommended treatments for disease management. In some applications, a decrease in one or more microbes' threshold values indicates an increased likelihood of one or more of: a poor clinical outcome, good clinical outcome, high risk of disease, low risk of disease, complete response, partial response, stable disease, non-response, and recommended treatments for disease management.

In some applications, a similar microbiome profile to a reference profile indicates an increased likelihood of one or more of: a poor clinical outcome, good clinical outcome, high risk of disease, low risk of disease, complete response, partial response, stable disease, non-response, and recommended treatments for disease management. In some applications, a dissimilar microbiome profile to a reference profile indicates one or more of: an increased likelihood of a poor clinical outcome, good clinical outcome, high risk of disease, low risk of disease, complete response, partial response, stable disease, non-response, and recommended treatments for disease management.

In some applications, a similar microbiome profile to a reference profile indicates a decreased likelihood of one or more of: a poor clinical outcome, good clinical outcome, high risk of disease, low risk of disease, complete response, partial response, stable disease, non-response, and recommended treatments for disease management. In some applications, a dissimilar microbiome profile to a reference profile indicates one or more of: an increased likelihood of a poor clinical outcome, good clinical outcome, high risk of disease, low risk of disease, complete response, partial response, stable disease, non-response, and recommended treatments for disease management.

In some applications, a dissimilar microbiome profile to a reference profile indicates an increased likelihood of one or more of: a poor clinical outcome, good clinical outcome, high risk of disease, low risk of disease, complete response, partial response, stable disease, non-response, and recommended treatments for disease management. In some applications, a dissimilar microbiome profile to a reference profile indicates one or more of: an increased likelihood of a poor clinical outcome, good clinical outcome, high risk of disease, low risk of disease, complete response, partial response, stable disease, non-response, and recommended treatments for disease management.

In some applications, a dissimilar microbiome profile to a reference profile indicates a decreased likelihood of one or more of: a poor clinical outcome, good clinical outcome, high risk of disease, low risk of disease, complete response, partial response, stable disease, non-response, and recommended treatments for disease management. In some applications, a dissimilar microbiome profile to a reference profile indicates one or more of: an increased likelihood of a poor clinical outcome, good clinical outcome, high risk of disease, low risk of disease, complete response, partial response, stable disease, non-response, and recommended treatments for disease management.

An accurate 16S Copy Number can be required to accurately quantify using 16S profiling. Using an incorrect database estimate of the copy number can be off by several factors, and in some cases an order of magnitude or more.

Figure 12:
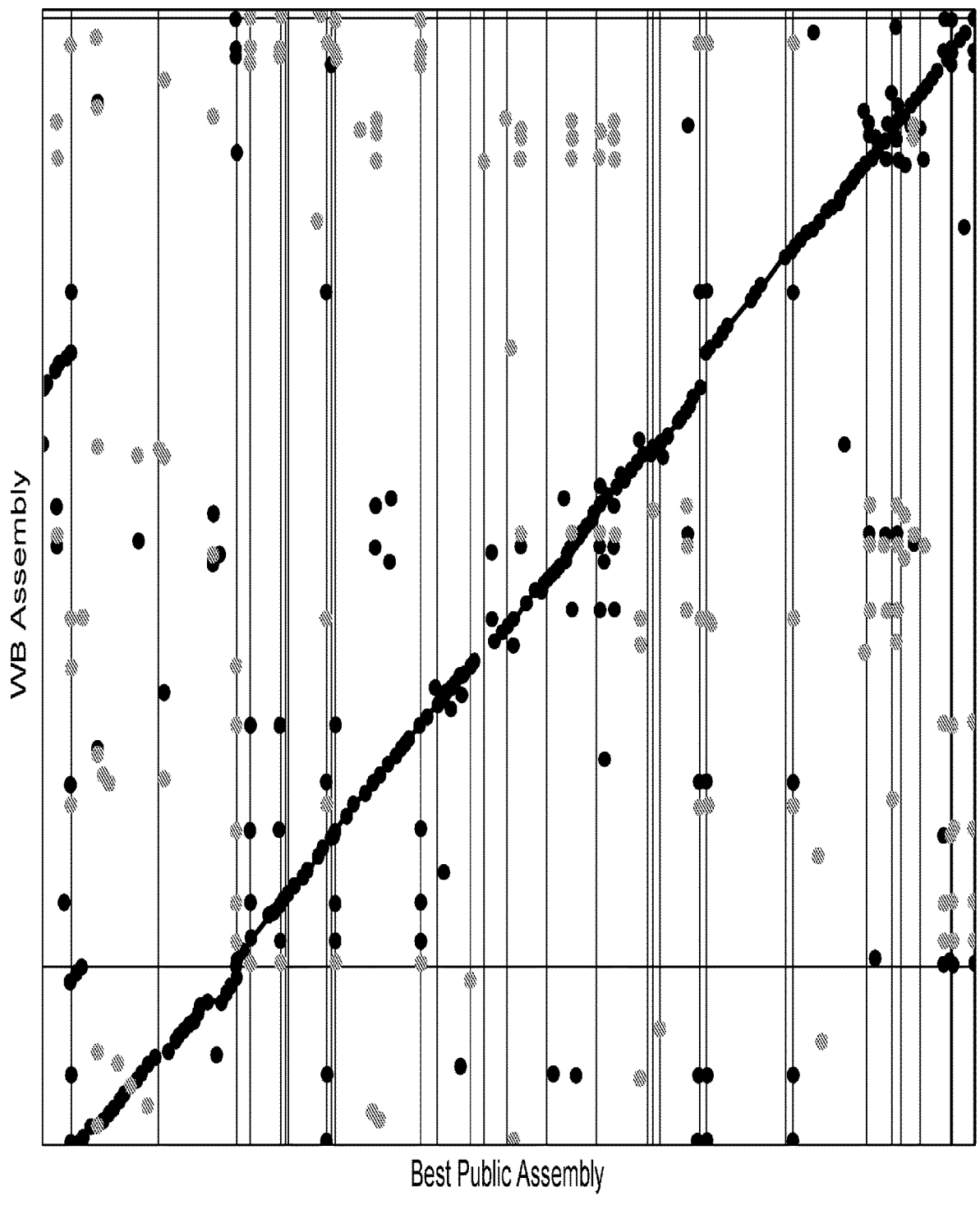
FIG. 12 illustrates that de novo assembly for *C. butyricum* using methods of the invention can result in the use of less contigs (e.g., 2 contigs) than those found in the database (e.g., 40 contigs).
Figure 13:
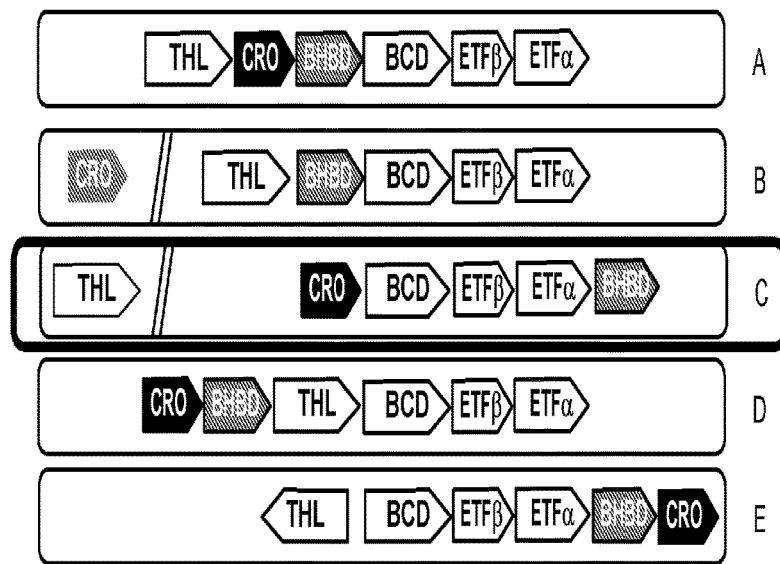
FIG. 13 (A) illustrates that de novo assembly using a method of the choke, dandelion greens, garlic, leek, onion, asparagus, wheat bran, oat bran, baked beans, whole wheat flour, banana), and breast milk. Prebiotics can also be administered in other forms (e.g. capsule or dietary supplement).

FIG. 12 illustrates that de novo assembly for *C. butyricum* using methods of the invention can result in the use of less contigs (e.g., 2 contigs) than those found in the database (e.g., 40 contigs).

FIG. 13(A) illustrates that de novo assembly using a method of the invention can differentiate between several operon orderings and for this example strain of *C. butyricum* a 'type C' ordering was discovered. (B) Tabulates the exact genomic coordinates for five of the butyrate pathway genes for this strain.

Accuracy and Sensitivity

The methods provided herein can provide strain classification of a genera, species or sub-strain level of one or more microbes in a sample with an accuracy of greater than 1%, 20%, 30%, 40%, 50%, 55%, 60%, 65%, 70%, 75%, 80%, 85%, 90%, 95%, 96%, 97%, 98%, 99%, 99.2%, 99.5%, 99.7%, or 99.9%. The methods provided herein can provide strain quantification of a genera, species or sub-strain level of one or more microbes in a sample with an accuracy of greater than 1%, 20%, 30%, 40%, 50%, 55%, 60%, 65%, 70%, 75%, 80%, 85%, 90%, 95%, 96%, 97%, 98%, 99%, 99.2%, 99.5%, 99.7%, or 99.9%.

The microbial profile can have an accuracy of 70% or greater based on measurement of 15 or fewer microbes in the biological sample. Such profiling method can have at least an accuracy greater than 70% based on measurement of no more than 2 microbes, 3 or fewer microbes, 4 or fewer microbes, 5 or fewer microbes, 6 or fewer microbes, 7 or fewer microbes, 8 or fewer microbes, 9 or fewer microbes, 10 or fewer microbes, 11 or fewer microbes, no more than 12 microbes, 13 or fewer microbes, 14 or fewer microbes, 15 or fewer microbes, 16 or fewer microbes, 18 or fewer microbes, 19 or fewer microbes, 20 or fewer microbes, 25 or fewer microbes, 30 or fewer microbes, 35 or fewer microbes, 40 or fewer microbes, 45 or fewer microbes, 50 or fewer microbes, 55 or fewer microbes, 60 or fewer microbes, 65 or fewer microbes, 70 or fewer microbes, 75 or fewer microbes, 80 or fewer microbes, 85 or fewer microbes, 90 or fewer microbes, or 100 or fewer microbes, 200 or fewer microbes, 300 or fewer microbes, 400 or fewer microbes, 500 or fewer microbes, 600 or fewer microbes, 700 or fewer microbes, or 800 or fewer microbes.

The diagnostic methods provided by the present disclosure for the diseases provided herein can have at least one of a sensitivity of 70% or greater and specificity of greater than 70% based on measurement of 15 or fewer microbes in the biological sample. Such diagnostic method can have at least one of a sensitivity greater than 70% and specificity greater than 70% based on measurement of no more than 2 microbes, 3 or fewer microbes, 4 or fewer microbes, 5 or fewer microbes, 6 or fewer microbes, 7 or fewer microbes, 8 or fewer microbes, 9 or fewer microbes, 10 or fewer microbes, 11 or fewer microbes, no more than 12 microbes, 13 or fewer microbes, 14 or fewer microbes, 15 or fewer microbes, 16 or fewer microbes, 18 or fewer microbes, 19 or fewer microbes, 20 or fewer microbes, 25 or fewer microbes, 30 or fewer microbes, 35 or fewer microbes, 40 or fewer microbes, 45 or fewer microbes, 50 or fewer microbes, 55 or fewer microbes, 60 or fewer microbes, 65 or fewer microbes, 70 or fewer microbes, 75 or fewer microbes, 80 or fewer microbes, 85 or fewer microbes, 90 or fewer microbes, or 100 or fewer microbes, 200 or fewer microbes, 300 or fewer microbes, 400 or fewer microbes, 500 or fewer microbes, 600 or fewer microbes, 700 or fewer microbes or 800 or fewer microbes.

The methods provided herein can provide a health status of a subject with a specificity greater than 1%, 20%, 30%, 40%, 50%, 55%, 60%, 65%, 70%, 75%, 80%, 85%, 90%, 95%, 96%, 97%, 98%, 99%, 99.2%, 99.5%, 99.7%, or 99.9% receiver operating characteristic (ROC). The methods provided herein can provide a health status of a subject with a sensitivity lesser than 1%, 20%, 30%, 40%, 50%, 55%, 60%, 65%, 70%, 75%, 80%, 85%, 90%, 95%, 96%, 97%, 98%, 99%, 99.2%, 99.5%, 99.7%, or 99.9% ROC.

Methods for Treating a Subject

The disclosure provides methods for treating a subject. Altering the composition of a microbiome in a subject can have desired health consequences. Compositions of the disclosure can be administered as a therapeutic and/or a cosmetic for treating a health condition. Treatments designed to alter the host microbiome(s) can result in a reduction of patient symptoms, prevention of disease, and or treatment of the disease or health condition. For example, modification of the gut microbiome can reduce the risk for health conditions such as metabolic disorders.

The disclosure provides methods for the restoration of a microbial habitat of a subject to a healthy state. The method can comprise microbiome correction and/or adjustment including for example, replenishing native microbes, removing pathogenic microbes, administering prebiotics, and growth factors necessary for microbiome survival. In some embodiments, the method also comprises administering antimicrobial agents such as antibiotics.

Based on the microbiome profile, the present disclosure provides methods for generalized-treatment recommendation for a subject as well as methods for subject-specific treatment recommendation. Methods for treatments can comprise one of the following steps: determining a first ratio of a level of a subject-specific microbiome profile to a level of a second microbiome profile in a biological sample obtained from at least one subject, detecting a presence or absence of a disease in the subject based upon the determining, and recommending to the subject at least one generalized or subject-specific treatment to ameliorate disease symptoms.

FIG. 1 depicts some non-limiting heath conditions that can be affected by the microbiome. These health conditions can include, for example, Type 2 Diabetes Mellitus (T2DM), preterm labor, chronic fatigue syndrome, skin conditions such as acne, allergies, autism, asthma, depression, hypertension, irritable bowel syndrome, metabolic syndrome, obesity, lactose intolerance, oral thrush, ulcerative colitis, drug metabolism, vaginosis, atopic dermititus, psoriasis, Type I Diabetes Mellitus (T1DM), Multiple Sclerosis, neurological disorders such as Parkinson's disease, *Clostridium Difficile* infection, Inflammatory Bowel Disease, Crohn's Disease, heart disease, diabetic foot ulcers, bacteremia, infantile colic, cancer, cystic fibrosis, multiple sclerosis, urinary tract infection, radiation enteropathy, drug metabolism, dental cavities, and halitosis. The present disclosure can provide for a diagnostic assay of at least one microbiome that includes a report that gives guidance on health status or treatment modalities for the health conditions described herein. The present disclosure can also provide therapeutic and/or cosmetic formulations for treatment of health conditions described herein.

Inflammatory bowel disease (IBD) can involve chronic inflammation of all or part of the digestive tract. IBD can lead to ulcerative colitis and/or Crohn's disease. IBD can be painful and debilitating, and sometimes leads to life-threatening complications.

Preterm labor can occur when contractions begin to open the cervix before 37 weeks of pregnancy. The earlier premature birth happens, the greater the health risks for the developing baby. Many premature babies need special care in the neonatal intensive care unit. Premature babies can also have long-term mental and physical disabilities.

Obesity can be a complex disorder involving an excessive amount of body fat. Obesity can increase the risk of diseases and health problems such as heart disease, diabetes and high blood pressure.

Peripheral neuropathy is the most common form of diabetic neuropathy. In peripheral neuropathy, the feet and legs can be affected first, followed by the hands and arms. Possible signs and symptoms of peripheral neuropathy can include serious foot problems, such as ulcers, infections, deformities, and bone and joint pain.

Bacteremia or septicemia can refer to the presence of bacteria in the blood. A diagnosis of bacteremia can be confirmed by a blood culture. Treatment can require hospitalization and intravenous antibiotics. Bacteremia can quickly progress to severe sepsis.

Acne is a skin condition that can occur when the hair follicles become plugged with oil and dead skin cells. Acne can appear on the face, neck, chest, back and shoulders. Depending on the severity of the acne, the condition can cause emotional distress and lead to scarring of the skin.

Infantile colic can refer to a condition involving an infant with excessive crying, irritability, or fussiness. Babies with colic can cry for more than three hours a day, three days a week for three weeks or longer.

Type 2 diabetes also known as adult-onset or noninsulin-dependent diabetes can be a chronic condition that affects the way the body metabolizes glucose. In type 2 diabetes, the body can either resist the effects of insulin or not produce enough insulin to maintain a normal glucose level. Untreated, type 2 diabetes can be life-threatening. Symptoms of Type 2 diabetes can include, for example, increased thirst and frequent urination, increased hunger, weight gain, weight loss, fatigue, blurred vision, slow-healing sores or frequent infections, areas of darkened skin, and *acanthosis nigricans*.

*Clostridium difficile* also called *C. difficile* or *C. diff* is a bacterium that can cause symptoms ranging from diarrhea to life-threatening inflammation of the colon.

Asthma is a condition in which the airways can become narrow, swell and produce extra mucus. The changes in the airway can make breathing difficult and trigger coughing, wheezing and shortness of breath.

Autism spectrum disorder (ASD) can be a serious neurodevelopmental disorder that impairs a child's ability to communicate and interact with others. The disorder also includes restricted repetitive behaviors, interests and activities. ASC can include autism, Asperger's syndrome, childhood disintegrative disorder and pervasive developmental disorder not otherwise specified.

Psoriasis is a persistent and chronic skin condition that can change the life cycle of skin cells. Psoriasis can cause cells to build up rapidly on the surface of the skin. The extra skin cells can form thick, silvery scales and itchy, dry, red patches that are sometimes painful.

Allergies can occur when the immune system reacts to a foreign substance such as pollen, bee venom or pet dander. The immune system's reaction to an allergen can involve inflammation of the skin, sinuses, airways or digestive system.

Cardiovascular diseases can affect the heart, arteries and veins of the body. Examples of some cardiovascular disease include heart valve disease, coronary artery disease, congenital heart disease in adults and congenital heart spontaneous coronary artery dissection, heart failure, heart rhythm disorders (arrhythmias).

Cancer can refer to any one of a large number of proliferative diseases characterized by the development of abnormal cells that divide uncontrollably and have the ability to infiltrate and destroy normal body tissues and organs.

Depression, major depression, major depressive disorder or clinical depression can refer to a mood disorder that causes a persistent feeling of sadness and loss of interest. Depression can affect how a subject feels, thinks and behaves and can lead to a variety of emotional and physical problems.

Cystic fibrosis is a life-threatening genetic disorder that can cause severe damage to the lungs and digestive system. Cystic fibrosis affects the cells that produce secreted fluids such as mucus, sweat and digestive juices that act as lubricants in the body. These secreted fluids are normally thin and slippery but in cystic fibrosis the secretions to become thick and sticky resulting in plugging up tubes, ducts and passageways, especially in the lungs and pancreas.

Multiple sclerosis is a disease in which the immune system attacks the protective sheath (myelin) that covers the nerves. Myelin damage disrupts communication between the brain and the rest of the body. Ultimately, the nerves themselves may deteriorate a process that's currently irreversible.

Urinary tract infection is an infection in any part of the urinary system (e.g. kidneys, ureters, bladder and urethra). Urinary tract infection can be painful. Serious consequences can occur if a urinary tract infection spreads to the kidneys.

Radiation enteropathy can refer to radiation-induced gastrointestinal injury. Radiotherapy is a mainstay of oncological treatment for a variety of malignant diseases. Radiotherapy can be administered to the abdomen and pelvis of patients with gastrointestinal (GI), urological and gynaecological cancers.

Drug metabolism can refer to the rate at which the body breaks down as drug after administration.

Chronic fatigue syndrome is a complicated disorder characterized by extreme fatigue that cannot be explained by an underlying medical condition. The fatigue may worsen with physical or mental activity, but may not improve with rest.

Type 1 diabetes, also known as juvenile diabetes or insulin-dependent diabetes, is a chronic condition in which the pancreas produces little or no insulin, a hormone needed to allow sugar (glucose) to enter cells to produce energy. Various factors may contribute to type 1 diabetes, including genetics and exposure to certain viruses. Although type 1 diabetes typically appears during childhood or adolescence, it also can develop in adults.

Dental cavities can be caused by the conversion of sugar from food to elongated, sticky sugar chains through a bacterially produced glucansucrase enzyme. One approach to treat and/or prevent cavities can be to reduce the proportion of *Streptococcus mutans*, which is the bacteria associated with tooth decay. This approach can leave enzymes such as enzymes used by the body to break down starches intact while simultaneously minimizing the rate of cavity formation.

Halitosis is a dental condition in which excessively bad breath can be produced by the microbial flora present in a subject's mouth. Examples of halitosis related microbes include gram-negative bacteria such as *Prevotella intermedia, Porphyromonas gingivalis, Treponema denticola*. Methods of the disclosure can be used to generate a list comprising problematic and protective microbes associated with halitosis.

Antibiotics can alter microbial populations in the gastrointestinal tract. This alteration can result in antimicrobial-associated diarrhea and/or colitis.

Obesity can occur in subjects with a body mass index of 30 or greater. Obesity can be associated with, for example, breathlessness, increased sweating, snoring, difficulty sleeping, inability to cope with sudden physical activity, fatigue, back pain, joint pain, high blood pressure, hypertension, high cholesterol levels, coronary heart disease, stroke, thirst, frequent urination, and diabetes.

A subject treated with the microbial compositions of the invention can lose weight. The subject can lose, for example, about: 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 pounds of body weight.

A subject treated with the microbial compositions of the invention can lose weight. The subject can lose, for example, about: 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 pounds of body weight.

A subject treated with the microbial compositions of the invention can gain weight. The subject can gain, for example, about: 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 pounds of body weight.

The body mass index of a subject treated with the microbial compositions of the invention can be reduced to, for example, less than 30, between about 25 to 30, or less than about 25.

Microbial compositions of the invention can increase blood glucose levels. Microbial compositions of the invention can decrease blood glucose levels. An oral glucose tolerance test (OGTT) can be used to measure glucose tolerance. Fasting plasma glucose, measured before the OGTT begins, of below 6.1 mmol/L (i.e. 110 mg/dL) can be considered normal. Fasting levels between 6.1 and 7.0 mmol/L (i.e. 110 and 125 mg/dL) can be considered borderline (e.g., impaired fasting glycaemia). Fasting levels repeatedly at or above 7.0 mmol/L (i.e. 126 mg/dL) can be diagnostic of diabetes. Microbial compositions of the invention can decrease blood glucose levels to normal levels, for example, below 6.1 mmol/L (i.e. 110 mg/dL). Microbial compositions of the invention can decrease blood glucose levels to below diabetes levels or below borderline levels as described herein.

Metabolic Diseases

Modifying a patient's microbiome, e.g. gut, intestinal tract, and/or colon microbiome, can result in prevention and/or treatment of a metabolic health condition, including: T2DM, T1DM, obesity, metabolic disorder, insulin resistance, and other diseases.

In some embodiments, the metabolic condition is T2DM. In some embodiments, the metabolic condition is obesity. In some embodiments, the metabolic condition is T1DM.

Butyrate is an anti-inflammatory factor that can affects gut permeability. Low levels of butyrate producing bacteria (e.g. *Clostridium* clusters XIVa and IV) as well as reduced lactate producing bacteria (e.g. *Bifidobacterium adolescentis*) can be correlated with T1DM. Low levels of butyrate producing bacteria (e.g. *Clostridium* clusters XIVa and IV) as well as reduced lactate producing bacteria (e.g. *Bifidobacterium adolescentis*) can be correlated with T2DM. Low levels of butyrate producing bacteria (e.g. *Clostridium* clusters XIVa and IV) as well as reduced lactate producing bacteria (e.g. *Bifidobacterium adolescentis*) can be correlated with obesity. Low levels of butyrate producing bacteria (e.g. *Clostridium* clusters XIVa and IV) as well as reduced lactate producing bacteria (e.g. *Bifidobacterium adolescentis*) can be correlated with a metabolic disorder. Subsets of a formulation that comprises at least one primary fermenter and at least one secondary fermenter can be used for the treatment and/or mitigate progression of a metabolic health condition, for example, T1DM.

Figure 2:
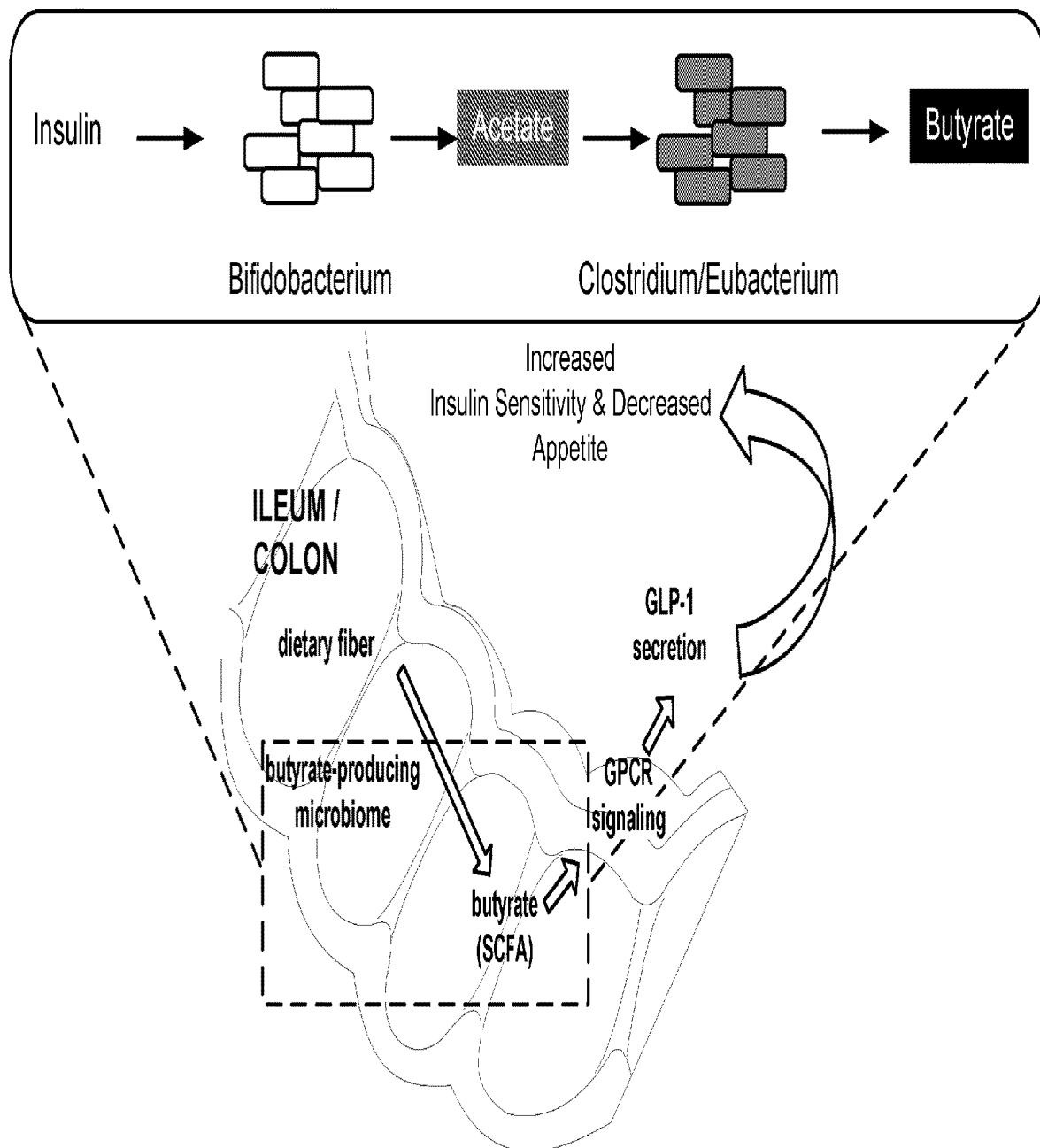
FIG. 2 depicts an illustrative microbiome mediated pathway that can be affected to create a Type 2 Diabetes Mellitus (T2DM) therapeutic. A formulation comprising a prebiotic (e.g. inulin), a primary fermenter (e.g. *Bifidobacterium*), and a secondary fermenter (e.g. *Clostridium* and/or *Eubacterium*) can be used for butyrate production.

FIG. 2 depicts a critical digestive pathway that can impact metabolic-related health conditions. Alteration of the pathway using microbial compositions of the invention can result in treatment. In the colon, dietary fiber can be processed by butyrate-producing microorganisms to produce butyrate (i.e. butanoate), which is a short chain fatty acid (SCFA). In turn, butyrate can initiate G-protein coupled receptor (GPCR) signaling, leading to glucagon-like peptide-1 (GLP-1) secretion which can result in increased insulin sensitivity and/or decreased appetite. By altering the butyrate-producing microbiome in a subject, e.g. with T2DM or insulin insensitivity, the pathway can be stimulated. In some patients, insulin sensitivity can be increased and/or restored to pre-diabetic levels with a microbial composition.

In some aspects of the invention, strains of interest are chosen by identifying a superset of bacteria that play a role in the functional pathway that leads to GLP-1 production (e.g. bacteria that have butyrate kinase, butyrate coenzyme A (CoA), and/or butyrate CoA transferase genes).

Butyrate kinase is an enzyme that can belong to a family of transferases, for example those transferring phosphorus-containing groups (e.g., phosphotransferases) with a carboxy group as acceptor. The systematic name of this enzyme class can be ATP:butanoate 1-phosphotransferase. Butyrate kinase can participate in butyrate metabolism. Butyrate kinase can catalyze the following reaction:

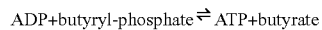

ADP+butyryl-phosphate ⇌ ATP+butyrate

Butyrate-Coenzyme A, also butyryl-coenzyme A, can be a coenzyme A-activated form of butyric acid. It can be acted upon by butyryl-CoA dehydrogenase and can be an intermediary compound in acetone-butanol-ethanol fermentation. Butyrate-Coenzyme A can be involved in butyrate metabolism.

Butyrate-Coenzyme A transferase, also known as butyrate-acetoacetate CoA-transferase, can belong to a family of transferases, for example, the CoA-transferases. The systematic name of this enzyme class can be butanoyl-CoA: acetoacetate CoA-transferase. Other names in common use can include butyryl coenzyme A-acetoacetate coenzyme A-transferase, and butyryl-CoA-acetoacetate CoA-transferase. Butyrate-Coenzyme A transferase can catalyze the following chemical reaction:

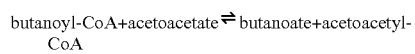

butanoyl-CoA+acetoacetate ⇌ butanoate+acetoacetyl-CoA

Butyryl-CoA dehydrogenase can belong to the family of oxidoreductases, for example, those acting on the CH—CH group of donor with other acceptors. The systematic name of this enzyme class can be butanoyl-CoA:acceptor 2,3-oxidoreductase. Other names in common use can include butyryl dehydrogenase, unsaturated acyl-CoA reductase, ethylene reductase, enoyl-coenzyme A reductase, unsaturated acyl coenzyme A reductase, butyryl coenzyme A dehydrogenase, short-chain acyl CoA dehydrogenase, short-chain acyl-coenzyme A dehydrogenase, 3-hydroxyacyl CoA reductase, and butanoyl-CoA:(acceptor) 2,3-oxidoreductase. Non-limiting examples of metabolic pathways that butyryl-CoA dehydrogenase can participate in include: fatty acid metabolism; valine, leucine and isoleucine degradation; and butanoate metabolism. Butyryl-CoA dehydrogenase can employ one cofactor, FAD. Butyryl-CoA dehydrogenase can catalyze the following reaction:

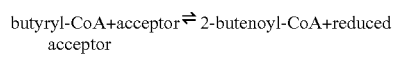

butyryl-CoA+acceptor ⇌ 2-butenoyl-CoA+reduced acceptor

Beta-hydroxybutyryl-CoA dehydrogenase or 3-hydroxybutyryl-CoA dehydrogenase can belong to a family of oxidoreductases, for example, those acting on the CH—OH group of donor with NAD+ or NADP+ as acceptor. The systematic name of the enzyme class can be (S)-3-hydroxybutanoyl-CoA:NADP+ oxidoreductase. Other names in common use can include beta-hydroxybutyryl coenzyme A dehydrogenase, L(+)-3-hydroxybutyryl-CoA dehydrogenase, BHBD, dehydrogenase, L-3-hydroxybutyryl coenzyme A (nicotinamide adenine, dinucleotide phosphate), L-(+)-3-hydroxybutyryl-CoA dehydrogenase, and 3-hydroxybutyryl-CoA dehydrogenase. Beta-hydroxybutyryl-CoA dehydrogenase enzyme can participate in benzoate degradation via coa ligation. Beta-hydroxybutyryl-CoA dehydrogenase enzyme can participate in butanoate metabolism. Beta-hydroxybutyryl-CoA dehydrogenase can catalyze the following reaction:

(S)-3-hydroxybutanoyl-CoA+NADP⁺ ⇌ 3-acetoacetyl-CoA+NADPH+H⁺

Crotonase can comprise enzymes with, for example, dehalogenase, hydratase, isomerase activities. Crotonase can be implicated in carbon-carbon bond formation, cleavage, and hydrolysis of thioesters. Enzymes in the crotonase superfamily can include, for example, enoyl-CoA hydratase which can catalyse the hydratation of 2-trans-enoyl-CoA into 3-hydroxyacyl-CoA; 3-2trans-enoyl-CoA isomerase or dodecenoyl-CoA isomerise (e.g., EC 5.3.3.8), which can shift the 3-double bond of the intermediates of unsaturated fatty acid oxidation to the 2-trans position; 3-hydroxbutyryl-CoA dehydratase (e.g., crotonase; EC 4.2.1.55), which can be involved in the butyrate/butanol-producing pathway; 4-Chlorobenzoyl-CoA dehalogenase (e.g., EC 3.8.1.6) which can catalyze the conversion of 4-chlorobenzoate-CoA to 4-hydroxybenzoate-CoA; dienoyl-CoA isomerase, which can catalyze the isomerisation of 3-trans,5-cis-dienoyl-CoA to 2-trans,4-trans-dienoyl-CoA; naphthoate synthase (e.g., MenB, or DHNA synthetase; EC 4.1.3.36), which can be involved in the biosynthesis of menaquinone (e.g., vitamin K2); carnitine racemase (e.g., gene caiD), which can catalyze the reversible conversion of crotonobetaine to L-carnitine in *Escherichia coli*; Methylmalonyl CoA decarboxylase (e.g., MMCD; EC 4.1.1.41); carboxymethylproline synthase (e.g., CarB), which can be involved in carbapenem biosynthesis; 6-oxo camphor hydrolase, which can catalyze the desymmetrization of bicyclic beta-diketones to optically active keto acids; the alpha subunit of fatty acid oxidation complex, a multi-enzyme complex that can catalyze the last three reactions in the fatty acid beta-oxidation cycle; and AUH protein, which can be a bifunctional RNA-binding homologue of enoyl-CoA hydratase.

Thiolases, also known as acetyl-coenzyme A acetyltransferases (ACAT), can convert two units of acetyl-CoA to acetoacetyl CoA, for example, in the mevalonate pathway. Thiolases can include, for example, degradative thiolases (e.g., EC 2.3.1.16) and biosynthetic thiolases (e.g., EC 2.3.1.9). 3-ketoacyl-CoA thiolase, also called thiolase I, can be involved in degradative pathways such as fatty acid beta-oxidation. Acetoacetyl-CoA thiolase, also called thiolase II, can be specific for the thiolysis of acetoacetyl-CoA and can be involved in biosynthetic pathways such as poly beta-hydroxybutyric acid synthesis or steroid biogenesis. A thiolase can catalyze the following reaction:

As shown in FIG. 2, production of butyrate can involve two major phases or microbes, for example, a primary fermenter and a secondary fermenter. The primary fermenter can produce intermediate molecules (e.g. lactate, acetate) when given an energy source (e.g. fiber). The secondary fermenter can convert the intermediate molecules produced by the primary fermenter into butyrate. Non-limiting examples of primary fermenter include *Akkermansia muciniphila*, *Bifidobacterium adolescentis*, *Bifidobacterium infantis* and *Bifidobacterium longum*. Non-limiting examples of secondary fermenter include *Clostridium beijerinckii*, *Clostridium butyricum*, *Clostridium indolis*, *Eubacterium hallii*, and *Faecalibacterium prausnitzii*. A combination of primary and secondary fermenters can be used to produce butyrate in a subject. Subsets of a formulation that comprises at least one primary fermenter and at least one secondary fermenter can be used for the treatment and/or mitigate progression of a metabolic health condition, for example, T2DM and obesity. The formulation can additionally comprise a prebiotic.

In some embodiments, a therapeutic composition comprises at least one primary fermenter and at least one secondary fermenter. In some embodiments, a therapeutic composition comprises at least one primary fermenter, at least one secondary fermenter, and at least one prebiotic. In one non-limiting example, a therapeutic composition can comprise *Bifidobacterium adolescentis*, *Clostridium indolis*, and inulin. In another non-limiting example, a therapeutic composition can comprise *Bifidobacterium longum*, *Faecalibacterium prausnitzii*, and starch.

*Akkermansia muciniphila* can be a gram negative, strict anaerobe that can play a role in mucin degradation. Levels of *Akkermansia muciniphila* can be reduced in subjects with metabolic disorders, for example, obesity and T2DM. *Akkermansia muciniphila* can protect against metabolic disorder, for example, through increased levels of endocannabinoids that control inflammation, the gut barrier, and gut peptide secretion. *Akkermansia muciniphila* can serve as a primary fermenter.

*Bifidobacterium adolescentis* can be a gram-positive anaerobe, which can be found in healthy human gut from infancy. *Bifidobacterium adolescentis* can synthesize B vitamins. *Bifidobacterium adolescentis* can serve as a primary fermenter.

*Bifidobacterium infantis* can be a gram-positive, catalase negative, micro-aerotolerant anaerobe. *Bifidobacterium infantis* can serve as a primary fermenter.

*Bifidobacterium longum* can be a gram-positive, catalase negative, micro-aerotolerant anaerobe. *Bifidobacterium longum* can serve as a primary fermenter.

*Clostridium beijerinckii* can be a gram-positive, strict anaerobe that belongs to Clostridial cluster I. *Clostridium beijerinckii* can serve as a secondary fermenter.

*Clostridium butyricum* can be a gram-positive, strict anaerobe that can serve as a secondary fermenter.

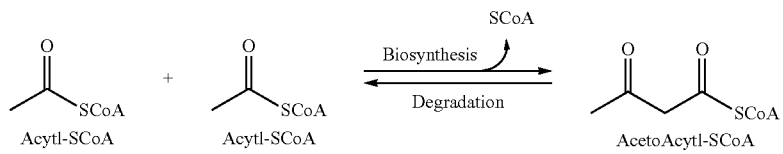

*Clostridium indolis* can be a gram-positive, strict anaerobe that belongs to Clostridial cluster XIVA. *Clostridium indolis* can serve as a secondary fermenter.

*Eubacterium hallii* can be a gram-positive, anaerobe that belongs to Arrangement A Clostridial cluster XIVA. *Eubacterium hallii* can serve as a secondary fermenter.

*Faecalibacterium prausnitzii* can be a gram-positive, anaerobe belonging to Clostridial cluster IV. *Faecalibacterium prausnitzii* can be one of the most common gut bacteria and the largest butyrate producer. *Faecalibacterium prausnitzii* can serve as a secondary fermenter.

Non-limiting examples of genes involved in the generation of butyrate include: butyryl-CoA dehydrogenase, beta-hydroxybutyryl-CoA dehydrogenase or 3-hydroxybutyryl-CoA dehydrogenase, crotonase, electron transfer protein a, electron transfer protein b, and thiolase Measuring the microbiome of hosts can show that microbiomes lacking various strains of microorganisms can result in a health condition and/or disease state (e.g. T2DM and obesity). Restoring one or more lacking strains (e.g. via a bacterial strain such as *E. hallii* or treatment with fermented milk products) can result in alteration of the health condition. Some non-limiting examples include altering the gut microbiome such that the host has an increased capacity for energy harvest, increased insulin sensitivity, and/or decreased appetite.

To treat metabolic conditions, for example, T2DM, obesity, and/or T1DM, one or more of the following microorganisms can be administered to the colon: *Butyrivibrio fibrisolvens, Clostridium acetobutylicum, Clostridium beijerinckii, Faecalibacterium prausnitzii, Roseburia cecicola, Clostridium butyricum, Bifidobacterium infantis, Bifidobacterium longum, Bifidobacterium adolescentis, Streptococcus mutans, Ruminococcus gnavus, Roseburia inulinivorans, Akkermansia muciniphila, Fibrobacter succinogenes, Ruminococcus flavefaciens, Anaerostipes caccae, Eubacterium hallii, Clostridium indolis, Eubacterium rectale*, or any combination thereof. The microorganisms can be administered with a prebiotic.

In some embodiments, a pharmaceutical composition comprising one or more of the following microorganisms are administered for the treatment of metabolic conditions: *Butyrivibrio fibrisolvens, Clostridium acetobutylicum, Clostridium beijerinckii, Faecalibacterium prausnitzii, Roseburia cecicola, Clostridium butyricum, Bifidobacterium infantis, Bifidobacterium longum, Bifidobacterium adolescentis, Streptococcus mutans, Ruminococcus gnavus, Roseburia inulinivorans, Akkermansia muciniphila, Fibrobacter succinogenes, Ruminococcus flavefaciens, Anaerostipes caccae, Eubacterium hallii, Clostridium indolis* and *Eubacterium rectale*. The composition can additionally comprise a prebiotic.

Figure 6:
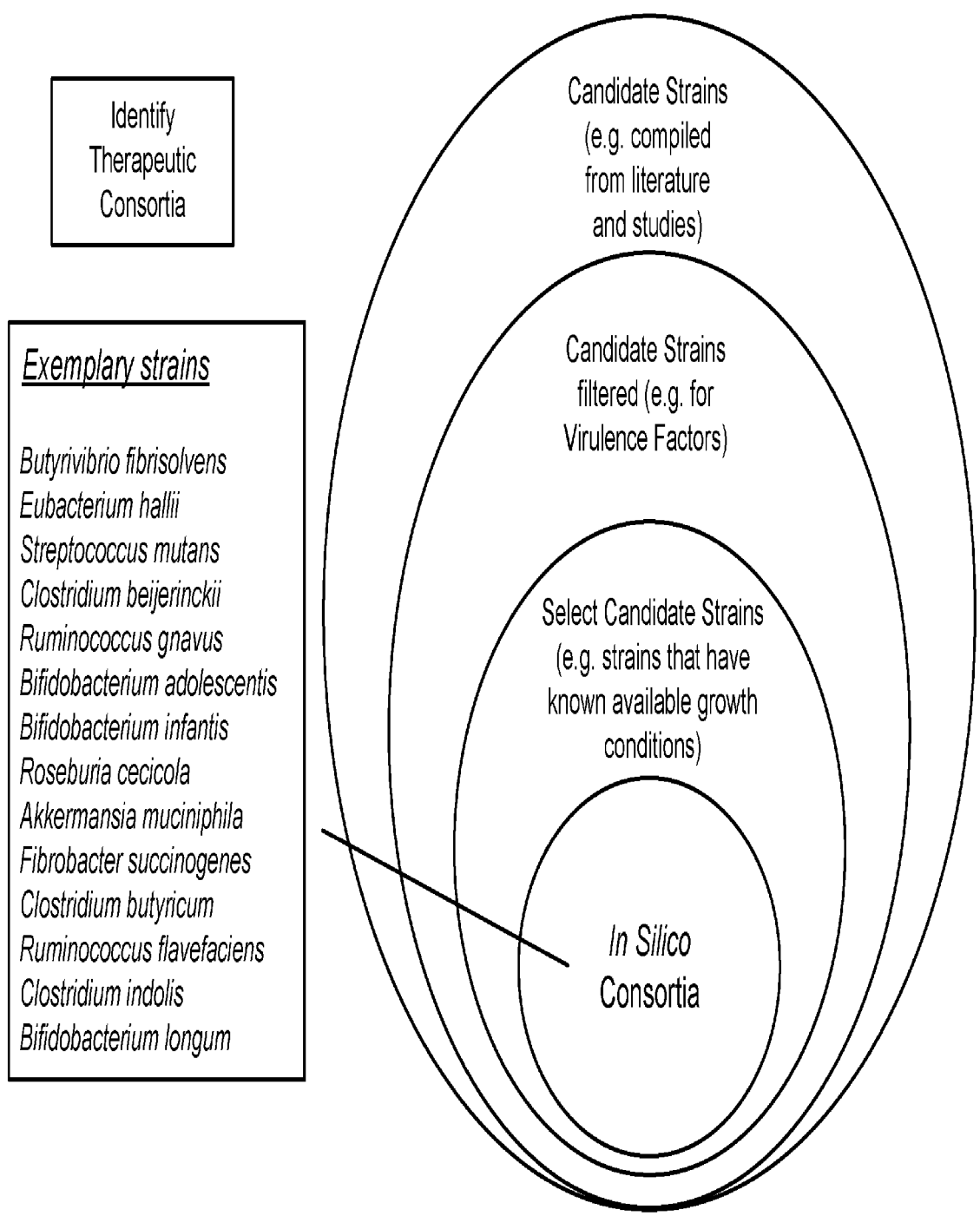
FIG. 6 depicts an exemplary process used to identify strains related to T2DM (e.g. to identify a therapeutic consortia). Exemplary T2DM strains found using this method include: *Butyrivibrio fibrisolvens, Streptococcus mutans, Ruminococcus gnavus, Roseburia cecicola, Fibrobacter succinogenes, Ruminococcus flavefaciens,* and *Clostridium indolis.*

FIG. 6 depicts an exemplary method to identify microorganism strains to be used in the treatment of T2DM. A multi-tiered approach can be used to identify one or more microorganism strains for use as a therapeutic. Candidate strains can be found in scientific literature and studies. Candidate strains can be found by analyzing healthy and unhealthy hosts. Candidate strains can be filtered and/or selected for the ability to be administered to a patient (e.g. biosafety level, availability to be manufactured, growth conditions). Finally, an in silico consortia can be determined.

In some embodiments, the prebiotic and probiotic consortia are chosen to create an entirely self-sufficient system that does not require any external input. For example, a subject with T2DM can be treated with a combination of SCFA-producing probiotics and prebiotics comprising dietary fiber and other agents required for the activity of the SCFA-producing probiotics. In this manner, the prebiotic and probiotic form a self-sufficient system, wherein the probiotic converts the prebiotic dietary fiber to SCFAs (butyrate, acetate, propionate), which can trigger downstream signaling for controlling obesity, diabetes and promote weigh loss in the subject.

Also provided are methods to generate probiotics against a subject's microbiome composition. The microbiome composition can have an effect on the subject's disease status and clinical treatment response. Compositions of the disclosure can be tailored to suit the microbiome composition of a subject for effective treatment of symptoms associated with a health condition. For example, therapeutic formulations for obese individuals can differ from therapeutic formulations for non-obese individuals for the treatment of a specific disorder based on differences in their microbiota.

In some embodiments, methods for achieving weight loss by targeting rebalancing of the gut microbiome comprise: using specific probiotic strains, using appropriate prebiotics, diet recommendation, and periodic monitoring. For example, the weight loss methods can comprise replacing prevotellas (a group within the Bacteroidetes phylum) and selenomonas from the microbiomes of overweight subjects with native probiotic strains from a healthy subject. Prebiotics can comprise dietary fiber and agents required for sustenance of the native probiotics.

Also provided are methods of formulating prebiotics and/or probiotic combinations to treat health conditions. A composition comprising prebiotics and/or probiotics can prevent, for example, gastrointestinal infections through production of antimicrobial factors, stimulation of the host immune system, and/or competition with pathogens for nutrients or host binding sites. A combination of probiotics and prebiotics can provide a complete system for producing amino acids, polyphenols, vitamins, and other compounds of nutritive value in a subject.

Microbe Compositions

In one aspect of the invention, a strain consortia comprising one or more microorganisms selected from the group consisting of: *Akkermansia muciniphila, Anaerostipes caccae, Bifidobacterium adolescentis, Bifidobacterium bifidum, Bifidobacterium infantis, Bifidobacterium longum, Butyrivibrio fibrisolvens, Clostridium acetobutylicum, Clostridium aminophilum, Clostridium beijerinckii, Clostridium butyricum, Clostridium colinum, Clostridium indolis, Clostridium orbiscindens, Enterococcus faecium, Eubacterium hallii, Eubacterium rectale, Faecalibacterium prausnitzii, Fibrobacter succinogenes, Lactobacillus acidophilus, Lactobacillus brevis, Lactobacillus bulgaricus, Lactobacillus casei, Lactobacillus caucasicus, Lactobacillus fermentum, Lactobacillus helveticus, Lactobacillus lactis, Lactobacillus plantarum, Lactobacillus reuteri, Lactobacillus rhamnosus, Oscillospira guilliermondii, Roseburia cecicola, Roseburia inulinivorans, Ruminococcus flavefaciens, Ruminococcus gnavus, Ruminococcus obeum, Streptococcus cremoris, Streptococcus faecium, Streptococcus infantis, Streptococcus mutans, Streptococcus thermophilus, Anaerofustis stercorihominis, Anaerostipes hadrus, Anaerotruncus colihominis, Clostridium sporogenes, Clostridium tetani, Coprococcus, Coprococcus eutactus, Eubacterium cylindroides, Eubacterium dolichum, Eubacterium ventriosum, Roseburia faeccis, Roseburia hominis, Roseburia intestinalis*, and any combination thereof, can be used to treat a metabolic disorder such as obesity or T2DM.

A therapeutic consortium can comprise one or more microorganisms selected from the group consisting of:

*Akkermansia muciniphila, Anaerostipes caccae, Bifidobacterium adolescentis, Bifidobacterium bifidum, Bifidobacterium infantis, Bifidobacterium longum, Butyrivibrio fibrisolvens, Clostridium acetobutylicum, Clostridium aminophilum, Clostridium beijerinckii, Clostridium butyricum, Clostridium colinum, Clostridium indolis, Clostridium orbiscindens, Enterococcus faecium, Eubacterium hallii, Eubacterium rectale, Faecalibacterium prausnitzii, Fibrobacter succinogenes, Lactobacillus acidophilus, Lactobacillus brevis, Lactobacillus bulgaricus, Lactobacillus casei, Lactobacillus caucasicus, Lactobacillus fermentum, Lactobacillus helveticus, Lactobacillus lactis, Lactobacillus plantarum, Lactobacillus reuteri, Lactobacillus rhamnosus, Oscillospira guilliermondii, Roseburia cecicola, Roseburia inulinivorans, Ruminococcus flavefaciens, Ruminococcus gnavus, Ruminococcus obeum, Streptococcus cremoris, Streptococcus faecium, Streptococcus infantis, Streptococcus mutans, Streptococcus thermophilus, Anaerofustis stercorihominis, Anaerostipes hadrus, Anaerotruncus colihominis, Clostridium sporogenes, Clostridium tetani, Coprococcus, Coprococcus eutactus, Eubacterium cylindroides, Eubacterium dolichum, Eubacterium ventriosum, Roseburia faeccis, Roseburia hominis, Roseburia intestinalis*, and any combination thereof.

In one aspect of the invention, microbe compositions comprising one or more microorganisms selected from the group consisting of: *Akkermansia muciniphila, Anaerostipes caccae, Bifidobacterium adolescentis, Bifidobacterium bifidum, Bifidobacterium infantis, Bifidobacterium longum, Butyrivibrio fibrisolvens, Clostridium acetobutylicum, Clostridium aminophilum, Clostridium beijerinckii, Clostridium butyricum, Clostridium colinum, Clostridium indolis, Clostridium orbiscindens, Enterococcus faecium, Eubacterium hallii, Eubacterium rectale, Faecalibacterium prausnitzii, Fibrobacter succinogenes, Lactobacillus acidophilus, Lactobacillus brevis, Lactobacillus bulgaricus, Lactobacillus casei, Lactobacillus caucasicus, Lactobacillus fermentum, Lactobacillus helveticus, Lactobacillus lactis, Lactobacillus plantarum, Lactobacillus reuteri, Lactobacillus rhamnosus, Oscillospira guilliermondii, Roseburia cecicola, Roseburia inulinivorans, Ruminococcus flavefaciens, Ruminococcus gnavus, Ruminococcus obeum, Streptococcus cremoris, Streptococcus faecium, Streptococcus infantis, Streptococcus mutans, Streptococcus thermophilus, Anaerofustis stercorihominis, Anaerostipes hadrus, Anaerotruncus colihominis, Clostridium sporogenes, Clostridium tetani, Coprococcus, Coprococcus eutactus, Eubacterium cylindroides, Eubacterium dolichum, Eubacterium ventriosum, Roseburia faeccis, Roseburia hominis, Roseburia intestinalis*, and any combination thereof, can be used to treat a metabolic disorder such as obesity or T2DM.

In some embodiments, provided are therapeutic compositions to treat a metabolic disorder comprising a purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23S rRNA of a microorganism selected from the group consisting of: *Akkermansia muciniphila, Anaerostipes caccae, Bifidobacterium adolescentis, Bifidobacterium bifidum, Bifidobacterium infantis, Bifidobacterium longum, Butyrivibrio fibrisolvens, Clostridium acetobutylicum, Clostridium aminophilum, Clostridium beijerinckii, Clostridium butyricum, Clostridium colinum, Clostridium indolis, Clostridium orbiscindens, Enterococcus faecium, Eubacterium hallii, Eubacterium rectale, Faecalibacterium prausnitzii, Fibrobacter succinogenes, Lactobacillus acidophilus, Lactobacillus brevis, Lactobacillus bulgaricus, Lactobacillus casei, Lactobacillus caucasicus, Lactobacillus fermentum, Lactobacillus helveticus, Lactobacillus lactis, Lactobacillus plantarum, Lactobacillus reuteri, Lactobacillus rhamnosus, Oscillospira guilliermondii, Roseburia cecicola, Roseburia inulinivorans, Ruminococcus flavefaciens, Ruminococcus gnavus, Ruminococcus obeum, Streptococcus cremoris, Streptococcus faecium, Streptococcus infantis, Streptococcus mutans, Streptococcus thermophilus, Anaerofustis stercorihominis, Anaerostipes hadrus, Anaerotruncus colihominis, Clostridium sporogenes, Clostridium tetani, Coprococcus, Coprococcus eutactus, Eubacterium cylindroides, Eubacterium dolichum, Eubacterium ventriosum, Roseburia faeccis, Roseburia hominis, Roseburia intestinalis*, and any combination thereof.

In some embodiments, provided are therapeutic compositions to treat a metabolic disorder comprising an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23S rRNA of a microorganism selected from the group consisting of: *Akkermansia muciniphila, Bifidobacterium adolescentis, Bifidobacterium infantis, Bifidobacterium longum, Clostridium beijerinckii, Clostridium butyricum, Clostridium indolis, Eubacterium hallii*, and any combination thereof.

In some embodiments, provided are therapeutic compositions to treat a metabolic disorder comprising an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23S rRNA of a microorganism selected from the group consisting of: *Akkermansia muciniphila, Bifidobacterium adolescentis, Bifidobacterium infantis, Bifidobacterium longum, Clostridium beijerinckii, Clostridium butyricum, Clostridium indolis, Eubacterium hallii, Faecalibacterium prausnitzii*, and any combination thereof.

In some embodiments, provided are therapeutic compositions to treat a metabolic disorder comprising an isolated and/or purified microorganism population comprising bacteria selected from the group consisting of: *Akkermansia muciniphila, Bifidobacterium adolescentis, Bifidobacterium infantis, Bifidobacterium longum, Clostridium beijerinckii, Clostridium butyricum, Clostridium indolis, Eubacterium hallii*, and any combination thereof.

In some embodiments, provided are therapeutic compositions to treat a metabolic disorder comprising an isolated and/or purified microorganism population comprising bacteria selected from the group consisting of: *Akkermansia muciniphila, Bifidobacterium adolescentis, Bifidobacterium infantis, Bifidobacterium longum, Clostridium beijerinckii, Clostridium butyricum, Clostridium indolis, Eubacterium hallii, Faecalibacterium prausnitzii*, and any combination thereof.

In some embodiments, a therapeutic consortium comprises *Akkermansia muciniphila, Bifidobacterium adolescentis, Bifidobacterium infantis, Bifidobacterium longum, Clostridium beijerinckii, Clostridium butyricum, Clostridium indolis*, and *Eubacterium* hallii.

In some embodiments, a therapeutic consortium comprises *Akkermansia muciniphila, Bifidobacterium adolescentis, Bifidobacterium infantis, Bifidobacterium longum, Clostridium beijerinckii, Clostridium butyricum, Clostridium indolis, Eubacterium hallii*, and *Faecalibacterium prausnitzii*.

In some embodiments, a therapeutic consortium consists essentially of *Akkermansia muciniphila*, *Bifidobacterium adolescentis*, *Bifidobacterium infantis*, *Bifidobacterium longum*, *Clostridium beijerinckii*, *Clostridium butyricum*, *Clostridium indolis*, and *Eubacterium hallii*.

In some embodiments, a therapeutic consortium consists essentially of *Akkermansia muciniphila*, *Bifidobacterium adolescentis*, *Bifidobacterium infantis*, *Bifidobacterium longum*, *Clostridium beijerinckii*, *Clostridium butyricum*, *Clostridium indolis*, *Eubacterium hallii*, and *Faecalibacterium prausnitzii*.

In one embodiment, a therapeutic composition to treat a metabolic disorder comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Akkermansia muciniphila*.

In one embodiment, a therapeutic composition to treat a metabolic disorder comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23S rRNA of *Anaerostipes caccae*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Bifidobacterium adolescentis*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Bifidobacterium bifidum*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Bifidobacterium infantis*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Bifidobacterium longum*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Butyrivibrio fibrisolvens*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23S rRNA of *Clostridium acetobutylicum*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23S rRNA of *Clostridium aminophilum*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23S rRNA of *Clostridium beijerinckii*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23S rRNA of *Clostridium butyricum*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23S rRNA of *Clostridium colinum*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23S rRNA of *Clostridium indolis*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23S rRNA of *Clostridium orbiscindens*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Enterococcus faecium*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Eubacterium hallii*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Eubacterium rectale*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Faecalibacterium prausnitzii*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Fibrobacter succinogenes*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Lactobacillus acidophilus*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Lactobacillus brevis*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Lactobacillus bulgaricus*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Lactobacillus casei*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Lactobacillus caucasicus*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Lactobacillus fermentum*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Lactobacillus helveticus*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Lactobacillus lactis*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Lactobacillus plantarum*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Lactobacillus reuteri*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Lactobacillus rhamnosus*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Oscillospira guilliermondii*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Roseburia cecicola*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Roseburia inulinivorans*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Ruminococcus flavefaciens*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Ruminococcus gnavus*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Ruminococcus obeum*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Streptococcus cremoris*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA *Streptococcus faecium*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Streptococcus infantis*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Streptococcus mutans*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Streptococcus thermophilus*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Anaerofustis stercorihominis*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Anaerostipes hadrus*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Anaerotruncus colihominis*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23S rRNA of *Clostridium sporogenes*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23S rRNA of *Clostridium sporogenes*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23S rRNA of *Clostridium tetani*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23S rRNA of *Clostridium tetani*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23S rRNA of *Coprococcus*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23S rRNA of *Coprococcus eutactus*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Eubacterium cylindroides*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Eubacterium dolichum*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Eubacterium ventriosum*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Roseburia faeccis*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Roseburia hominis*.

In one embodiment, a therapeutic composition comprises an isolated and/or purified microorganism population consisting of bacteria with at least about: 70%, 75%, 80%, 85%, 87%, 90%, 91%, 92%, 93%, 94%, 95%, 96%, 97%, 98%, 99%, 99.5%, or 100% sequence identity to the 16SrRNA and/or 23 S rRNA of *Roseburia intestinalis*.

A therapeutic composition may comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, or at least 50, or at least 75, or at least 100 types of bacteria. A therapeutic composition may comprise at most 1, at most 2, at most 3, at most 4, at most 5, at most 6, at most 7, at most 8, at most 9, at most 10, at most 11, at most 12, at most 13, at most 14, at most 15, at most 16, at most 17, at most 18, at most 19, at most 20, at most 21, at most 22, at most 23, at most 24, at most 25, at most 26, at most 27, at most 28, at most 29, at most 30, at most 31, at most 32, at most 33, at most 34, at most 35, at most 36, at most 37, at most 38, at most 39, at most 40, at most 45, or at most 50, or at most 75, or at most 100 types of bacteria.

Figure 9:
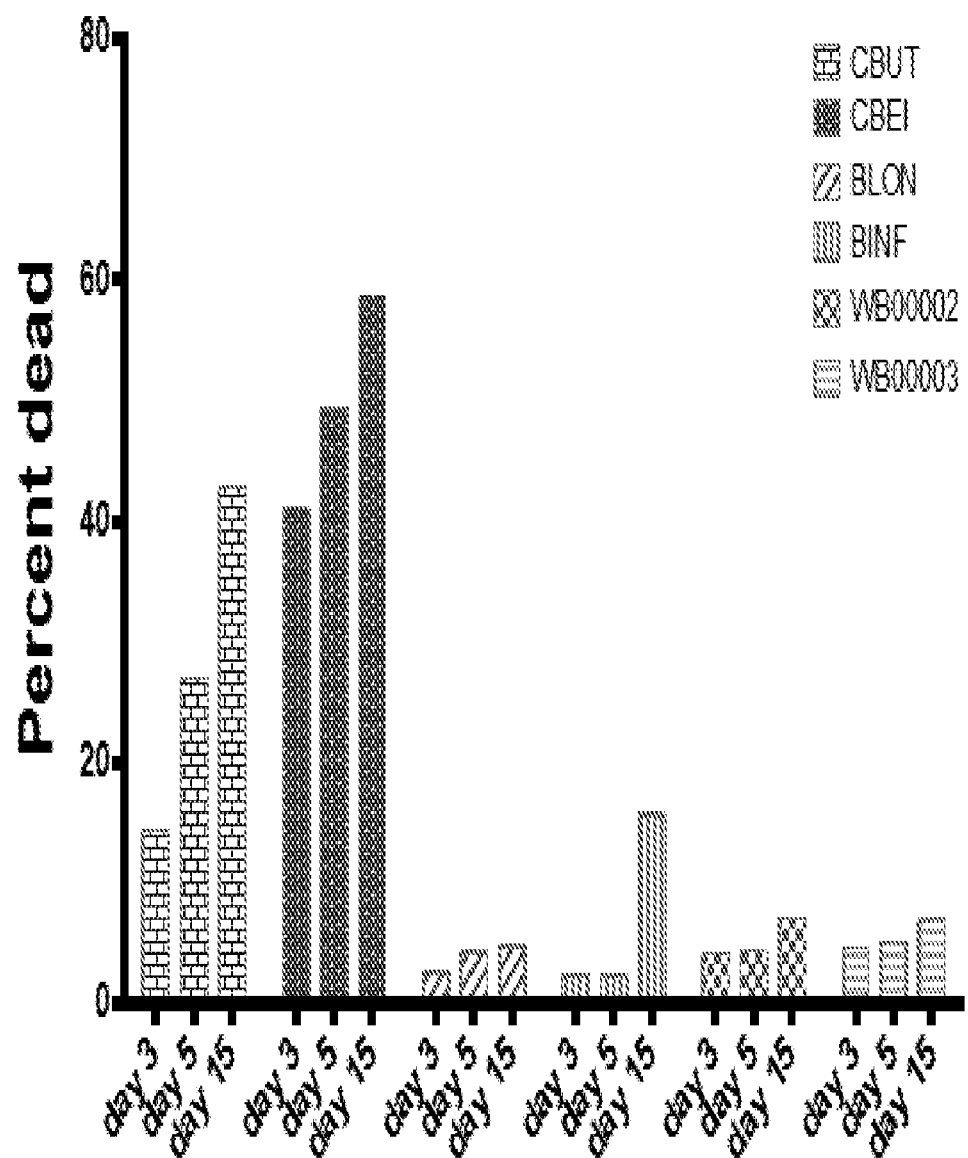
FIG. 9 depicts how by combining strains together in a formulation the stability of all of the individual strains either can remain high or dramatically improve. Stability of individual strains, *Clostridium butyricum* (CBUT), *Clostridium beijerinckii* (CBEI), *Bifidobacterium longum* (BLON), and *Bifidobacterium infantis* (BINF) was compared with formulations WB00002 and WB00003, which can comprise strains CBUT, CBEI, BLON, BINF present together in the formulation. The formulations can additionally comprise strains *B. adolescentis, A. muciniphila, E. hallii,* and *C. indolis*. Formulations WB0002 and WB0003 differ in that WB0003 can also comprise a prebiotic in combination with the strains. The increased stability of the formulations suggests that the formulation can provide a synergistic stability when the strains are together over individual strains.
Figure 10:
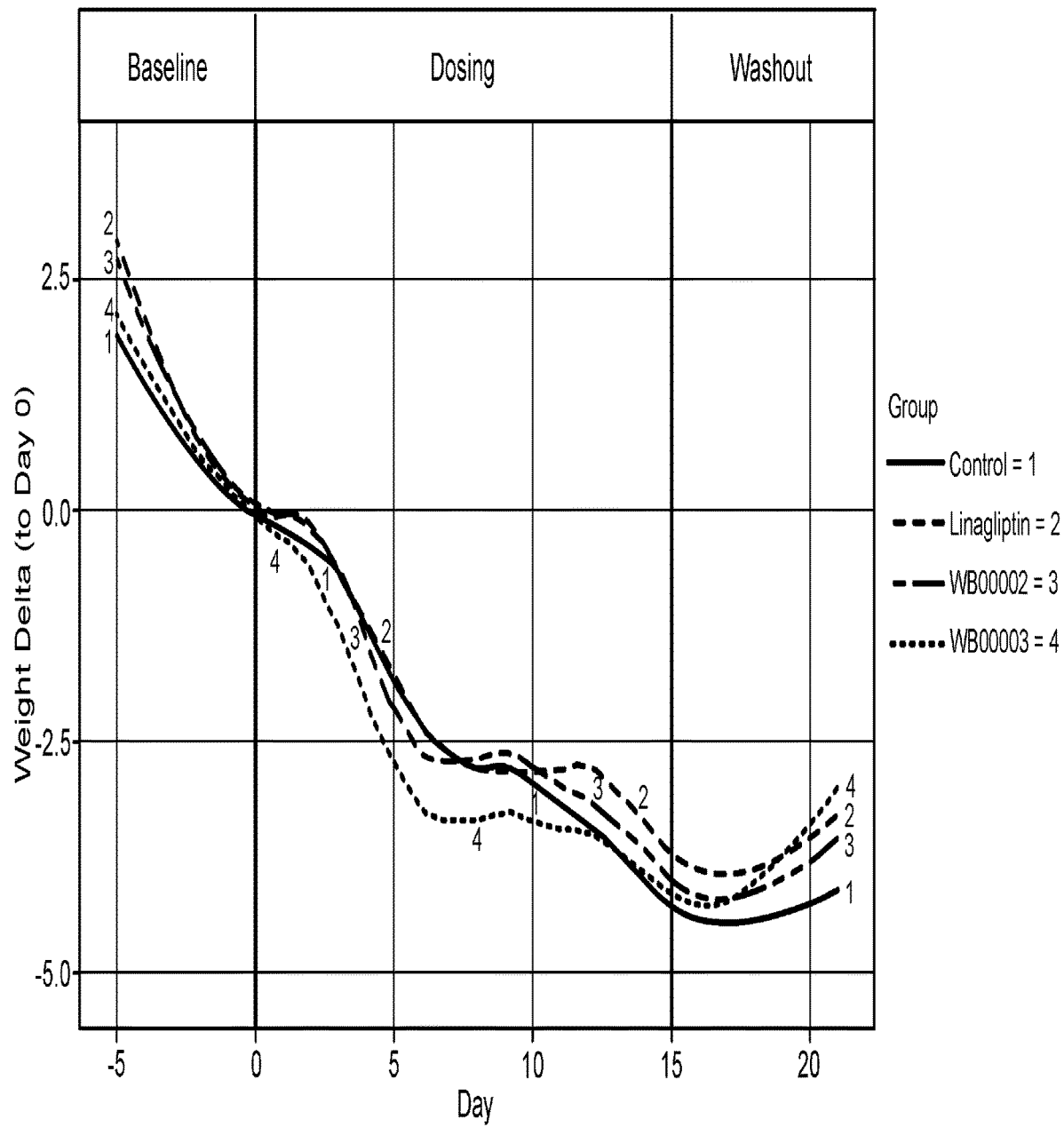
FIG. 10 depicts how formulation WB0003 can result in increased weight loss during the dosing period of a preclinical study involving diet-induced obese mice. Support of this effect is further corroborated by the weight regain during the washout period. Linagliptin is a positive control.
Figure 11:
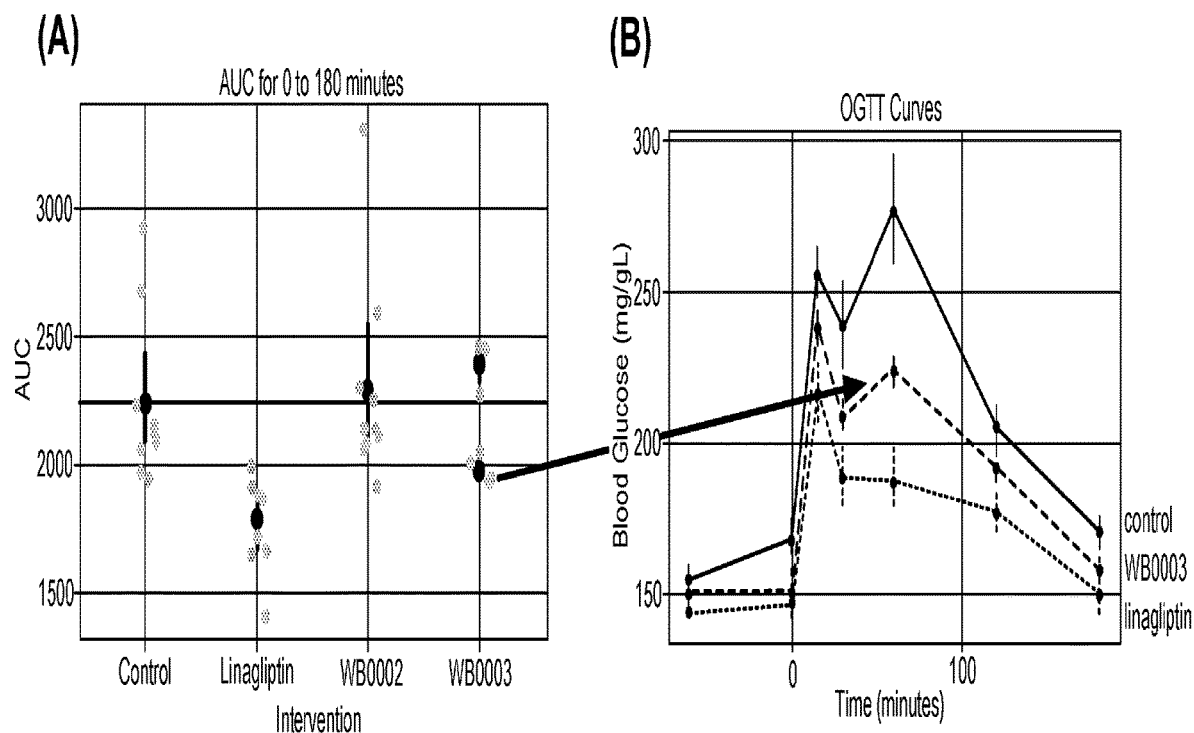
FIG. 11 (A) depicts a bi-modal response in glucose control as measured by Area Under the Oral Glucose Tolerance Test (OGTT) Curve (AUC) for mice dosed with formulation WB0003. (B) Depicts the OGTT curves that compare the responders to WB0003, to control, and to the positive control, Linagliptin.

In some embodiments, combining one or more microbes in a therapeutic composition or consortia increases or maintains the stability of the microbes in the composition compared with the stability of the microbes alone as illustrated in FIG. 9. A therapeutic consortium of microbes can provide a synergistic stability compared with the individual strains.

In some embodiments, combining one or more microbes in a therapeutic composition or consortia can provide a synergistic effect when administered to the individual. For example, administration of a first microbe may be beneficial to a subject and administration of a second microbe may be beneficial to a subject but when the two microbes are administered together to a subject, the benefit is greater than the either benefit alone.

Different types of microbes in a therapeutic composition can be present in the same amount or in different amounts. For example, the ratio of two bacteria in a therapeutic composition can be about 1:1, 1:2, 1:5, 1:10, 1:25, 1:50, 1:100, 1:1000, 1:10,000, or 1:100,000.

In some embodiments, a therapeutic composition comprises at least one primary fermenter and at least one secondary fermenter. In some embodiments, a therapeutic composition comprises at least one primary fermenter, at least one secondary fermenter, and at least one prebiotic. In one example, a therapeutic composition can comprise *Clostridium indolis, Bifidobacterium adolescentis*, and inulin. In another example, a therapeutic composition can comprise *Faecalibacterium prausnitzii, Bifidobacterium longum*, and starch.

Microorganisms of the invention can be produced in any suitable medium for growth, some non-limiting examples include: RCM, GYT veg, BHI, PYGveg, nutrient media, minimal media, selective media, differential media, and transport media. The growth medium can comprise a trace mineral. The growth medium can comprise a salt. The growth medium can comprise a vitamin. The growth medium can comprise a buffer. The pH of a growth medium can be, for example, about 7. The pH of a growth medium can be, for example, about 3, about, 4, about, 5, about 6, about 7, or about 8. The growth medium can improve the maximum density a microbial strain can grow to. The growth medium can allow for higher strain concentrations. The growth medium can buffer acid production by a microbial strain, which can minimize the inhibitory effect of, for example, very low pH.

Table 1 shows trace minerals that can be added to a growth media:

TABLE 1

| Trace minerals | |
|---|---|
| Trace minerals component | mg/L medium |
| $CoCl_2$ | 0.65 |
| $CuCl_2*2H_2O$ | 0.03 |
| $H_3BO_3$ | 3.52 |
| $FeSO_4*7H_2O$ | 1.50 |
| $MnCl_2*4H_2O$ | 0.26 |
| $Na_2EDTA$ | 25.01 |
| $Na_2MoO_4*2H_2O$ | 0.80 |
| $Na_2SeO_3$ | 0.39 |
| $NiCl_2$ | 0.65 |
| $ZnSO_4*7H_2O$ | 0.29 |

Table 2 shows vitamins that can be added to a growth media. The concentrations shown in Table 2 can be final concentrations in the growth media.

TABLE 2

| Vitamin solution. | |
|---|---|
| Vitamin Solution component | mg/L medium |
| D-biotin | 0.2 |
| Ca-pantothenate | 2.5 |
| myoinositol | 20 |
| p-aminobenzoic acid | 0.5 |
| pyridoxine hydrochloride | 5 |
| riboflavine | 0.5 |
| thiamine dichloride | 10 |
| vitamin B12 | 0.2 |
| nicotinic acid | 5 |

Table 3 shows an illustrative growth medium:

TABLE 3

| Illustrative growth medium recipe | |
|---|---|
| GYTveg broth (per liter): Component | Amount |
| Glucose | 10 g |
| HiVeg Hydrolysate | 5 g |
| Yeast Extract | 10 g |

TABLE 3-continued

| Illustrative growth medium recipe | |
|---|---|
| GYTveg broth (per liter): Component | Amount |
| Na-thioglycolate | 0.5 g |
| Resazurin | 80 μl (of 14 g/l stock) |
| Vitamin solution | 10 ml |
| Agar (for solid medium) | 18 g |

Table 4 shows an illustrative growth medium.

TABLE 4

| Illustrative growth medium recipe | |
|---|---|
| GYTveg + $CaCO_3$ (per liter): Component | Amount |
| Glucose | 10 g |
| HiVeg Hydrolysate | 5 g |
| Yeast Extract | 10 g |
| Na-thioglycolate | 0.5 g |
| Resazurin | 80 μl (of 14 g/l stock) |
| Vitamin solution | 10 ml |
| $CaCO_3$ | 20 g |
| Agar (for solid medium) | 18 g |

Table 5 shows an illustrative growth medium.

TABLE 5

| Illustrative growth medium recipe | |
|---|---|
| PYGveg Component | Amount per liter |
| Glucose | 5 g |
| $K_2HPO_4$ | 2 g |
| Tween 80 | 1 ml |
| Cystein-HCl | 0.5 g |
| Yeast extract | 10 g |
| HiVeg Extract | 5 g |
| HiVeg Peptone #1 | 5 g |
| HiVeg Peptone #3 | 5 g |
| Vitamin Mix 100x | 10 ml |
| Salt solution | 40 ml |

Table 6 shows illustrative salts that can be added to a growth medium. The concentrations shown in Table 6 can be final concentrations in the growth medium.

TABLE 6

| Salt solution | |
|---|---|
| Salt solution Component | grams per liter |
| $CaCl_2$ $2H_2O$ | 0.02 |
| $MgSO_4$ $7H_2O$ | 0.02 |
| $K_2HPO_4$ | 0.04 |
| $KH_2PO_4$ | 0.04 |
| $NaHCO_3$ | 0.4 |
| NaCl | 0.08 |

In some embodiments, the growth medium comprises PYGveg (e.g., Table 5), vitamins (e.g., Table 2), salt (e.g., Table 6), and a buffer.

Pharmaceutical Formulations

Provided herein are compositions that may be administered as therapeutics and/or cosmetics. One or more microorganisms described herein can be used to create a pharmaceutical formulation comprising an effective amount of the composition for treating a subject. The microorganisms can be in any formulation known in the art. Some non-limiting examples can include topical, capsule, pill, enema, liquid, injection, and the like. In some embodiments, the one or more strains disclosed herein may be included in a food or beverage product, cosmetic, or nutritional supplement.

The formulation can include one or more active ingredients. Active ingredients can be selected from the group consisting of: antibiotics, prebiotics, probiotics, glycans (e.g., as decoys that would limit specific bacterial/viral binding to the intestinal wall), bacteriophages, microorganisms and the like.

In some embodiments, the formulation comprises a prebiotic. In some embodiments, the prebiotic is inulin. The inulin can serve as an energy source for the microbial formulation.

A formulation can be administered by a suitable method for delivery to any part of the gastrointestinal tract of a subject including oral cavity, mouth, esophagus, stomach, duodenum, small intestine regions including duodenum, jejunum, ileum, and large intestine regions including cecum, colon, rectum, and anal canal. In some embodiments, the composition is formulated for delivery to the ileum and/or colon regions of the gastrointestinal tract.

In some embodiments, administration of a formulation occurs orally, for example, through a capsule, pill, powder, tablet, gel, or liquid, designed to release the composition in the gastrointestinal tract. In some embodiments, administration of a formulation occurs by injection, for example, for a formulation comprising butyrate, propionate, acetate, and short-chain fatty acids. In some embodiments, the administration of a formulation occurs by application to the skin, for example, cream, liquid, or patch. In some embodiments, administration of a formulation occurs by a suppository and/or by enema. In some embodiments, a combination of administration routes is utilized.

Microbial compositions can be formulated as a dietary supplement. Microbial compositions can be incorporated with vitamin supplements. Microbial compositions can be formulated in a chewable form such as a probiotic gummy. Microbial compositions can be incorporated into a form of food and/or drink. Non-limiting examples of food and drinks where the microbial compositions can be incorporated include, for example, bars, shakes, juices, infant formula, beverages, frozen food products, fermented food products, and cultured dairy products such as yogurt, yogurt drink, cheese, *acidophilus* drinks, and kefir.

A formulation of the disclosure can be administered as part of a fecal transplant process. A formulation can be administered to a subject by a tube, for example, nasogastric tube, nasojejunal tube, nasoduodenal tube, oral gastric tube, oral jejunal tube, or oral duodenal tube. A formulation can be administered to a subject by colonoscopy, endoscopy, sigmoidoscopy, and/or enema.

In some embodiments, the microbial composition is formulated such that the one or more microbes can replicate once they are delivered to the target habitat (e.g. the gut). In one non-limiting example, the microbial composition is formulated in a pill, such that the pill has a shelf life of at least 1, 2, 3, 4, 5, 6, 7, 8, 9, 10, 11, or 12 months. In another non-limiting example, the storage of the microbial composition is formulated so that the microbes can reproduce once they are in the gut. In some embodiments, other components may be added to aid in the shelf life of the microbial composition. In some embodiments, one or more microbes may be formulated in a manner that it is able to survive in a non-natural environment. For example, a microbe that is native to the gut may not survive in an oxygen-rich environment. To overcome this limitation, the microbe may be formulated in a pill that can reduce or eliminate the exposure to oxygen. Other strategies to enhance the shelf-life of microbes may include other microbes (e.g. if the bacterial consortia comprises a composition whereby one or more strains is helpful for the survival of one or more strains).

In some embodiments, a microbial composition is lyophilized (e.g., freeze-dried) and formulated as a powder, tablet, enteric-coated capsule (e.g. for delivery to ileum/colon), or pill that can be administered to a subject by any suitable route. The lyophilized formulation can be mixed with a saline or other solution prior to administration.

In some embodiments, a microbial composition is formulated for oral administration, for example, as an enteric-coated capsule or pill, for delivery of the contents of the formulation to the ileum and/or colon regions of a subject.

In some embodiments, the microbial composition is formulated for oral administration. In some embodiments, the microbial composition is formulated as an enteric-coated pill or capsule for oral administration. In some embodiments, the microbial composition is formulated for delivery of the microbes to the ileum region of a subject. In some embodiments, the microbial composition is formulated for delivery of the microbes to the colon region (e.g. upper colon) of a subject. In some embodiments, the microbial composition is formulated for delivery of the microbes to the ileum and colon regions of a subject.

An enteric-coating can protect the contents of the oral formulation, for example, pill or capsule, from the acidity of the stomach and provide delivery to the ileum and/or upper colon regions. Non-limiting examples of enteric coatings include pH sensitive polymers (e.g., eudragit FS30D), methyl acrylate-methacrylic acid copolymers, cellulose acetate succinate, hydroxy propyl methyl cellulose phthalate, hydroxy propyl methyl cellulose acetate succinate (e.g., hypromellose acetate succinate), polyvinyl acetate phthalate (PVAP), methyl methacrylate-methacrylic acid copolymers, shellac, cellulose acetate trimellitate, sodium alginate, zein, other polymers, fatty acids, waxes, shellac, plastics, and plant fibers. In some embodiments, the enteric coating is formed by a pH sensitive polymer. In some embodiments, the enteric coating is formed by eudragit FS30D.

The enteric coating can be designed to dissolve at any suitable pH. In some embodiments, the enteric coating is designed to dissolve at a pH greater than about pH 6.5 to about pH 7.0. In some embodiments, the enteric coating is designed to dissolve at a pH greater than about pH 6.5. In some embodiments, the enteric coating is designed to dissolve at a pH greater than about pH 7.0. The enteric coating can be designed to dissolve at a pH greater than about: 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, or 7.5 pH units.

In some embodiments, the administration of a formulation of the disclosure can be preceded by, for example, colon cleansing methods such as colon irrigation/hydrotherapy, enema, administration of laxatives, dietary supplements, dietary fiber, enzymes, and magnesium.

In some embodiments, the microbes are formulated as a population of spores. Spore-containing formulations can be administered by any suitable route described herein. Orally administered spore-containing formulations can survive the low pH environment of the stomach. The amount of spores employed can be, for example, from about 1% w/w to about 99% w/w of the entire formulation.

Formulations provided herein can include the addition of one or more agents to the therapeutics or cosmetics in order to enhance stability and/or survival of the microbial formulation. Non-limiting example of stabilizing agents include genetic elements, glycerin, ascorbic acid, skim milk, lactose, tween, alginate, xanthan gum, carrageenan gum, mannitol, palm oil, and poly-L-lysine (POPL).

In some embodiments, a formulation comprises one or more recombinant microbes or microbes that have been genetically modified. In other embodiments, one or more microbes are not modified or recombinant. In some embodiments, the formulation comprises microbes that can be regulated, for example, a microbe comprising an operon or promoter to control microbial growth. Microbes of the invention can be produced, grown, or modified using any suitable methods, including recombinant methods.

A formulation can be customized for a subject. A custom formulation can comprise, for example, a prebiotic, a probiotic, an antibiotic, or a combination of active agents described herein. Data specific to the subject comprising for example age, gender, and weight can be combined with an analysis result to provide a therapeutic agent customized to the subject. For example, a subject's microbiome found to be low in a specific microbe relative to a sub-population of healthy subjects matched for age and gender can be provided with a therapeutic and/or cosmetic formulation comprising the specific microbe to match that of the sub-population of healthy subjects having the same age and gender as the subject.

In some embodiments, a formulation is administered before, during, and/or after treatment with an antimicrobial agent such as an antibiotic. For example, the formulation can be administered at least about 1 hour, 2 hours, 5 hours, 12 hours, 1 day, 3 days, 1 week, 2 weeks, 1 month, 6 months, or 1 year before and/or after treatment with an antibiotic. The formulation can be administered at most 1 hour, 2 hours, 5 hours, 12 hours, 1 day, 3 days, 1 week, 2 weeks, 1 month, 6 months, or 1 year before and/or after treatment with an antibiotic.

In some embodiments, the formulation is administered after treatment with an antibiotic. For example, the formulation can be administered after the entire antibiotic regimen or course is complete.

In some embodiments, a formulation is administered before, during, and/or after food intake by a subject. In some embodiments, the formulation is administered with food intake by the subject. In some embodiments, the formulation is administered with (e.g., simultaneously) with food intake.

In some embodiments, the formulation is administered before food intake by a subject. In some embodiments, the formulation is more effective or potent at treating a microbial condition when administered before food intake. For example, the formulation can be administered about 1 minute, about 2 minutes, about 3 minutes, about 5 minutes, about 10 minutes, about 15 minutes, about 30 minutes, about 45 minutes, about 1 hour, about 2 hours, about 3 hours, about 4 hours, about 5 hours, about 6 hours, about 7 hours, about 8 hours, about 9 hours, about 10 hours, about 12 hours, or about 1 day before food intake by a subject. For example, the formulation can be administered at least about 1 minute, about 2 minutes, about 3 minutes, about 5 minutes, about 10 minutes, about 15 minutes, about 30 minutes, about 45 minutes, about 1 hour, about 2 hours, about 3 hours, about 4 hours, about 5 hours, about 6 hours, about 7 hours, about 8 hours, about 9 hours, about 10 hours, about 12 hours, or about 1 day before food intake by a subject. For example, the formulation can be administered at most about 1 minute, about 2 minutes, about 3 minutes, about 5 minutes, about 10 minutes, about 15 minutes, about 30 minutes, about 45 minutes, about 1 hour, about 2 hours, about 3 hours, about 4 hours, about 5 hours, about 6 hours, about 7 hours, about 8 hours, about 9 hours, about 10 hours, about 12 hours, or about 1 day before food intake by a subject.

In some embodiments, the formulation is administered after food intake by the subject. In some embodiments, the formulation is more effective or potent at treating a microbial condition when administered after food intake. For example, the formulation can be administered at least about 1 minute, 2 minutes, 3 minutes, 5 minutes, 10 minutes, 15 minutes, 30 minutes, 45 minutes, 1 hour, 2 hours, 3 hours, 5 hours, 10 hours, 12 hours, or 1 day after food intake by a subject. For example, the formulation can be administered at most about 1 minute, 2 minutes, 3 minutes, 5 minutes, 10 minutes, 15 minutes, 30 minutes, 45 minutes, 1 hour, 2 hours, 3 hours, 5 hours, 10 hours, 12 hours, or 1 day after food intake by a subject.

Formulations provided herein can include those suitable for oral including buccal and sub-lingual, intranasal, topical, transdermal, transdermal patch, pulmonary, vaginal, rectal, suppository, mucosal, systemic, or parenteral including intramuscular, intraarterial, intrathecal, intradermal, intraperitoneal, subcutaneous, and intravenous administration or in a form suitable for administration by aerosolization, inhalation or insufflation.

A therapeutic or cosmetic composition can include carriers and excipients (including but not limited to buffers, carbohydrates, lipids, mannitol, proteins, polypeptides or amino acids such as glycine, antioxidants, bacteriostats, chelating agents, suspending agents, thickening agents and/or preservatives), metals (e.g., iron, calcium), salts, vitamins, minerals, water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances as required to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavouring agents, dispersion enhancer, disintegrant, coating agents, plasticizers, preservatives, suspending agents, emulsifying agents, plant cellulosic material and spheronization agents, and any combination thereof.

Non-limiting examples of pharmaceutically-acceptable excipients can be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), each of which is incorporated by reference in its entirety.

A therapeutic or cosmetic composition can be substantially free of preservatives. In some applications, the composition may contain at least one preservative.

A therapeutic or cosmetic composition can be encapsulated within a suitable vehicle, for example, a liposome, a microspheres, or a microparticle. Microspheres formed of polymers or proteins can be tailored for passage through the gastrointestinal tract directly into the blood stream. Alternatively, the compound can be incorporated and the microspheres, or composite of microspheres, and implanted for slow release over a period of time ranging from days to months.

A therapeutic or cosmetic composition can be formulated as a sterile solution or suspension. The therapeutic or cosmetic compositions can be sterilized by conventional techniques or may be sterile filtered. The resulting aqueous solutions may be packaged for use as is, or lyophilized. The lyophilized preparation of the microbial composition can be packaged in a suitable form for oral administration, for example, capsule or pill.

The compositions can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compositions can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as a mixture of fatty acid glycerides, optionally in combination with cocoa butter, can be used.

In practicing the methods of treatment or use provided herein, therapeutically-effective amounts of the microbial compositions described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, potency of the formulation, and other factors. Subjects can be, for example, humans, elderly adults, adults, adolescents, pre-adolescents, children, toddlers, infants, or neonates. A subject can be a patient. A subject can be an individual enrolled in a clinical study. A subject can be a laboratory animal, for example, a mammal, or a rodent.

Pharmaceutical compositions can be formulated using one or more physiologically-acceptable carriers comprising excipients and auxiliaries, which facilitate processing of the microorganisms into preparations that can be used pharmaceutically. Formulation can be modified depending upon the route of administration chosen. Pharmaceutical compositions described herein can be manufactured in a conventional manner, for example, by means of conventional mixing, dissolving, granulating, vitrification, spray-drying, lyophilizing, dragee-making, levigating, encapsulating, entrapping, emulsifying or compression processes.

In some embodiments, the pharmaceutical composition is manufactured in a dry form, for example, by spray-drying or lyophilization. In some embodiments, the formulation is prepared as a liquid capsule to maintain the liquid form of the microbes.

Compositions provided herein can be stored at any suitable temperature. The formulation can be stored in cold storage, for example, at a temperature of about −80° C., about −20° C., about −4° C., or about 4° C. The storage temperature can be, for example, about 0° C., about 1° C., about 2° C., about 3° C., about 4° C., about 5° C., about 6° C., about 7° C., about 8° C., about 9° C., about 10° C., about 12° C., about 14° C., about 16° C., about 20° C., about 22° C., or about 25° C. In some embodiments, the storage temperature is between about 2° C. to about 8° C. Storage of microbial compositions at low temperatures, for example from about 2° C. to about 8° C., can keep the microbes alive and increase the efficiency of the composition, for example, when present in a liquid or gel formulation. Storage at freezing temperature, below 0° C., with a cryoprotectant can further extend stability.

The pH of the composition can range from about 3 to about 12. The pH of the composition can be, for example, from about 3 to about 4, from about 4 to about 5, from about 5 to about 6, from about 6 to about 7, from about 7 to about 8, from about 8 to about 9, from about 9 to about 10, from about 10 to about 11, or from about 11 to about 12 pH units. The pH of the composition can be, for example, about 3, about 4, about 5, about 6, about 7, about 8, about 9, about 10, about 11, or about 12 pH units. The pH of the composition can be, for example, at least 3, at least 4, at least 5, at least 6, at least 7, at least 8, at least 9, at least 10, at least 11 or at least 12 pH units. The pH of the composition can be, for example, at most 3, at most 4, at most 5, at most 6, at most 7, at most 8, at most 9, at most 10, at most 11, or at most 12 pH units. If the pH is outside the range desired by the formulator, the pH can be adjusted by using sufficient pharmaceutically-acceptable acids and bases. In some embodiments, the pH of the composition is between about 4 and about 6.

Pharmaceutical compositions containing microbes described herein can be administered for prophylactic and/or therapeutic treatments. In therapeutic applications, the compositions can be administered to a subject already suffering from a disease or condition, in an amount sufficient to cure or at least partially arrest the symptoms of the disease or condition, or to cure, heal, improve, or ameliorate the condition. Microbial compositions can also be administered to lessen a likelihood of developing, contracting, or worsening a condition. Amounts effective for this use can vary based on the severity and course of the disease or condition, previous therapy, the subject's health status, weight, and response to the drugs, and the judgment of the treating physician.

Multiple therapeutic agents can be administered in any order or simultaneously. If simultaneously, the multiple therapeutic agents can be provided in a single, unified form, or in multiple forms, for example, as multiple separate pills. The composition can be packed together or separately, in a single package or in a plurality of packages. One or all of the therapeutic agents can be given in multiple doses. If not simultaneous, the timing between the multiple doses may vary to as much as about a month.

Compositions described herein can be administered before, during, or after the occurrence of a disease or condition, and the timing of administering the composition can vary. For example, the microbial composition can be used as a prophylactic and can be administered continuously to subjects with a propensity to conditions or diseases in order to lessen a likelihood of the occurrence of the disease or condition. The microbial compositions can be administered to a subject during or as soon as possible after the onset of the symptoms. The administration of the microbial compositions can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A microbial composition can be administered as soon as is practicable after the onset of a disease or condition is detected or suspected, and for a length of time necessary for the treatment of the disease, such as, for example, from about 1 month to about 3 months. The length of treatment can vary for each subject.

Compositions of the invention can be administered in combination with another therapy, for example, immunotherapy, chemotherapy, radiotherapy, anti-inflammatory agents, anti-viral agents, anti-microbial agents, and anti-fungal agents.

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Dosing

The appropriate quantity of a therapeutic or cosmetic composition to be administered, the number of treatments, and unit dose can vary according to a subject and/or the disease state of the subject.

Pharmaceutical compositions described herein can be in unit dosage forms suitable for single administration of precise dosages. In unit dosage form, the formulation can be divided into unit doses containing appropriate quantities of one or more microbial compositions. The unit dosage can be in the form of a package containing discrete quantities of the formulation. Non-limiting examples are liquids in vials or ampoules. Aqueous suspension compositions can be packaged in single-dose non-reclosable containers. The composition can be in a multi-dose format. Multiple-dose reclosable containers can be used, for example, in combination with a preservative. Formulations for parenteral injection can be presented in unit dosage form, for example, in ampoules, or in multi-dose containers with a preservative.

The dosage can be in the form of a solid, semi-solid, or liquid composition. Non-limiting examples of dosage forms suitable for use in the invention include feed, food, pellet, lozenge, liquid, elixir, aerosol, inhalant, spray, powder, tablet, pill, capsule, gel, geltab, nanosuspension, nanoparticle, microgel, suppository troches, aqueous or oily suspensions, ointment, patch, lotion, dentifrice, emulsion, creams, drops, dispersible powders or granules, emulsion in hard or soft gel capsules, syrups, phytoceuticals, nutraceuticals, dietary supplement, and any combination thereof.

A microbe can be present in any suitable concentration in a pharmaceutical composition. The concentration of a microbe can be, for example, from about $10^1$ to about $10^{18}$ colony forming units (CFU). The concentration of a microbe can be, for example, at least $10^1$, at least $10^2$, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, at least $10^{15}$, at least $10^{16}$, at least $10^{17}$, or at least $10^{18}$ CFU. The concentration of a microbe can be, for example, at most $10^1$, at most $10^2$, at most $10^3$, at most $10^4$, at most $10^5$, at most $10^6$, at most $10^7$, at most $10^8$, at most $10^9$, at most $10^{10}$, at most $10^{11}$, at most $10^{12}$, at most $10^{13}$, at most $10^{14}$, at most $10^{15}$, at most $10^{16}$, at most $10^{17}$, or at most $10^{18}$ CFU. In some embodiments, the concentration of a microbe is from about $10^8$ CFU to about $10^9$ CFU. In some embodiments, the concentration of a microbe is about $10^8$ CFU. In some embodiments, the concentration of a microbe is about $10^9$ CFU.

Pharmaceutical compositions of the invention can be formulated with any suitable therapeutically-effective concentration of prebiotic. For example, the therapeutically-effective concentration of a prebiotic can be at least about 1 mg/ml, about 2 mg/ml, about 3 mg/ml, about 4 mg/ml, about 5 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, about 100 mg/ml, about 110 mg/ml, about 125 mg/ml, about 130 mg/ml, about 140 mg/ml, or about 150 mg/ml. For example, the therapeutically-effective concentration of a prebiotic can be at most about 1 mg/ml, about 2 mg/ml, about 3 mg/ml, about 4 mg/ml, about 5 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, about 100 mg/ml, about 110 mg/ml, about 125 mg/ml, about 130 mg/ml, about 140 mg/ml, or about 150 mg/ml. For example, the therapeutically-effective concentration of a prebiotic can be about 1 mg/ml, about 2 mg/ml, about 3 mg/ml, about 4 mg/ml, about 5 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, about 100 mg/ml, about 110 mg/ml, about 125 mg/ml, about 130 mg/ml, about 140 mg/ml, or about 150 mg/ml. In some embodiments, the concentration of a prebiotic in a pharmaceutical composition is about 70 mg/ml. In some embodiments, the prebiotic is inulin.

Pharmaceutical compositions of the invention can be administered, for example, 1, 2, 3, 4, 5, or more times daily. Pharmaceutical compositions of the invention can be administered, for example, daily, every other day, three times a week, twice a week, once a week, or at other appropriate intervals for treatment of the condition.

Computer Systems

Figure 7:
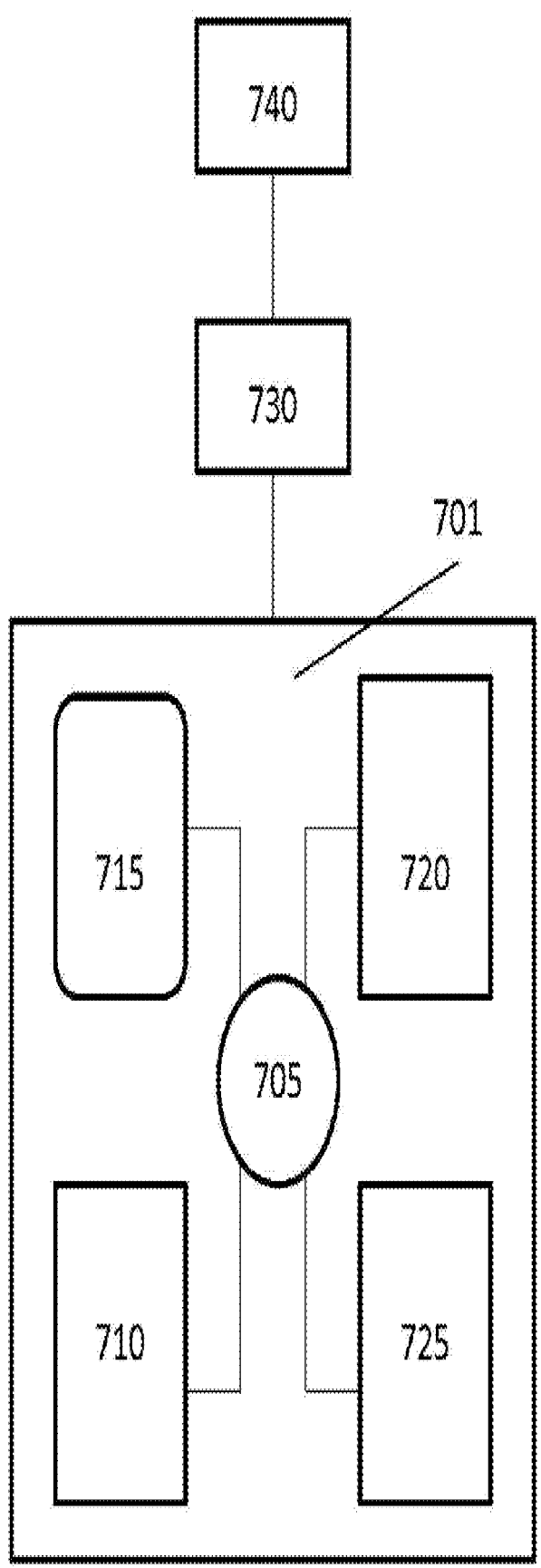
FIG. 7 depicts a system adapted to enable a user to detect, analyze, and process data (e.g. sequencing data, strain classification, functional pathways, epigenetic changes, patient information, external data, databases, microbiome strains; therapeutic consortia, etc.) using machine readable code.

The invention also provides a computer system that is configured to implement the methods of the disclosure. The system can include a computer server ("server") that is programmed to implement the methods described herein. FIG. 7 depicts a system 700 adapted to enable a user to detect, analyze, and process data (e.g. sequencing data; strain classification, functional pathways, epigenetic changes, patient information, external data, databases, microbiome strains; therapeutic consortia, etc.). The system 700 includes a central computer server 701 that is programmed to implement exemplary methods described herein. The server 701 includes a central processing unit (CPU, also "processor") 705 which can be a single core processor, a multi core processor, or plurality of processors for parallel processing, or cloud processors. The server 701 also includes memory 710 (e.g. random access memory, read-only memory, flash memory); electronic storage unit 715 (e.g. hard disk); communications interface 720 (e.g. network adaptor) for communicating with one or more other systems; and peripheral devices 725 which may include cache, other memory, data storage, and/or electronic display adaptors. The memory 710, storage unit 715, interface 720, and peripheral devices 725 are in communication with the processor 705 through a communications bus (solid lines), such as a motherboard. The storage unit 715 can be a data storage unit for storing data. The server 701 is operatively coupled to a computer network ("network") 730 with the aid of the communications interface 720. The network 730 can be the Internet, an intranet and/or an extranet, an intranet and/or extranet that is in communication with the Internet, a telecommunication or data network. The network 730 in some cases, with the aid of the server 701, can implement a peer-to-peer network, which may enable devices coupled to the server 701 to behave as a client or a server. Peripheral devices can include, e.g. sequencers 725 or remote computer systems 740.

The storage unit 715 can store files, (e.g. any aspect of data associated with the invention). In some instances cloud storage is used. Cloud storage can be a model of data storage where the digital data is stored in logical pools, wherein the physical storage can span multiple servers and, in some instances, one or more locations. In some embodiments, the physical environment is owned and managed by a hosting company. Cloud storage services may be accessed, e.g., through a co-located cloud compute service, a web service application programming interface (API) or by applications that utilize the API, such as cloud desktop storage, a cloud storage gateway or Web-based content management systems.

The server can communicate with one or more remote computer systems through the network 730. The one or more remote computer systems may be, for example, personal computers, laptops, tablets, telephones, Smart phones, or personal digital assistants.

In some situations the system 700 includes a single server 701. In other situations, the system includes multiple servers in communication with one another through an intranet, extranet and/or the Internet.

The server 701 can be adapted to store information. Such information can be stored on the storage unit 715 or the server 701 and such data can be transmitted through a network.

Methods as described herein can be implemented by way of machine (e.g., computer processor) computer readable medium (or software) stored on an electronic storage location of the server 701, such as, for example, on the memory 710, or electronic storage unit 715. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710. Alternatively, the code can be executed on a second computer system 740.

Aspects of the systems and methods provided herein, such as the server 701, can be embodied in programming. Various aspects of the technology may be thought of as "products" or "articles of manufacture" typically in the form of machine (or processor) executable code and/or associated data that is carried on or embodied in a type of machine readable medium (e.g., computer readable medium). Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless likes, optical links, or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, tangible storage medium, a carrier wave medium, or physical transmission medium. Non-volatile storage media can include, for example, optical or magnetic disks, such as any of the storage devices in any computer(s) or the like, such may be used to implement the system. Tangible transmission media can include: coaxial cables, copper wires, and fiber optics (including the wires that comprise a bus within a computer system). Carrier-wave transmission media may take the form of electric or electromagnetic signals, or acoustic or light waves such as those generated during radio frequency (RF) and infrared (IR) data communications. Common forms of computer-readable media therefore include, for example: a floppy disk, a flexible disk, hard disk, magnetic tape, any other magnetic medium, a CD-ROM, DVD, DVD-ROM, any other optical medium, punch cards, paper tame, any other physical storage medium with patterns of holes, a RAM, a ROM, a PROM and EPROM, a FLASH-EPROM, any other memory chip or cartridge, a carrier wave transporting data or instructions, cables, or links transporting such carrier wave, or any other medium from which a computer may read programming code and/or data. Many of these forms of computer readable media may be involved in carrying one or more sequences of one or more instructions to a processor for execution.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1: Media for Growing Bacteria Strains

A microbial strain of the invention can be grown using the media described in this example.

For preparing the media, combine all ingredients shown in Table 7:

TABLE 7

Recipe for growth media

| PYGveg Component | Amount per liter |
|---|---|
| Glucose | 5 g |
| $K_2HPO_4$ | 2 g |
| Tween 80 | 1 ml |
| Cystein-HCl | 0.5 g |
| Yeast extract | 10 g |
| HiVeg Extract | 5 g |
| HiVeg Peptone #1 | 5 g |
| HiVeg Peptone #3 | 5 g |
| Vitamin Mix 100x | 10 ml |
| Salt solution | 40 ml |

| Salt solution Component | grams per liter |
|---|---|
| $CaCl_2$ $2H_2O$ | 0.02 |
| $MgSO_4$ $7H_2O$ | 0.02 |
| $K_2HPO_4$ | 0.04 |
| $KH_2PO_4$ | 0.04 |
| $NaHCO_3$ | 0.4 |
| NaCl | 0.08 |

Dissolve the ingredients in boiling water, which can contain less oxygen. Purge with nitrogen gas until the medium is completely anaerobic. Seal bottle with rubber septum. Let the medium cool down. Perform aliquoting of the anaerobic medium in a glove box to maintain anaerobic condition. Autoclave the medium for about 20 minutes at 121 degrees Celsius. Let the medium cool down and add the appropriate amount of 100x vitamins, shown in Table 8 below, to result in 1x final solution of growth medium.

TABLE 8

Vitamin solution

| Vitamin Solution Component | milligrams per liter |
|---|---|
| D-biotin | 0.2 |
| Ca-pantothenate | 2.5 |
| myoinositol | 20 |
| p-aminobenzoic acid | 0.5 |
| pyridoxine hydrochloride | 5 |
| riboflavine | 0.5 |
| thiamine dichloride | 10 |
| vitamin B12 | 0.2 |
| nicotinic acid | 5 |

Figure 14:
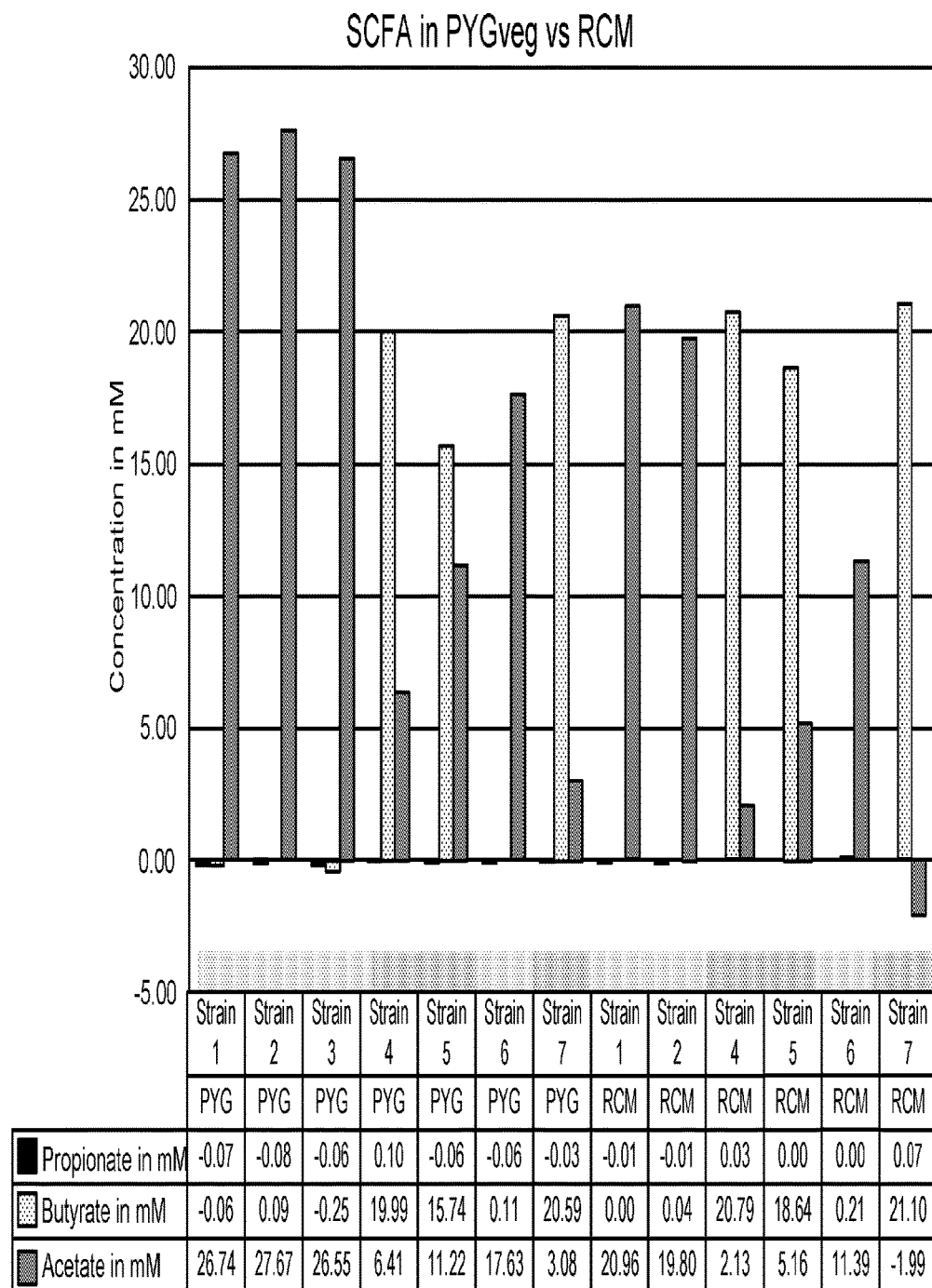

FIG. 14 illustrates exemplary data for short chain fatty acid quantification in different media (e.g., RCM, PYG) by strain. The short chain fatty acid quantification shows that the predicted genomic function of the strains matches the actual function. This can be similar for different media. In one non-limiting example, strain 1 can be *Bifidobacterium adolescentis* (BADO). In one non-limiting example, strain 2 can be *Bifidobacterium infantis* (BINF). In one non-limiting example, strain 3 can be *Bifidobacterium longum* (BLON). In one non-limiting example, strain 4 can be *Clostridium beijerinckii* (CBEI). In one non-limiting example, strain 5 can be *Clostridium butyricum* (CBUT). In one non-limiting example, strain 6 can be *Clostridium indolis* (CIND). In one non-limiting example, strain 7 can be *Eubacterium hallii* (EHAL).

Figure 15:
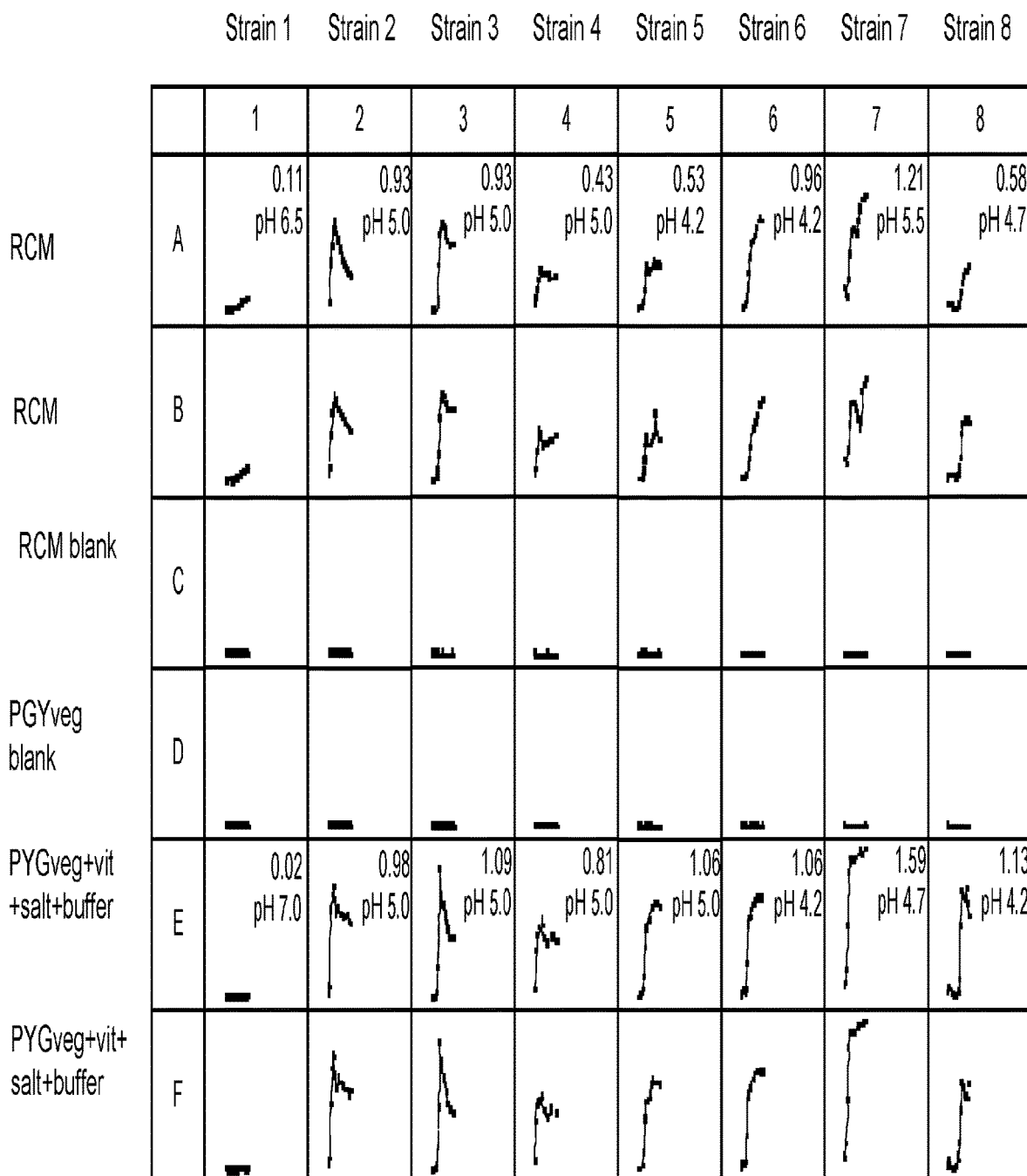

FIG. 15 illustrates that improved media of the invention (e.g., PYGveg+vit+salt+buffer) can result in higher peak bacterial density. In one non-limiting example, strain 1 can be *Akkermansia muciniphila* (AMUC). In one non-limiting example, strain 2 can be CBEI. In one non-limiting example, strain 3 can be EHAL. In one non-limiting example, strain 4 can be CIND. In one non-limiting example, strain 5 can be BLON. In one non-limiting example, strain 6 can be BADO. In one non-limiting example, strain 7 can be CBUT. In one non-limiting example, strain 8 can be BINF.

Example 2: Stability of Strains in Formulation

FIG. 9 illustrates the stability of microbial strains *Clostridium butyricum* (CBUT), *Clostridium beijerinckii* (CBEI), *Bifidobacterium longum* (BLON), and *Bifidobacterium infantis* (BINF) when present individually or alone as compared to that observed when present together in a formulation, for example, WB0002 and WB0003.

In one non-limiting example of the invention, WB0002 comprises *Clostridium butyricum* (CBUT), *Clostridium beijerinckii* (CBEI), *Bifidobacterium longum* (BLON), and *Bifidobacterium infantis* (BINF), *B. adolescentis, A. muciniphila, E. hallii*, and *C. indolis.*

In one non-limiting example of the invention, WB0003 comprises the strains *Clostridium butyricum* (CBUT), *Clostridium beijerinckii* (CBEI), *Bifidobacterium longum* (BLON), *Bifidobacterium infantis* (BINF), *B. adolescentis, A. muciniphila, E. hallii*, and *C. indolis*, and a prebiotic (e.g. inulin).

Example 3: Treatment of a Metabolic Condition with a Microbial Composition

FIGS. 10 and 11A and B illustrate results of a preclinical study testing the effect of a microbial composition of the invention (e.g., WB0002 and WB0003) on diet-induced obese mice.

In one non-limiting example of the invention, WB0002 comprises *Clostridium butyricum* (CBUT), *Clostridium beijerinckii* (CBEI), *Bifidobacterium longum* (BLON), *Bifidobacterium infantis* (BINF), *B. adolescentis, A. muciniphila, E. hallii*, and *C. indolis.*

In one non-limiting example of the invention, WB0003 comprises the strains *Clostridium butyricum* (CBUT), *Clostridium beijerinckii* (CBEI), *Bifidobacterium longum* (BLON), *Bifidobacterium infantis* (BINF), *B. adolescentis, A. muciniphila, E. hallii*, and *C. indolis*, and a prebiotic (e.g. inulin).

As illustrated in FIG. 10, the microbial composition WB00003 resulted in increased weight loss during the dosing period.

FIGS. 11A and B illustrate glucose control in mice dosed with formulations of the invention as compared with controls.

Example 4: Treatment of a Metabolic Condition with a Microbial Composition

A subject with a metabolic condition, for example, obesity, insulin insensitivity, T2DM, and/or T1DM comes to a medical professional for treatment.

The medical professional prescribes a microbial-based oral composition comprising the microbial strains *Akkermansia muciniphila, Bifidobacterium adolescentis, Bifidobacterium infantis, Bifidobacterium longum, Clostridium beijerinckii, Clostridium butyricum, Clostridium indolis,* and *Eubacterium hallii*. The composition may additionally comprise *Faecalibacterium prausnitzii* in some embodiments. Each strain is present in a range of about $10^8$ to about $10^9$ CFU in the composition. The composition additionally comprises inulin at a concentration of about 70 mg/mL. The expected delivery form of the oral composition is an enteric-coated (e.g., pH sensitive polymer Eudragit FS30D) pill that can protect against stomach acidity and deliver to the ileum/upper colon region of the subject. The enteric coating is designed to dissolve at a pH greater than about 6.5-7. In some embodiments, the oral composition is administered as a liquid capsule.

The subject is administered the composition before food intake (e.g., 1 hour before meals) twice daily for fourteen consecutive days. In some cases, the composition is administered simultaneously with food intake.

The microbial composition alters the microbial habitat of the gut of the subject to that of a healthy subject. The subject loses weight. The subject's metabolic condition, for example, obesity, insulin insensitivity, T2DM, and/or T1DM is treated by the composition.

In some embodiments, a sample is taken from the subject to personalize the composition of the microbial-based oral composition. For example, if the subject has a low level of one or more of the microbial strains, a microbial-based oral composition may be administered that contains the one or more of the microbial strains that the subject is deficient in.

Example 5: Study to Evaluate Microbial Compositions in Treating a Metabolic Condition Objective:

The purpose of the study is to assess the effect of microbial compositions of the invention in treating a metabolic condition, for example, obesity, insulin insensitivity, T2DM, and/or T1DM.

Methods:

Twenty subjects with a metabolic disorder, enter a double-blind, placebo controlled and randomized study.

1) Experimental group: Ten subjects are given oral compositions containing the active composition comprising: *Akkermansia muciniphila, Bifidobacterium adolescentis, Bifidobacterium infantis, Bifidobacterium longum, Clostridium beijerinckii, Clostridium butyricum, Clostridium indolis,* and *Eubacterium hallii* strains, and the prebiotic inulin. The composition can additionally comprise *Faecalibacterium prausnitzii*. The composition is taken once a day for 3 weeks before or simultaneously with meals. Parameters observed are weight of the subject and glucose tolerance before and after administration of the composition daily for 3 weeks.
2) Control group: Ten subjects are given a placebo pill. The placebo is taken once a day for 3 weeks. Parameters observed are weight of the subject and glucose tolerance before and after administration of the composition daily for 3 weeks.

Predicted Results:

Following treatment, subjects in the experimental group have a restored gut microbiome, reduction in weight in obese subjects, and increased glucose tolerance compared with the control group.

Example 6: Treatment of a Metabolic Condition with a Microbial Composition

A subject with a metabolic condition, for example, obesity, insulin insensitivity, T2DM, and/or T1DM comes to a medical professional for treatment.

The medical professional prescribes a microbial-based oral composition comprising the microbial strains *Clostridium butyricum, Clostridium beijerinckii, Bifidobacterium longum,* and *Bifidobacterium infantis*. Each strain is present in a range of about $10^7$ to about $10^{12}$ CFU in the composition. The composition additionally comprises a prebiotic at a concentration of about 70 mg/mL. The expected delivery form of the oral composition is an enteric-coated (e.g., pH sensitive polymer Eudragit FS30D) pill that can protect against stomach acidity and deliver to the ileum/upper colon region of the subject. The enteric coating is designed to dissolve at a pH greater than about 6.5-7. In some embodiments, the oral composition is administered as a liquid capsule.

The subject is administered the composition before food intake (e.g., 1 hour before meals) twice daily for fourteen consecutive days.

The microbial composition alters the microbial habitat of the gut of the subject to that of a healthy subject. The subject loses weight. The subject's metabolic condition, for example, obesity, insulin insensitivity, T2DM, and/or T1DM is treated by the composition.

Example 7: Study to Evaluate Microbial Compositions in Treating a Metabolic Condition Objective:

The purpose of the study is to assess the effect of microbial compositions of the invention in treating a metabolic condition, for example, obesity, insulin insensitivity, T2DM, and/or T1DM.

Methods:

Twenty subjects with a metabolic disorder, enter a double-blind, placebo controlled and randomized study.

3) Experimental group: Ten subjects are given oral compositions containing the active composition comprising: *Clostridium butyricum, Clostridium beijerinckii, Bifidobacterium longum,* and *Bifidobacterium infantis*. The composition is taken once a day for 3 weeks before meals. Parameters observed are weight of the subject and glucose tolerance before and after administration of the composition daily for 3 weeks.
4) Control group: Ten subjects are given a placebo pill. The placebo is taken once a day for 3 weeks. Parameters observed are weight of the subject and glucose tolerance before and after administration of the composition daily for 3 weeks.

Predicted Results:

Following treatment, subjects in the experimental group have a restored gut microbiome, reduction in weight (e.g., in obese subjects), and increased glucose tolerance compared with the control group.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10842830B2). An electronic copy of the "Sequence Listing" will also be available from the USPTO upon request and payment of the fee set forth in 37 CFR 1.19(b)(3).

What is claimed is:

1. A dosage form comprising:
   a) a first microbe comprising a 16S rRNA sequence comprising at least 97% sequence identity to a 16S rRNA sequence of *Akkermansia muciniphila*,
   b) a second microbe comprising a 16S rRNA sequence comprising at least 97% sequence identity to a 16S rRNA sequence of *Eubacterium hallii*, and
   c) a third microbe comprising a 16S rRNA sequence comprising at least 97% sequence identity to a 16S rRNA sequence of *Clostridium beijerinckii*;
   wherein said dosage form comprises:
      an enteric coating, or
      an effective amount of a preservative.

2. The dosage form of claim 1, wherein said dosage form comprises at least $1 \times 10^5$ CFUs of said first microbe.

3. The dosage form of claim 1, wherein said dosage form comprises at least $1 \times 10^5$ CFUs of said second microbe.

4. The dosage form of claim 1, wherein said dosage form is a unit dosage form.

5. The dosage form of claim 1, wherein said dosage form is in a single capsule.

6. The dosage form of claim 1, wherein said dosage form is a food bar.

7. The dosage form of claim 1, wherein said dosage form further comprises one or more additional microbes selected from the group consisting of: *Bifidobacterium adolescentis*, *Bifidobacterium infantis*, *Bifidobacterium longum*, *Clostridium indolis*, and *Faecalibacterium prausnitzii*.

8. The dosage form of claim 1, wherein said dosage form further comprises *Bifidobacterium infantis*.

9. The dosage form of claim 1, wherein said third microbe is *Clostridium beijerinckii*.

10. The dosage form of claim 1, wherein said first microbe is *Akkermansia muciniphila*.

11. The dosage form of claim 1, wherein said second microbe is *Eubacterium hallii*.

12. The dosage form of claim 1, wherein said microbes are in a powder form in said dosage form.

13. The dosage form of claim 1, wherein said microbes are in a liquid form in said dosage form.

14. The dosage form of claim 1, wherein said microbes are in a gel form in said dosage form.

15. The dosage form of claim 1, wherein said dosage form does not contain dairy.

16. The dosage form of claim 1, wherein said first microbe, said second microbe, or said third microbe are lyophilized.

17. The dosage form of claim 1, wherein said dosage form is an oral dosage form.

18. The dosage form of claim 1, wherein said dosage form comprises at least $1 \times 10^5$ CFUs of said third microbe.

19. The dosage form of claim 1, wherein said dosage form comprises at least $1 \times 10^7$ CFUs of said first microbe, said second microbe, or said third microbe.

20. The dosage form of claim 1, wherein said first microbe, said second microbe, or said third microbe has been grown on plant-based media.

21. The dosage form of claim 1, wherein said 16S rRNA sequence of said first microbe comprises at least 99% sequence identity to said 16S rRNA sequence of *Akkermansia muciniphila*.

22. The dosage form of claim 1, wherein said 16S rRNA sequence of said second microbe comprises at least 99% sequence identity to said 16S rRNA sequence of *Eubacterium hallii*.

23. The dosage form of claim 1, wherein said 16S rRNA sequence of said third microbe comprises at least 99% sequence identity to said 16S rRNA sequence of *Clostridium beijerinckii*.

24. The dosage form of claim 1, wherein said 16S rRNA sequence of said first microbe comprises at least 99% sequence identity to said 16S rRNA sequence of *Akkermansia muciniphila*, said 16S rRNA sequence of said second microbe comprises at least 99% sequence identity to said 16S rRNA sequence of *Eubacterium hallii*, and said 16S rRNA sequence of said third microbe comprises at least 99% sequence identity to said 16S rRNA sequence of *Clostridium beijerinckii*.

25. The dosage form of claim 1, wherein said first microbe is *Akkermansia muciniphila*, said second microbe is *Eubacterium hallii*, and said third microbe is *Clostridium beijerinckii*.

* * * * *